United States Patent
Stevenson et al.

(10) Patent No.: US 10,750,743 B2
(45) Date of Patent: Aug. 25, 2020

(54) PYRIDAZINONE HERBICIDES

(71) Applicant: E.I. DU PONT DE NEMOURS AND COMPANY, Wilmington, DE (US)

(72) Inventors: Thomas Martin Stevenson, Newark, DE (US); Thomas Paul Selby, Hockessin, DE (US); Kimberly Katherine Marcus, Media, PA (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/771,867

(22) PCT Filed: Oct. 26, 2016

(86) PCT No.: PCT/US2016/058762
§ 371 (c)(1),
(2) Date: Apr. 27, 2018

(87) PCT Pub. No.: WO2017/074992
PCT Pub. Date: May 4, 2017

(65) Prior Publication Data
US 2018/0332851 A1    Nov. 22, 2018

Related U.S. Application Data

(60) Provisional application No. 62/247,585, filed on Oct. 28, 2015.

(51) Int. Cl.
*A01N 43/58* (2006.01)
*C07D 401/10* (2006.01)
(Continued)

(52) U.S. Cl.
CPC .......... *A01N 43/58* (2013.01); *A01N 43/647* (2013.01); *A01N 43/78* (2013.01); *A01N 43/80* (2013.01);
(Continued)

(58) Field of Classification Search
CPC .. C07D 401/04; C07D 401/10; C07D 405/10; C07D 409/04; C07D 409/10;
(Continued)

(56) References Cited

U.S. PATENT DOCUMENTS 9,049,864 B2     6/2015   Burton et al.
10,118,917 B2 *  11/2018  Selby ............... A01N 43/58
(Continued)

FOREIGN PATENT DOCUMENTS

GB        1130716 A      10/1968
GB        2519092 A      4/2015
(Continued)

OTHER PUBLICATIONS

International Search Report of PCT/US2016/058762 dated Apr. 5, 2017.
(Continued)

*Primary Examiner* — John Pak
(74) *Attorney, Agent, or Firm* — Reed A Coats

(57) ABSTRACT

Disclosed are compounds of Formula 1, including all stereoisomers, N-oxides, and salts thereof, agricultural compositions containing them and their use as herbicides

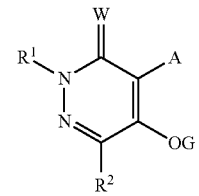

wherein $R^1$, $R^2$, G and W are as defined in the disclosure, and
A is selected from

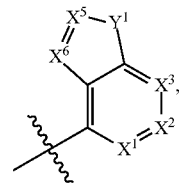

A-1

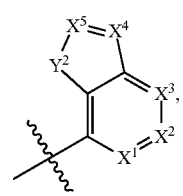

A-2

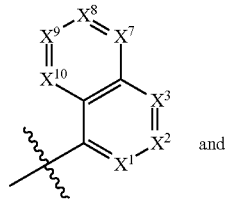

A-3 and

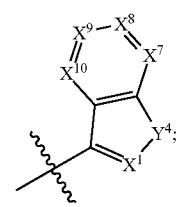

A-4

(Continued)

and $X^1, X^2, X^3, X^4, X^5, X^6, X^7, X^8, X^9, X^{10}, Y^1, Y^2$, and $Y^4$ are as defined in the disclosure.

12 Claims, No Drawings

(51) Int. Cl.

| | | |
|---|---|---|
| *C07D 405/10* | (2006.01) | |
| *C07D 409/10* | (2006.01) | |
| *C07D 495/04* | (2006.01) | |
| *C07D 401/04* | (2006.01) | |
| *C07D 409/04* | (2006.01) | |
| *A01N 43/90* | (2006.01) | |
| *A01N 47/06* | (2006.01) | |
| *C07D 417/04* | (2006.01) | |
| *C07D 405/04* | (2006.01) | |
| *C07D 403/04* | (2006.01) | |
| *A01N 43/80* | (2006.01) | |
| *A01N 43/647* | (2006.01) | |
| *A01N 43/78* | (2006.01) | |

(52) U.S. Cl.
CPC ............ *A01N 43/90* (2013.01); *A01N 47/06* (2013.01); *C07D 401/04* (2013.01); *C07D 401/10* (2013.01); *C07D 403/04* (2013.01); *C07D 405/04* (2013.01); *C07D 405/10* (2013.01); *C07D 409/04* (2013.01); *C07D 409/10* (2013.01); *C07D 417/04* (2013.01); *C07D 495/04* (2013.01)

(58) Field of Classification Search
CPC ...... C07D 495/04; A01N 43/58; A01N 43/90; A01N 47/06
See application file for complete search history.

(56) References Cited

U.S. PATENT DOCUMENTS

| | | |
|---|---|---|
| 2005/0020594 A1 | 1/2005 | Hepperle et al. |
| 2010/0216642 A1 | 8/2010 | Fusaka |
| 2011/0098269 A1 | 4/2011 | Becknell et al. |
| 2013/0172556 A1 | 7/2013 | Jachmann et al. |
| 2014/0378688 A1 | 12/2014 | Jachmann et al. |
| 2017/0050953 A1 | 2/2017 | Selby et al. |

FOREIGN PATENT DOCUMENTS

| | | |
|---|---|---|
| WO | 2009/086041 A1 | 7/2009 |
| WO | 2011/045271 A1 | 4/2011 |
| WO | 2013/160126 A1 | 10/2013 |
| WO | 2014/031971 A1 | 2/2014 |
| WO | 2015/052095 A1 | 4/2015 |
| WO | 2015/168010 A1 | 11/2015 |
| WO | 2017/074988 A1 | 5/2017 |

OTHER PUBLICATIONS

Babichev et al. 6-Amino-1-Aryl-4-Pyridazinones and Their Derivatives, Ukrainskii Khimicheskii Zhurnal (Russian edition), 1983 49(11):1197-202.

* cited by examiner

PYRIDAZINONE HERBICIDES

FIELD OF THE INVENTION

This invention relates to certain pyridazinone herbicides, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1, including all stereoisomers, N-oxides, and salts thereof, agricultural compositions containing them and their use as herbicides

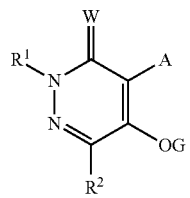

1 wherein
R$^1$ is H, C$_1$-C$_7$ alkyl, C$_3$-C$_8$ alkylcarbonylalkyl, C$_3$-C$_8$ alkoxycarbonylalkyl, C$_4$-C$_7$ alkylcycloalkyl, C$_3$-C$_7$ alkenyl, C$_3$-C$_7$ alkynyl, C$_3$-C$_7$ cycloalkyl, C$_4$-C$_7$ cycloalkylalkyl, C$_2$-C$_3$ cyanoalkyl, C$_1$-C$_4$ nitroalkyl, C$_2$-C$_7$ haloalkoxyalkyl, C$_1$-C$_7$ haloalkyl, C$_3$-C$_7$ haloalkenyl, C$_2$-C$_7$ alkoxyalkyl, C$_3$-C$_7$ alkylthioalkyl, C$_1$-C$_7$ alkoxy, benzyl or phenyl; or a 5- or 6-membered saturated or partially saturated heterocyclic ring containing ring members selected from carbon and up to 1O and 1S;
W is O or S;
A is selected from

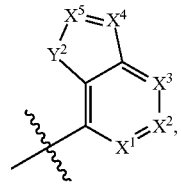

A-1

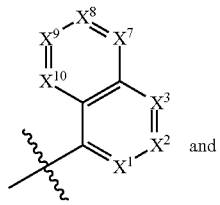

A-2

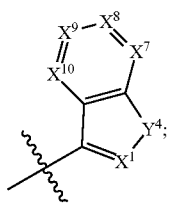

A-3 and

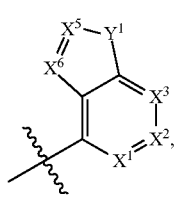

A-4

G is G$^1$ or W$^1$G$^1$;
W$^1$ is C$_1$-C$_4$ alkanediyl or C$_2$-C$_4$ alkenediyl;
G$^1$ is H, —C(=O)R$^7$, —C(=S)R$^7$, —CO$_2$R$^8$, —C(=O)SR$^8$, —S(O)$_2$R$^7$, —CONR$^9$R$^{10}$, —S(O)$_2$NR$^9$R$^{10}$ or P(=O)R$^{11}$; or C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_1$-C$_4$ alkoxyalkyl, C$_3$-C$_6$ cycloalkyl or C$_4$-C$_7$ cycloalkylalkyl; or a 5- or 6-membered heterocyclic ring;
R$^2$ is H, halogen, —CN, —CHO, C$_1$-C$_7$ alkyl, C$_3$-C$_8$ alkylcarbonylalkyl, C$_3$-C$_8$ alkoxycarbonylalkyl, C$_1$-C$_4$ alkylcarbonyl, C$_2$-C$_7$ alkylcarbonyloxy, C$_4$-C$_7$ alkylcycloalkyl, C$_3$-C$_7$ alkenyl, C$_3$-C$_7$ alkynyl, C$_1$-C$_4$ alkylsulfinyl, C$_1$-C$_4$ alkylsulfonyl, C$_1$-C$_4$ alkylamino, C$_2$-C$_8$ dialkylamino, C$_3$-C$_7$ cycloalkyl, C$_4$-C$_7$ cycloalkylalkyl, C$_2$-C$_3$ cyanoalkyl, C$_1$-C$_4$ nitroalkyl, C$_2$-C$_7$ haloalkoxyalkyl, C$_1$-C$_7$ haloalkyl, C$_3$-C$_7$ haloalkenyl, C$_2$-C$_7$ alkoxyalkyl, C$_1$-C$_7$ alkoxy, C$_1$-C$_5$ alkylthio or C$_2$-C$_3$ alkoxycarbonyl; or phenyl optionally substituted by halogen, C$_1$-C$_4$ alkyl or C$_1$-C$_4$ haloalkyl;
each X$^1$ is independently N or CR$^3$;
each X$^2$ is independently N or CR$^3$;
each X$^3$ is independently N or CR$^3$;
each X$^4$, X$^5$ and X$^6$ is independently N or CR$^4$;
each X$^7$, X$^8$, X$^9$ and X$^{10}$ is independently N or CR$^5$;
Y$^1$ is O, S or NR$^6$;
Y$^2$ is O, S or NR$^6$;
Y$^4$ is O, S or NR$^6$;
each R$^3$ is independently H, halogen, nitro, —CN, C$_1$-C$_5$ alkyl, C$_2$-C$_5$ alkenyl, C$_2$-C$_5$ alkynyl, C$_3$-C$_5$ cycloalkyl, C$_4$-C$_5$ cycloalkylalkyl, C$_1$-C$_5$ haloalkyl, C$_3$-C$_5$ haloalkenyl, C$_3$-C$_5$ haloalkynyl, C$_2$-C$_5$ alkoxyalkyl, C$_1$-C$_5$ alkoxy, C$_1$-C$_5$ haloalkoxy, C$_1$-C$_5$ alkylthio, C$_1$-C$_4$ alkylsulfinyl, C$_1$-C$_4$ alkylsulfonyl, C$_1$-C$_5$ haloalkylthio or C$_2$-C$_5$ alkoxycarbonyl;
each R$^4$ is independently H, halogen, nitro, —CN, C$_1$-C$_5$ alkyl, C$_2$-C$_5$ alkenyl, C$_2$-C$_5$ alkynyl, C$_3$-C$_5$ cycloalkyl, C$_4$-C$_5$ cycloalkylalkyl, C$_1$-C$_5$ haloalkyl, C$_3$-C$_5$ haloalkenyl, C$_3$-C$_5$ haloalkynyl, C$_2$-C$_5$ alkoxyalkyl, C$_1$-C$_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

each $R^5$ is independently H, halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

$R^6$ is H, $C_1$-$C_7$ alkyl, $C_2$-$C_7$ alkenyl, $C_2$-$C_7$ alkynyl, $C_3$-$C_7$ cycloalkyl, $C_4$-$C_7$ cycloalkylalkyl, $C_1$-$C_7$ haloalkyl or $C_2$-$C_7$ alkoxyalkyl;

$R^7$ is $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl, $C_4$-$C_7$ cycloalkylalkyl; or phenyl, benzyl, or a 5- to 6-membered heterocyclic ring, each phenyl, benzyl or heterocyclic ring optionally substituted by halogen, $C_1$-$C_4$ alkyl or $C_1$-$C_4$ haloalkyl;

$R^8$ is $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl, $C_4$-$C_7$ cycloalkylalkyl; or phenyl, benzyl, or a 5- to 6-membered heterocyclic ring, each phenyl, benzyl or heterocyclic ring optionally substituted by halogen, $C_1$-$C_4$ alkyl or $C_1$-$C_4$ haloalkyl;

$R^9$ is $C_1$-$C_7$ alkyl, $C_3$-$C_7$ alkenyl, $C_3$-$C_7$ alkynyl, $C_3$-$C_7$ cycloalkyl, $C_2$-$C_7$ haloalkyl, $C_3$-$C_7$ haloalkenyl, $C_2$-$C_7$ alkoxyalkyl, $C_4$-$C_7$ cycloalkylalkyl; or phenyl, benzyl or a 5- to 6-membered heterocyclic ring, each phenyl, benzyl or heterocycling ring optionally substituted by halogen, $C_1$-$C_4$ alkyl or $C_1$-$C_4$ haloalkyl;

$R^{10}$ is H, $C_1$-$C_7$ alkyl, $C_2$-$C_7$ alkenyl, $C_2$-$C_7$ alkynyl, $C_3$-$C_7$ cycloalkyl, $C_4$-$C_7$ cycloalkylalkyl, $C_1$-$C_7$ haloalkyl or $C_2$-$C_7$ alkoxyalkyl; and $R^{11}$ is $C_1$-$C_7$ alkyl or $C_1$-$C_7$ alkoxy;

provided i) when A is A-3 and $X^2$ is $CR^3$, then $X^3$ is other than $CR^3$;

ii) when A is A-3 and $X^3$ is $CR^3$, then $X^2$ is other than $CR^3$;

iii) when A is A-4 and $Y^4$ is O, S or $NR^6$, then at least one of $X^7$, $X^8$, $X^9$ and $X^{10}$ is other than $CR^5$; and iv) when $R^1$ is $CH_3$; G is H or $C(=O)CH_3$; $R^2$ is Cl or Br; then A-3 is other than 4-quinolinyl(5-Cl), 5-quinolinyl, 4-isoquinolinyl, 5-isoquinolinyl, 6-isoquinolinyl and 8-isoquinolinyl.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating" refers reaction in which nucleophile displaces a leaving group such as halide or sulfonate from a carbon-containing radical. Unless otherwise indicated, the term "alkylating" does not limit the carbon-containing radical to alkyl.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2OCH_2$ and $CH_3CH_2OCH_2CH_2$. "Alkoxyalkoxy" denotes alkoxy substitution on alkoxy. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Cyanoalkyl" denotes an alkyl group substituted with one cyano group. Examples of "cyanoalkyl" include $NCCH_2$ and $NCCH_2CH_2$ (alternatively identified as $CH_2CH_2CN$).

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkylthio", "haloalkenyl", "haloalkynyl", and the like, areis defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$. Examples of "haloalkenyl" include $(Cl)_2C=CHCH_2-$ and $CF_3CH_2CH=CHCH_2-$. Examples of "haloalkynyl" include $HC\equiv CCHCl-$, $CF_3C\equiv C-$, $CCl_3C\equiv C-$ and $FCH_2C\equiv CCH_2-$.

"Alkoxycarbonyl" denotes a straight-chain or branched alkoxy moieties bonded to a C(=O) moiety. Examples of "alkoxycarbonyl" include $CH_3OC(=O)-$, $CH_3CH_2OC(=O)-$, $CH_3CH_2CH_2OC(=O)-$, $(CH_3)_2CHOC(=O)-$ and the different butoxy- or pentoxycarbonyl isomers. The term alkanediyl or alkenediyl refers to a linear or branched alkane or alkene linking chain respectively. Examples of alkanediyl include $-CH_2-$, $-CH_2CH(CH_3)-$ or $-CH_2CH_2CH_2-$. Examples of alkenediyl include $-CH=CH-$, $-CH_2C=CH-$ or $-CH=C(CH_3)-$. The term "adjacent" in the context of locating a substituent means "next to" or "immediately next to".

The total number of carbon atoms in a substituent group is indicated by the "$C_i$-$C_j$" prefix where i and j are numbers from 1 to 7. For example, $C_1$-$C_4$ alkylsulfonyl designates methylsulfonyl through butylsulfonyl; $C_2$ alkoxyalkyl designates $CH_3OCH_2-$; $C_3$ alkoxyalkyl designates, for example, $CH_3CH(OCH_3)-$, $CH_3OCH_2CH_2-$ or $CH_3CH_2OCH_2-$; and $C_4$ alkoxyalkyl designates the various isomers of an alkyl group substituted with an alkoxy group containing a total of four carbon atoms, examples including $CH_3CH_2CH_2OCH_2-$ and $CH_3CH_2OCH_2CH_2-$.

When a compound is substituted with a substituent bearing a subscript that indicates the number of said substituents can exceed 1, said substituents (when they exceed 1) are independently selected from the group of defined substituents, e.g., $(R^3)_n$, wherein n is 1, 2, 3 or 4. When a group contains a substituent which can be hydrogen, for example $R^2$ or $R^4$, then when this substituent is taken as hydrogen, it is recognized that this is equivalent to said group being unsubstituted. When a variable group is shown to be optionally attached to a position, for example $(R^3)_n$ wherein n may be 0, then hydrogen may be at the position even if not recited in the variable group definition. When one or more positions on a group are said to be "not substituted" or "unsubstituted", then hydrogen atoms are attached to take up any free valency.

The compounds of Formula 1 wherein G is H (i.e. the "OG" substituent of Formula 1 is a hydroxy moiety) are believed to be the compounds that bind to an active site on a plant enzyme or receptor causing herbicidal effect on the plant. Other compounds of Formula 1 wherein the substituent G is a group that can be transformed within plants or the environment to the hydroxy moiety provide similar herbicidal effects and are within the scope of the present invention. Therefore, G can be any derivative known in the art which does not extinguish the herbicidal activity of the compound of Formula 1 and is or can be hydrolyzed, oxidized, reduced or otherwise metabolized in plants or soil to provide the carboxylic acid function, which depending upon pH, is in the dissociated or the undissociated form. The term "ring system" denotes two or more fused rings. The term "bicyclic ring system" denotes a ring system consisting of two fused rings.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as an enolic function (e.g., when G is H), salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

When $R^7$, $R^8$ or $R^9$ is a 5- or 6-membered nitrogen-containing heterocyclic ring, it may be attached to the remainder of Formula 1 though any available carbon or nitrogen ring atom, unless otherwise described. As noted above, $R^7$, $R^8$ or $R^9$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein $R^v$ is as a substituent on $R^7$, $R^8$ or $R^9$ as defined in the Summary of the Invention, and r is an integer.

As noted above, $R^7$, $R^8$ or $R^9$ can be (among others) a 5- or 6-membered heterocyclic ring, which may be saturated or unsaturated, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention on $R^7$, $R^8$ or $R^9$ (i.e. halogen, $C_1$-$C_4$ alkyl or $C_1$-$C_4$ haloalkyl) and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

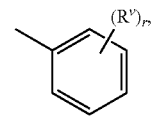

U-1

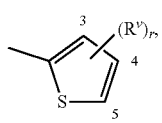

U-2

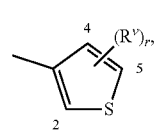

U-3

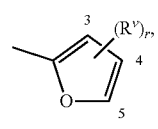

U-4

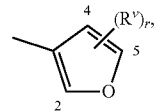

U-5

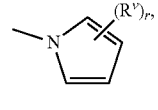

U-6

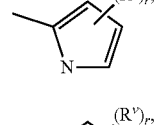

U-7

U-8

-continued
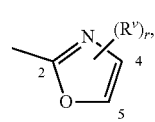 U-9
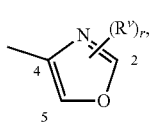 U-10
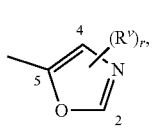 U-11
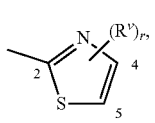 U-12
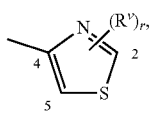 U-13
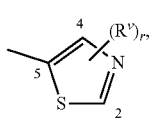 U-14
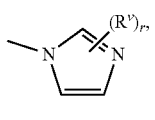 U-15
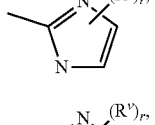 U-16
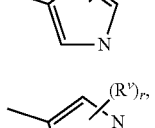 U-17
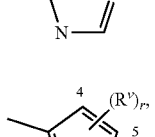 U-18
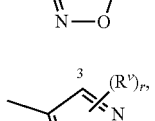 U-19
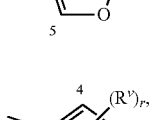 U-20
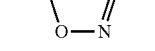 U-21
-continued
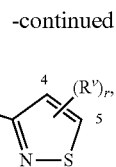 U-22
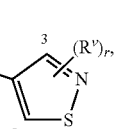 U-23
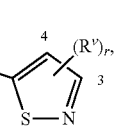 U-24
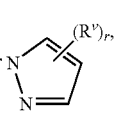 U-25
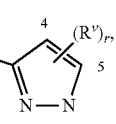 U-26
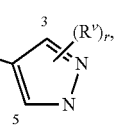 U-27
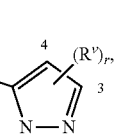 U-28
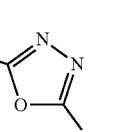 U-29
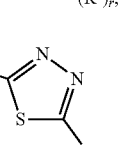 U-30
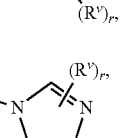 U-31
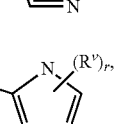 U-32
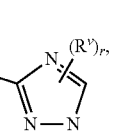 U-33

| | |
|---|---|
| 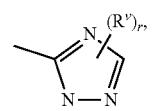 | U-34 |
| 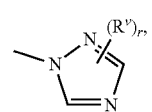 | U-35 |
| 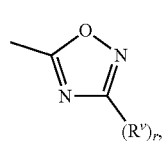 | U-36 |
| 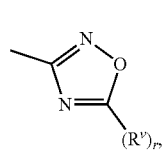 | U-37 |
| 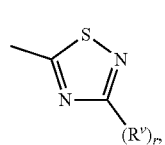 | U-38 |
| 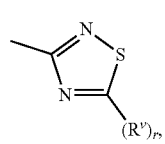 | U-39 |
| 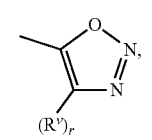 | U-40 |
| 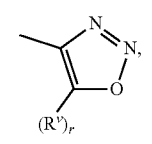 | U-41 |
| 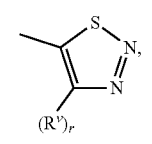 | U-42 |
| 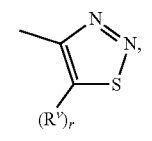 | U-43 |
| 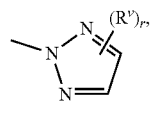 | U-44 |
| 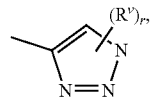 | U-45 |
| | |
|---|---|
| 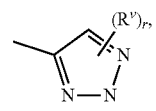 | U-46 |
| 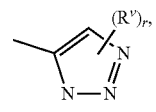 | U-47 |
| 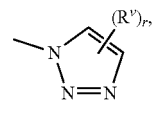 | U-48 |
| 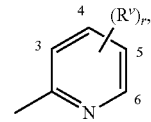 | U-49 |
| 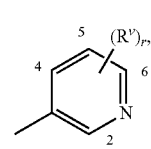 | U-50 |
| 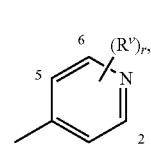 | U-51 |
| 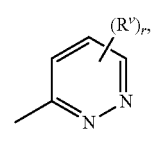 | U-52 |
| 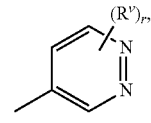 | U-53 |
| 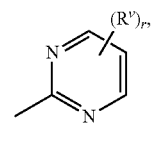 | U-54 |
| 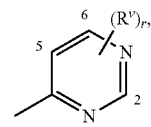 | U-55 |
| 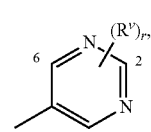 | U-56 |
| 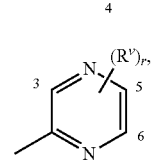 | U-57 |

-continued

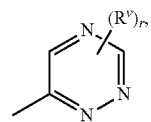  U-58

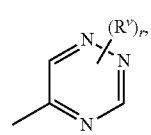  U-59

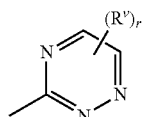 and  U-60

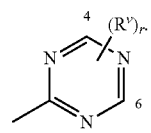  U-61

Note that when $R^7$, $R^8$ or $R^9$ is a 5- or 6-membered saturated or unsaturated nonaromatic heterocyclic ring optionally substituted with one or more substituents selected from the group of substituents as defined in the Summary of the Invention for $R^7$, $R^8$ or $R^9$, one or two carbon ring members of the heterocycle can optionally be in the oxidized form of a carbonyl moiety.

Examples of a 5- or 6-membered heterocyclic ring that is saturated or nonaromatic unsaturated heterocyclic ring containing ring members selected from up to two O atoms and up to two S atoms, and optionally substituted on carbon atom ring members with up to five halogen atoms includes the rings T-1 through T-35 as illustrated in Exhibit 2. Note that when the attachment point on the T group is illustrated as floating, the T group can be attached to the remainder of Formula 1 through any available carbon or nitrogen of the T group by replacement of a hydrogen atom. The optional substituents corresponding to $R^v$ can be attached to any available carbon or nitrogen by replacing a hydrogen atom. For these T rings, r is typically an integer from 0 to 4, limited by the number of available positions on each T group. The term "optionally substituted" means "substituted or unsubstituted"

Note that when $R^7$, $R^8$ or $R^9$ comprises a ring selected from T-28 through T-35, $G^2$ is selected from O, S or N. Note that when $T^2$ is N, the nitrogen atom can complete its valence by substitution with either H or the substituents corresponding to $R^v$ as defined in the Summary of the Invention on $R^7$, $R^8$ or $R^9$. Exemplary values for $R^1$ include T-1, T-2, T-7 and T-9.

Exhibit 2

  T-1

  T-2

  T-3

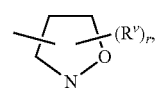  T-4

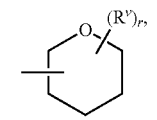  T-5

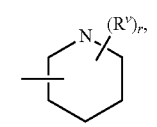  T-6

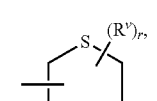  T-7

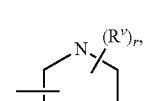  T-8

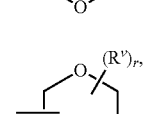  T-9

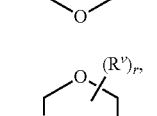  T-10

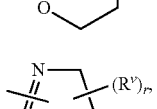  T-11

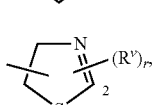  T-12

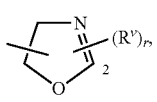  T-13

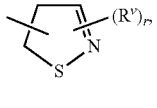  T-14

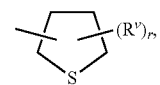  T-15

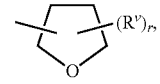  T-16

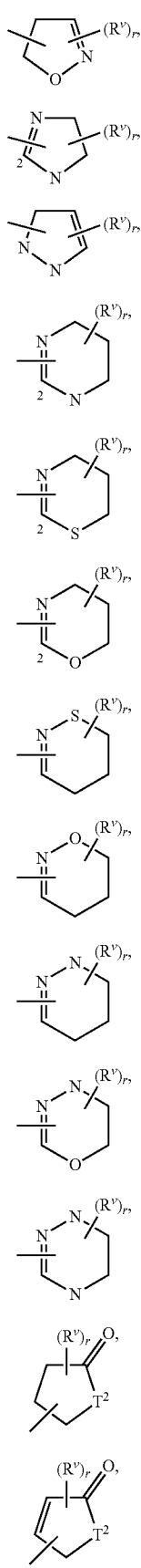

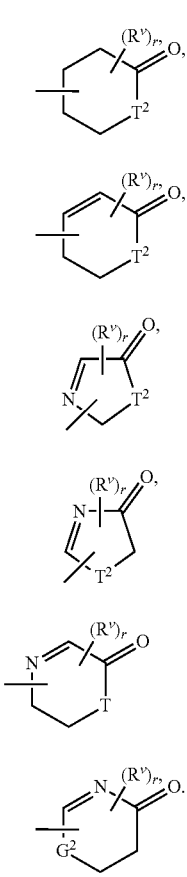

Although $R^v$ groups are shown in the structures U-1 through U-61, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Embodiments of the present invention as described in the Summary of the Invention include (where Formula 1 as used in the following Embodiments includes N-oxides and salts thereof):

Embodiment 1

A compound of Formula 1, N-oxides and salts thereof, compositions containing them, and methods of their use for controlling undesired vegetation as described in the Summary of the Invention.

Embodiment 2

A compound of Embodiment 1 wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl.

Embodiment 3

A compound of any one of Embodiments 1 or 2 wherein $R^1$ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl.

Embodiment 4

A compound of Embodiment 3 wherein $R^1$ is $C_1$-$C_4$ alkyl, $C_3$-$C_4$ cycloalkyl, $C_2$-$C_3$ cyanoalkyl, $C_1$-$C_3$ haloalkyl or $C_2$-$C_4$ alkoxyalkyl.

Embodiment 5

A compound of Embodiment 4 wherein $R^1$ is $C_1$-$C_3$ alkyl, $NCCH_2CH_2$—, $C_1$-$C_2$ haloalkyl or 2-methoxyethyl.

Embodiment 6

A compound of Embodiment 5 wherein $R^1$ is methyl, ethyl, n-propyl or 2-methoxyethyl.

Embodiment 7

A compound of Embodiment 6 wherein $R^1$ is methyl or ethyl.

Embodiment 8

A compound of Embodiment 6 wherein $R^1$ is methyl.

Embodiment 9

A compound of Embodiment 1 wherein $R^1$ is other than H.

Embodiment 10

A compound of Embodiment 1 wherein $R^1$ is other than phenyl.

Embodiment 11

A compound of any one of Embodiments 1 through 10 wherein W is O.

Embodiment 12

A compound of any one of Embodiments 1 through 11 wherein A is A-1, A-2 or A-3.

Embodiment 13

A compound of Embodiment 12 wherein A is A-3.

Embodiment 14

A compound of Embodiment 12 wherein A is A-1 or A-2.

Embodiment 15

A compound of Embodiment 14 wherein A is A-1.

Embodiment 16

A compound of Embodiment 14 wherein A is A-2.

Embodiment 17

A compound of any one of Embodiments 1 through 11 wherein A is A-3 or A-4.

Embodiment 18

A compound of Embodiment 17 wherein A is A-4.

Embodiment 19

A compound of any one of Embodiments 1 through 12, 14 or 15 wherein A is selected from

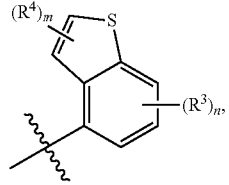
A-1-A

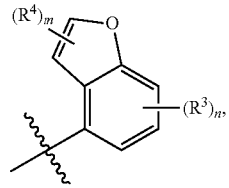
A-1-B

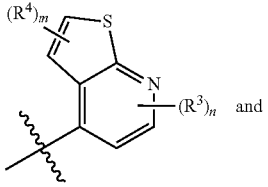
A-1-C
and

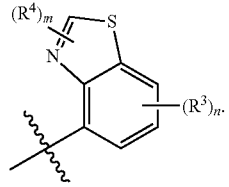
A-1-D

Embodiment 20

A compound of Embodiment 19 wherein A is selected from A-1-A and A-1-B.

Embodiment 21

A compound of Embodiment 20 wherein A is A-1-A.

Embodiment 22

A compound of any one of Embodiments 1 through 12, 14 or 16 wherein A is selected from

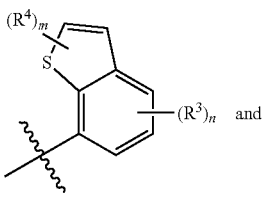

A-2-A

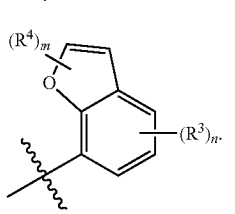

A-2-B

Embodiment 23

A compound of Embodiment 22 wherein A is A-2-A.

Embodiment 24

A compound of any one of Embodiments 19 through 23 wherein
m is 0 or 1; and
n is 0 or 1.

Embodiment 25

A compound of Embodiment 24 wherein
m is 1, located at the position adjacent to the O or S heteroatom; and
n is 1, located at the position adjacent to the attachment point to the remainder of Formula 1.

Embodiment 26

A compound of Embodiment 24 wherein
m is 0; and
n is 1.

Embodiment 27

A compound of Embodiment 24 wherein
m is 1; and
n is 0.

Embodiment 28

A compound of any one of Embodiments 1 through 13, or 17 wherein A is

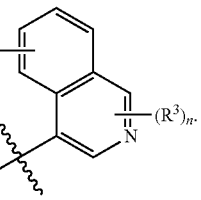

A-3-A

Embodiment 29

A compound of any one of Embodiments 1 through 11, 17 or 18 wherein A is

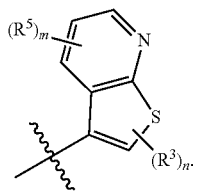

A-4-A

Embodiment 30

A compound of Embodiment 28 or 29 wherein
m is 0 or 1; and
n is 0 or 1.

Embodiment 31

A compound of Embodiment 30 wherein
m is 0; and
n is 1.

Embodiment 32

A compound of Embodiment 30 wherein
m is 1; and
n is 0.

Embodiment 33

A compound of any one of Embodiments 1 through 32 wherein $G^1$ is H, —C(=O)$R^7$, —C(=S)$R^7$, —CO$_2R^8$, —C(=O)S$R^8$, —CONR$^9R^{10}$ or P(=O)$R^{11}$; or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_1$-$C_4$ alkoxyalkyl, $C_3$-$C_6$ cycloalkyl or $C_4$-$C_7$ cycloalkylalkyl.

Embodiment 34

A compound of Embodiment 33 wherein $G^1$ is H, —C(=O)$R^7$, —CO$_2R^8$, —CONR$^9R^{10}$ or P(=O)$R^{11}$; or $C_1$-$C_4$ alkyl, $C_2$-$C_4$ alkenyl, $C_1$-$C_4$ haloalkyl, $C_2$-$C_4$ haloalkenyl, $C_1$-$C_4$ alkoxyalkyl, $C_3$-$C_6$ cycloalkyl or $C_4$-$C_7$ cycloalkylalkyl.

Embodiment 35

A compound of Embodiment 34 wherein $G^1$ is H, —C(=O)$R^7$, —CO$_2R^8$ or P(=O)$R^{11}$; or $C_1$-$C_4$ alkyl, $C_1$-$C_4$ haloalkyl, $C_1$-$C_4$ alkoxyalkyl or $C_3$-$C_6$ cycloalkyl.

Embodiment 36

A compound of Embodiment 35 wherein $G^1$ is H, —C(=O)$R^7$, —CO$_2R^8$; or $C_1$-$C_4$ alkoxyalkyl or $C_3$-$C_6$ cycloalkyl.

Embodiment 37

A compound of Embodiment 36 wherein $G^1$ is H.

Embodiment 38

A compound of Embodiment 36 wherein $G^1$ is —C(=O)$R^7$.

Embodiment 39

A compound of Embodiment 36 wherein $G^1$ is —CO$_2R^8$.

Embodiment 40

A compound of Embodiment 36 wherein $G^1$ is $C_1$-$C_4$ alkoxyalkyl.

Embodiment 41

A compound of Embodiment 36 wherein $G^1$ is $C_3$-$C_6$ cycloalkyl.

Embodiment 42

A compound of any one of Embodiments 1 through 41 wherein G is $G^1$.

Embodiment 43

A compound of any one of Embodiments 1 through 41 wherein G is $W^1G^1$.

Embodiment 44

A compound of Embodiment 43 wherein $W^1$ is $C_1$-$C_2$ alkanediyl or $C_2$-$C_3$ alkenediyl.

Embodiment 45

A compound of Embodiment 44 wherein $W^1$ is —CH$_2$— or —CH=CH—.

Embodiment 46

A compound of Embodiment 45 wherein $W^1$ is —CH$_2$—.

Embodiment 47

A compound of any one of Embodiments 1 through 46 wherein $R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy or $C_1$-$C_5$ alkylthio.

Embodiment 48

A compound of Embodiment 47 wherein $R^2$ is H, halogen, —CN, —CHO, $C_1$-$C_7$ alkyl, $C_1$-$C_4$ alkylcarbonyl, $C_2$-$C_7$ alkylcarbonyloxy, $C_4$-$C_7$ alkylcycloalkyl, $C_1$-$C_4$ alkylsulfinyl, $C_1$-$C_4$ alkylsulfonyl, $C_1$-$C_4$ alkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl or $C_1$-$C_7$ alkoxy.

Embodiment 49

A compound of Embodiment 48 wherein $R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy.

Embodiment 50

A compound of Embodiment 49 wherein $R^2$ is H, halogen, —CN, $C_1$-$C_3$ alkyl, cyclopropyl, $C_1$-$C_2$ haloalkyl, methoxy or ethoxy.

Embodiment 51

A compound of Embodiment 50 wherein $R^2$ is H, Cl, Br, I, —CN, methyl or methoxy.

Embodiment 52

A compound of Embodiment 51 wherein $R^2$ is H, Cl, methyl or methoxy.

Embodiment 53

A compound of Embodiment 52 wherein $R^2$ is Cl or methyl.

Embodiment 54

A compound of any one of Embodiments 1 through 52 wherein $R^2$ is other than H.

Embodiment 55

A compound of any one of Embodiments 1 through 52 wherein $R^2$ is other than phenyl.

Embodiment 56

A compound of any one of Embodiments 1 through 55 wherein each $X^1$ is independently N.

Embodiment 57

A compound of any one of Embodiments 1 through 55 wherein each $X^1$ is independently $CR^3$.

Embodiment 58

A compound of any one of Embodiments 1 through 57 wherein each $X^2$ is independently N.

Embodiment 59

A compound of any one of Embodiments 1 through 57 wherein each $X^2$ is independently $CR^3$.

Embodiment 60

A compound of any one of Embodiments 1 through 59 wherein each $X^3$ is independently N.

Embodiment 61

A compound of any one of Embodiments 1 through 59 wherein each $X^3$ is independently $CR^3$.

Embodiment 62

A compound of any one of Embodiments 1 through 61 wherein each $X^4$ is independently N.

Embodiment 63

A compound of any one of Embodiments 1 through 61 wherein each $X^4$ is independently $CR^4$.

Embodiment 64

A compound of any one of Embodiments 1 through 63 wherein each $X^5$ is independently N.

Embodiment 65

A compound of any one of Embodiments 1 through 63 wherein each $X^5$ is independently $CR^4$.

Embodiment 66

A compound of any one of Embodiments 1 through 65 wherein each $X^6$ is independently N.

Embodiment 67

A compound of any one of Embodiments 1 through 65 wherein each $X^6$ is independently $CR^4$.

Embodiment 68

A compound of any one of Embodiments 1 through 67 wherein $X^7$, $X^8$, $X^9$ and $X^{10}$, are taken together as —CH=CH—CH=CH— (i.e. taken together with the remainder of A-3 or A-4 to form a ring).

Embodiment 69

A compound of any one of Embodiments 1 through 67 wherein $X^7$, $X^8$, $X^9$ and $X^{10}$ are taken together as —N=CH—CH=CH— (i.e. taken together with the remainder of A-3 or A-4 to form a ring).

Embodiment 70

A compound of any one of Embodiments 1 through 67 wherein $X^7$, $X^8$, $X^9$ and $X^{10}$ are taken together as —C(CH$_3$)=CH—CH=CH— (i.e. taken together with the remainder of A-3 or A-4 to form a ring).

Embodiment 71

A compound of any one of Embodiments 1 through 67 wherein $X^7$, $X^8$, $X^9$ and $X^{10}$ are taken together as —CH=CH—N=CH— (i.e. taken together with the remainder of A-3 or A-4 to form a ring).

Embodiment 72

A compound of any one of Embodiments 1 through 67 wherein $X^7$, $X^8$, $X^9$ and $X^{10}$ are taken together as —CH=CH—C(CH$_3$)=CH— (i.e. taken together with the remainder of A-3 or A-4 to form a ring).

Embodiment 73

A compound of any one of Embodiments 1 through 72 wherein $Y^1$ is O or S.

Embodiment 74

A compound of Embodiment 73 wherein $Y^1$ is O.

Embodiment 75

A compound of Embodiment 73 wherein $Y^1$ is S.

Embodiment 76

A compound of any one of Embodiments 1 through 72 wherein $Y^2$ is O or S.

Embodiment 77

A compound of Embodiment 76 wherein $Y^2$ is O.

Embodiment 78

A compound of Embodiment 76 wherein $Y^2$ is S.

Embodiment 79

A compound of any one of Embodiments 1 through 72 wherein $Y^4$ is O or S.

Embodiment 80

A compound of Embodiment 79 wherein $Y^4$ is O.

Embodiment 81

A compound of Embodiment 79 wherein $Y^4$ is S.

Embodiment 82

A compound of Formula 1 or any one of Embodiments 1 through 81 wherein each $R^3$ is independently H, halogen, $C_1$-$C_3$ alkyl, $C_3$-$C_4$ cycloalkyl, $C_1$-$C_3$ haloalkyl or $C_1$-$C_3$ alkoxy.

Embodiment 83

A compound of Embodiment 82 wherein each $R^3$ is independently H, halogen, $C_1$-$C_2$ alkyl, cyclopropyl or $C_1$-$C_2$ haloalkyl.

Embodiment 84

A compound of Embodiment 83 wherein each $R^3$ is independently H, halogen, methyl, ethyl or CF$_3$.

Embodiment 85

A compound of Embodiment 84 wherein each $R^3$ is independently H, F, Cl, Br or methyl.

Embodiment 86

A compound of Embodiment 85 wherein each $R^3$ is independently H.

Embodiment 87

A compound of any one of Embodiments 1 through 86 wherein each $R^4$ is independently H, halogen, $C_1$-$C_3$ alkyl, $C_3$-$C_4$ cycloalkyl, $C_1$-$C_3$ haloalkyl or $C_1$-$C_3$ alkoxy.

Embodiment 88

A compound of Embodiment 87 wherein each $R^4$ is independently H, halogen, $C_1$-$C_2$ alkyl, cyclopropyl or $C_1$-$C_2$ haloalkyl.

Embodiment 89

A compound of Embodiment 88 wherein each $R^4$ is independently H, halogen, methyl, ethyl or $CF_3$.

Embodiment 90

A compound of Embodiment 89 wherein each $R^4$ is independently H, methyl or ethyl.

Embodiment 91

A compound of Embodiment 90 wherein $R^4$ is methyl.

Embodiment 92

A compound of any one of Embodiments 1 through 86 wherein each $R^5$ is independently H, halogen, $C_1$-$C_3$ alkyl, $C_3$-$C_4$ cycloalkyl, $C_1$-$C_3$ haloalkyl or $C_1$-$C_3$ alkoxy.

Embodiment 93

A compound of Embodiment 92 wherein each $R^5$ is independently H, halogen, $C_1$-$C_2$ alkyl, cyclopropyl or $C_1$-$C_2$ haloalkyl.

Embodiment 94

A compound of Embodiment 93 wherein each $R^5$ is independently H, halogen, methyl, ethyl or $CF_3$.

Embodiment 95

A compound of Embodiment 94 wherein each $R^5$ is independently H, methyl or ethyl.

Embodiment 96

A compound of Embodiment 95 wherein $R^5$ is H.

Embodiment 97

A compound of any one of Embodiments 1 through 96 wherein $R^6$ is H or $C_1$-$C_3$ alkyl.

Embodiment 98

A compound of Embodiment 97 wherein $R^6$ is H or $CH_3$.

Embodiment 99

A compound of Embodiment 98 wherein $R^6$ is $CH_3$.

Embodiment 100

A compound of any one of Embodiments 1 through 99 wherein $R^7$ is H, $C_1$-$C_7$ alkyl, $C_3$-$C_7$ cycloalkyl, $C_1$-$C_3$ haloalkyl or $C_2$-$C_7$ alkoxyalkyl.

Embodiment 101

A compound of Embodiment 100 wherein $R^7$ is H, $C_1$-$C_7$ alkyl, $C_3$-$C_7$ cycloalkyl or $C_2$-$C_7$ alkoxyalkyl.

Embodiment 102

A compound of Embodiment 101 wherein $R^7$ is $C_1$-$C_7$ alkyl or $C_2$-$C_7$ alkoxyalkyl.

Embodiment 103

A compound of Embodiment 102 wherein $R^7$ is independently $C_1$-$C_3$ alkyl or $C_2$-$C_4$ alkoxyalkyl.

Embodiment 104

A compound of any one of Embodiments 1 through 99 wherein $R^8$ is H, $C_1$-$C_7$ alkyl, $C_3$-$C_7$ cycloalkyl, $C_1$-$C_3$ haloalkyl or $C_2$-$C_7$ alkoxyalkyl.

Embodiment 105

A compound of Embodiment 104 wherein $R^8$ is H, $C_1$-$C_7$ alkyl, $C_3$-$C_7$ cycloalkyl or $C_2$-$C_7$ alkoxyalkyl.

Embodiment 106

A compound of Embodiment 105 wherein $R^8$ is $C_1$-$C_7$ alkyl or $C_2$-$C_7$ alkoxyalkyl.

Embodiment 107

A compound of Embodiment 106 wherein $R^8$ is $C_1$-$C_3$ alkyl or $C_2$-$C_4$ alkoxyalkyl.

Embodiment 108

A compound of any one of Embodiments 1 through 99 wherein $R^9$ is H, $C_1$-$C_7$ alkyl, $C_3$-$C_7$ cycloalkyl, $C_2$-$C_3$ haloalkyl or $C_2$-$C_7$ alkoxyalkyl.

Embodiment 109

A compound of Embodiment 108 wherein $R^9$ is H, $C_1$-$C_7$ alkyl, $C_3$-$C_7$ cycloalkyl or $C_2$-$C_7$ alkoxyalkyl.

Embodiment 110

A compound of Embodiment 109 wherein $R^9$ is $C_1$-$C_7$ alkyl or $C_2$-$C_7$ alkoxyalkyl.

Embodiment 111

A compound of any one of Embodiments 1 through 99 wherein $R^{10}$ is H, $C_1$-$C_7$ alkyl, $C_3$-$C_7$ cycloalkyl, $C_1$-$C_3$ haloalkyl or $C_2$-$C_7$ alkoxyalkyl.

Embodiment 112

A compound of Embodiment 111 wherein $R^{10}$ is H, $C_1$-$C_7$ alkyl, $C_3$-$C_7$ cycloalkyl or $C_2$-$C_7$ alkoxyalkyl.

Embodiment 113

A compound of any one of Embodiments 1 through 99 wherein $R^{11}$ is $C_1$-$C_3$ alkyl or $C_1$-$C_3$ alkoxy.

Embodiment 114

A compound of Embodiment 113 wherein $R^{11}$ is $CH_3$ or $OCH_3$.

Embodiment 115

A compound of Embodiment 114 wherein $R^{11}OCH_3$.

Embodiment 116

A compound of Formula 1 wherein when A is A-1, $R^1$ is $CH_3$, $R^2$ is $CH_3$, G is $G^1$, $G^1$ is H, $X^1$ is CBr, $X^2$ and $X^3$ are both CH, $X^5$ is N, $X^6$ is N then $Y^1$ is other than N—$CH_3$.

Embodiment 117

A compound of Formula 1 wherein when A is A-1, $R^1$ is $CH_3$, $R^2$ is Cl, G is $G^1$, $G^1$ is H, each $X^1$, $X^2$ and $X^3$ is CH, $X^5$ is N, $X^6$ is N, then $Y^1$ is other than N—$CH_3$.

Embodiment 118

A compound of Formula 1 wherein when A is A-1, $R^1$ is $CH_3$, $R^2$ is $CH_3$, G is $G^1$, $G^1$ is —C(=O)$R^7$, $R^7$ is phenyl, $X^1$, $X^2$ are both CH, $X^3$ is CCl, $X^5$ is $CCH_3$, $X^6$ is CH then $Y^1$ is other than O.

Embodiment 119

A compound of Formula 1 wherein when A is A-1, $R^1$ is $CH_3$, $R^2$ is Cl, G is $G^1$, $G^1$ is H, $X^1$, $X^2$, $X^3$ is CH, $X^5$ is N, $X^6$ is N then $Y^1$ other than N—$CH_3$.

Embodiment 120

A compound of Formula 1 wherein when A is A-3, $R^1$ is $CH_3$, $R^2$ is H, G is $G^1$, $G^1$ is H, each $X^1$, $X^2$, $X^3$, $X^7$, $X^9$ and $X^{10}$ is CH, then $X^8$ is other than N.

Embodiment 121

A compound of Embodiment 47 wherein $R^2$ is halogen, $C_1$-$C_7$ alkyl, $C_1$-$C_4$ alkylamino, $C_2$-$C_8$ dialkylamino or $C_3$-$C_7$ cycloalkyl.

Embodiment 122

A compound of Embodiment 121 wherein $R^2$ is $C_1$-$C_4$ alkylamino, or $C_2$-$C_8$ dialkylamino.

Embodiment 123

A compound of any one of Embodiments 1 through 13, or 17 wherein A is

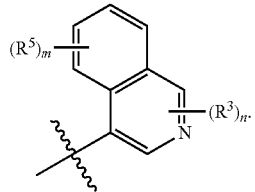

A-3-A

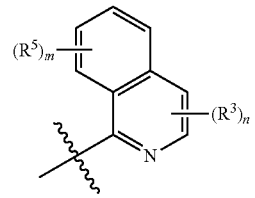

A-3-B

Embodiment 124

A compound of any one of Embodiments 1 through 11 wherein A is A-1, A-2 or A-4.

Embodiment 125

A compound of Formula 1 wherein when A is A-4; $Y^4$ is O, S or $NR^6$; and $R^6$ is other than H, $C_1$-$C_3$ alkyl or $C_1$-$C_3$ haloalkyl; then at least one of $X^7$, $X^8$, $X^9$ and $X^{10}$ is other than $CR^5$.

Embodiment 126

A compound of Formula 1 wherein when A is A-3; $R^1$ is $CH_3$; G is H or C(=O)$CH_3$; $R^2$ is Cl or Br, then each $X^2$ and $X^3$ is independently $CR^3$; and each $X^7$, $X^8$ and $X^9$ is independently $CR^5$.

Embodiment 127

A compound of Formula 1 wherein when A is A-3; $R^1$ is $CH_3$; G is H or C(=O)$CH_3$; $R^2$ is Cl or Br; and any one of $X^2$, $X^3$, $X^7$, $X^8$ or $X^9$ is N, then a second $X^2$, $X^3$, $X^7$, $X^8$ or $X^9$ is N or $CR^3$ and $R^3$ is other than H.

Embodiments of this invention, including Embodiments 1-127 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-127 above as well as any other embodiments described herein, and any combination thereof, pertain to the compositions and methods of the present invention.

Embodiment A

A compound of Formula 1, N-oxides and salts thereof, compositions containing them, and methods of their use for controlling undesired vegetation wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl;
W is O;
A is A-1, A-2 or A-3;
$G^1$ is H, —C(=O)$R^7$, —C(=S)$R^7$, —CO$_2R^8$, —C(=O)S$R^8$, —CONR$^9R^{10}$ or P(=O)$R^{11}$; or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_1$-$C_4$ alkoxyalkyl, $C_3$-$C_6$ cycloalkyl or $C_4$-$C_7$ cycloalkylalkyl;
$W^1$ is $C_1$-$C_2$ alkenediyl or $C_2$-$C_3$ alkenediyl;
$R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy or $C_1$-$C_5$ alkylthio;
each $X^1$ is independently $CR^3$;
each $R^3$ is independently H, halogen, $C_1$-$C_3$ alkyl, $C_3$-$C_4$ cycloalkyl, $C_1$-$C_3$ haloalkyl or $C_1$-$C_3$ alkoxy;
each $R^4$ is independently H, halogen, $C_1$-$C_3$ alkyl, $C_3$-$C_4$ cycloalkyl, $C_1$-$C_3$ haloalkyl or $C_1$-$C_3$ alkoxy;
each $R^5$ is independently H, halogen, $C_1$-$C_3$ alkyl, $C_3$-$C_4$ cycloalkyl, $C_1$-$C_3$ haloalkyl or $C_1$-$C_3$ alkoxy;
$R^6$ is H or $C_1$-$C_3$ alkyl;
$R^7$ is H, $C_1$-$C_7$ alkyl, $C_3$-$C_7$ cycloalkyl, $C_1$-$C_3$ haloalkyl or $C_2$-$C_7$ alkoxyalkyl;
$R^8$ is H, $C_1$-$C_7$ alkyl, $C_3$-$C_7$ cycloalkyl, $C_1$-$C_3$ haloalkyl or $C_2$-$C_7$ alkoxyalkyl;
$R^9$ is H, $C_1$-$C_7$ alkyl, $C_3$-$C_7$ cycloalkyl, $C_2$-$C_3$ haloalkyl or $C_2$-$C_7$ alkoxyalkyl;
$R^{10}$ is H, $C_1$-$C_7$ alkyl, $C_3$-$C_7$ cycloalkyl, $C_1$-$C_3$ haloalkyl or $C_2$-$C_7$ alkoxyalkyl; and
$R^{11}$ is $C_1$-$C_3$ alkyl or $C_1$-$C_3$ alkoxy.

Embodiment B

A compound of Embodiment A wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl;
A is A-1 or A-2;
$G^1$ is H, —C(=O)$R^7$, —CO$_2R^8$, —CONR$^9R^{10}$ or P(=O)$R^{11}$; or $C_1$-$C_4$ alkyl, $C_2$-$C_4$ alkenyl, $C_1$-$C_4$ haloalkyl, $C_2$-$C_4$ haloalkenyl, $C_1$-$C_4$ alkoxyalkyl, $C_3$-$C_6$ cycloalkyl or $C_4$-$C_7$ cycloalkylalkyl;
$W^1$ is —CH$_2$— or —CH=CH—;
$R^2$ is H, halogen, —CN, —CHO, $C_1$-$C_7$ alkyl, $C_1$-$C_4$ alkylcarbonyl, $C_2$-$C_7$ alkylcarbonyloxy, $C_4$-$C_7$ alkylcycloalkyl, $C_1$-$C_4$ alkylsulfinyl, $C_1$-$C_4$ alkylsulfonyl, $C_1$-$C_4$ alkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl or $C_1$-$C_7$ alkoxy;
each $X^2$ is independently $CR^3$;
each $X^5$ is independently $CR^4$;
$Y^1$ is O or S;
$Y^2$ is O or S;
each $R^3$ is independently H, halogen, $C_1$-$C_2$ alkyl, cyclopropyl or $C_1$-$C_2$ haloalkyl;
each $R^4$ is independently H, halogen, $C_1$-$C_2$ alkyl, cyclopropyl or $C_1$-$C_2$ haloalkyl;

$R^7$ is H, $C_1$-$C_7$ alkyl, $C_3$-$C_7$ cycloalkyl or $C_2$-$C_7$ alkoxyalkyl;
$R^8$ is H, $C_1$-$C_7$ alkyl, $C_3$-$C_7$ cycloalkyl or $C_2$-$C_7$ alkoxyalkyl;
$R^9$ is H, $C_1$-$C_7$ alkyl, $C_3$-$C_7$ cycloalkyl or $C_2$-$C_7$ alkoxyalkyl;
$R^{10}$ is H, $C_1$-$C_7$ alkyl, $C_3$-$C_7$ cycloalkyl or $C_2$-$C_7$ alkoxyalkyl; and
$R^{11}$ is CH$_3$ or OCH$_3$.

Embodiment C

A compound of Embodiment B wherein
$R^1$ is $C_1$-$C_4$ alkyl, $C_3$-$C_4$ cycloalkyl, $C_2$-$C_3$ cyanoalkyl, $C_1$-$C_3$ haloalkyl or $C_2$-$C_4$ alkoxyalkyl;
A is selected from

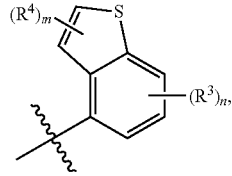

A-1-A

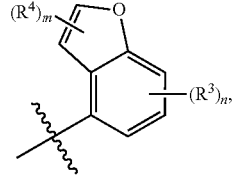

A-1-B

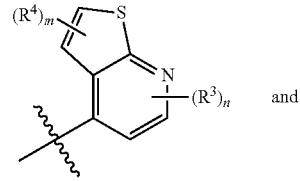

A-1-C and

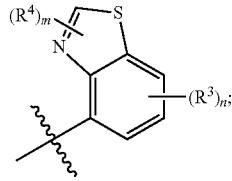

A-1-D $G^1$ is H, —C(=O)$R^7$, —CO$_2R^8$ or P(=O)$R^{11}$; or $C_1$-$C_4$ alkyl, $C_1$-$C_4$ haloalkyl, $C_1$-$C_4$ alkoxyalkyl or $C_3$-$C_6$ cycloalkyl;
$W^1$ is —CH$_2$—;
$R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy;
each $R^3$ is independently H, halogen, methyl, ethyl or CF$_3$;
each $R^4$ is independently H, halogen, methyl, ethyl or CF$_3$;
$R^7$ is $C_1$-$C_7$ alkyl or $C_2$-$C_7$ alkoxyalkyl;
$R^8$ is $C_1$-$C_7$ alkyl or $C_2$-$C_7$ alkoxyalkyl; and
$R^{11}$ is OCH$_3$.

Embodiment D

A compound of Embodiment C wherein
$R^1$ is methyl, ethyl, n-propyl or 2-methoxyethyl;

A is selected from A-1-A and A-1-B;
G is $G^1$;
$G^1$ is H, —C(=O)$R^7$, —CO$_2R^8$; or $C_1$-$C_4$ alkoxyalkyl or $C_3$-$C_6$ cycloalkyl;
$R^2$ is H, Cl, Br, I, —CN, methyl or methoxy;
each $R^3$ is independently H, F, Cl, Br or methyl;
each $R^4$ is independently H, methyl or ethyl;
$R^7$ is $C_1$-$C_3$ alkyl or $C_2$-$C_4$ alkoxyalkyl; and
$R^8$ is $C_1$-$C_3$ alkyl or $C_2$-$C_4$ alkoxyalkyl.

Embodiment E

A compound of Embodiment B wherein
$R^1$ is $C_1$-$C_4$ alkyl, $C_3$-$C_4$ cycloalkyl, $C_2$-$C_3$ cyanoalkyl, $C_1$-$C_3$ haloalkyl or $C_2$-$C_4$ alkoxyalkyl;
A is selected from

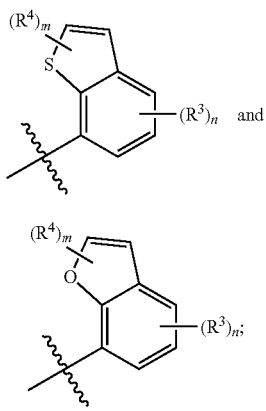

$G^1$ is H, —C(=O)$R^7$, —CO$_2R^8$ or P(=O)$R^{11}$; or $C_1$-$C_4$ alkyl, $C_1$-$C_4$ haloalkyl, $C_1$-$C_4$ alkoxyalkyl or $C_3$-$C_6$ cycloalkyl;
$W^1$ is —CH$_2$—;
$R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy;
each $R^3$ is independently H, halogen, methyl, ethyl or CF$_3$;
each $R^4$ is independently H, halogen, methyl, ethyl or CF$_3$;
$R^7$ is $C_1$-$C_7$ alkyl or $C_2$-$C_7$ alkoxyalkyl;
$R^8$ is $C_1$-$C_7$ alkyl or $C_2$-$C_7$ alkoxyalkyl; and
$R^{11}$ is OCH$_3$.

Embodiment F

A compound of Embodiment E wherein
$R^1$ is methyl, ethyl, n-propyl or 2-methoxyethyl;
A is A-2-A;
G is $G^1$;
$G^1$ is H, —C(=O)$R^7$, —CO$_2R^8$; or $C_1$-$C_4$ alkoxyalkyl or $C_3$-$C_6$ cycloalkyl;
$R^2$ is H, Cl, Br, I, —CN, methyl or methoxy;
each $R^3$ is independently H, F, Cl, Br or methyl;
each $R^4$ is independently H, methyl or ethyl;
$R^7$ is $C_1$-$C_3$ alkyl or $C_2$-$C_4$ alkoxyalkyl; and
$R^8$ is $C_1$-$C_3$ alkyl or $C_2$-$C_4$ alkoxyalkyl.
Specific embodiments include compounds of Formula 1 selected from the group consisting of:
4-(2,6-dimethyl-7-benzofuranyl)-5-hydroxy-2,6-dimethyl-3 (2H)-pyridazinone (Compound 10);
5-(acetyloxy)-4-(2,6-dimethyl-7-benzofuranyl)-2,6-dimethyl-3(2H)-pyridazinone (Compound 11);
5-hydroxy-2,6-dimethyl-4-(3-methyl-1,2-benzisothiazol-4-yl)-3 (2H)-pyridazinone (Compound 25);
5-hydroxy-2,6-dimethyl-4-(5-methylbenzo[b]thien-4-yl)-3 (2H)-pyridazinone (Compound 29); and
1,6-dihydro-1,3-dimethyl-5-(5-methylbenzo[b]thien-4-yl)-6-oxo-4-pyridazinyl ethyl carbonate (Compound 30).
Specific embodiments include compounds of Formula 1 selected from the group consisting of:
4-(2,6-dimethyl-7-benzofuranyl)-5-hydroxy-2,6-dimethyl-3 (2H)-pyridazinone (Compound 10);
5-(acetyloxy)-4-(2,6-dimethyl-7-benzofuranyl)-2,6-dimethyl-3(2H)-pyridazinone (Compound 11); and
5-hydroxy-2,6-dimethyl-4-(3-methyl-1,2-benzisothiazol-4-yl)-3 (2H)-pyridazinone (Compound 25).
A specific embodiment of the present invention is a compound of Formula 1 that is:
4-(2,6-dimethyl-7-benzofuranyl)-5-hydroxy-2,6-dimethyl-3 (2H)-pyridazinone (Compound 10).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, de smetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-s odium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzene sulfonamide), me so sulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuronmethyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethane sulfonamide), triasulfuron, tribe nuronmethyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimehyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1 (2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, naprop amide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3 (2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include cyclopyrimorate (6-chloro-3-(2-cyclopropyl-6-methylphenoxy)-4-pyridazinyl 4-morpholinecarboxylate), haloxydine, pyriclor, 3-(2-chloro-3,6-difluorophenyl)-4-hydroxy-1-methyl-1,5-naphthyridin-2 (1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

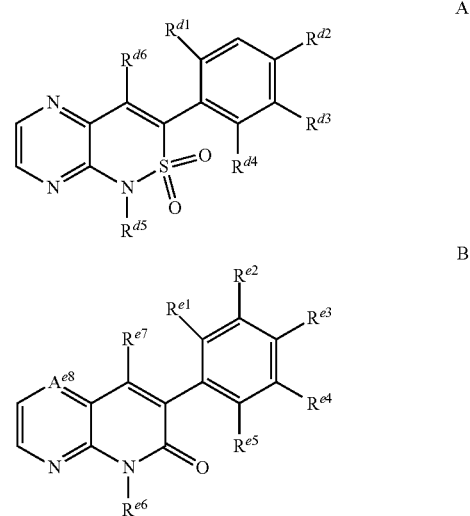

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Other herbicides" (b15) also include a compound of Formula (b15A)

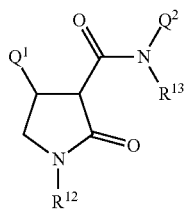

(b15A)

wherein

R[12] is H, $C_1$-$C_6$ alkyl, $C_1$-$C_6$ haloalkyl or $C_4$-$C_8$ cycloalkyl;

R[13] is H, $C_1$-$C_6$ alkyl or $C_1$-$C_6$ alkoxy;

$Q^1$ is an optionally substituted ring system selected from the group consisting of phenyl, thienyl, pyridinyl, benzodioxolyl, naphthyl, naphthalenyl, benzofuranyl, furanyl, benzothiophenyl and pyrazolyl, wherein when substituted said ring system is substituted by 1 to 3 R[14];

$Q^2$ is an optionally substituted ring system selected from the group consisting of phenyl, pyridinyl, benzodioxolyl, pyridinonyl, thiadiazolyl, thiazolyl, and oxazolyl, wherein when substituted said ring system is substituted by 1 to 3 R[15];

each R[14] is independently halogen, $C_1$-$C_6$ alkyl, $C_1$-$C_6$ haloalkyl, $C_1$-$C_6$ alkoxy, $C_1$-$C_6$ haloalkoxy, $C_3$-$C_8$ cyaloalkyl, cyano, $C_1$-$C_6$ alkylthio, $C_1$-$C_6$ alkylsulfinyl, $C_1$-$C_6$ alkylsulfonyl, $SF_5$, NHR[17]; or phenyl optionally substituted by 1 to 3 R[16]; or pyrazolyl optionally substituted by 1 to 3 R[16];

each R[15] is independently halogen, $C_1$-$C_6$ alkyl, $C_1$-$C_6$ haloalkyl, $C_1$-$C_6$ alkoxy, $C_1$-$C_6$ haloalkoxy, cyano, nitro, $C_1$-$C_6$ alkylthio, $C_1$-$C_6$ alkylsulfinyl, $C_1$-$C_6$ alkylsulfonyl;

each R[16] is independently halogen, $C_1$-$C_6$ alkyl or $C_1$-$C_6$ haloalkyl;

R[17] is $C_1$-$C_4$ alkoxycarbonyl.

In one Embodiment wherein "other herbicides" (b15) also include a compound of Formula (b15A), it is preferred that R[12] is H or $C_1$-$C_6$ alkyl; more preferably R[12] is H or methyl. Preferably R[13] is H. Preferably $Q^1$ is either a phenyl ring or a pyridinyl ring, each ring substituted by 1 to 3 R[14]; more preferably $Q^1$ is a phenyl ring substituted by 1 to 2 R[14]. Preferably $Q^2$ is a phenyl ring substituted by 1 to 3 R[15]; more preferably $Q^2$ is a phenyl ring substituted by 1 to 2 R[15]. Preferably each R[14] is independently halogen, $C_1$-$C_4$ alkyl, $C_1$-$C_3$ haloalkyl, $C_1$-$C_3$ alkoxy or $C_1$-$C_3$ haloalkoxy; more preferably each R[14] is independently chloro, fluoro, bromo, $C_1$-$C_2$ haloalkyl, $C_1$-$C_2$ haloalkoxy or $C_1$-$C_2$ alkoxy. Preferably each R[15] is independently halogen, $C_1$-$C_4$ alkyl, $C_1$-$C_3$ haloalkoxy; more preferably each R[15] is independently chloro, fluoro, bromo, $C_1$-$C_2$ haloalkyl, $C_1$-$C_2$ haloalkoxy or $C_1$-$C_2$ alkoxy. Specifically preferred as "other herbicides" (b15) include any one of the following (b15A-1) through (b15A-15):

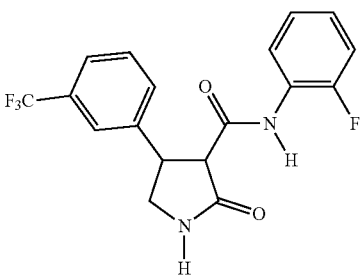

(b15A-1)

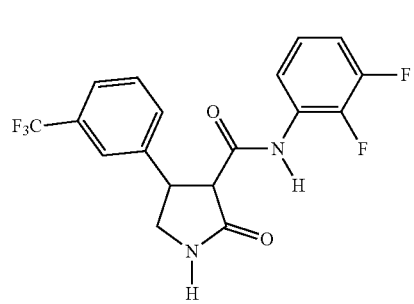

(b15A-2)

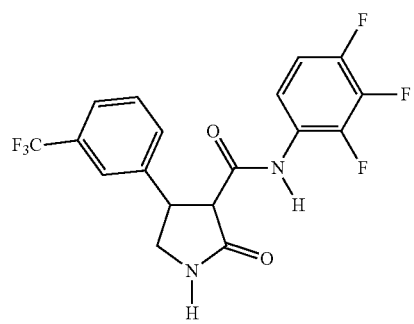

(b15A-3)

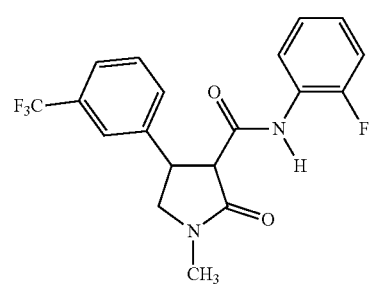

(b15A-4)

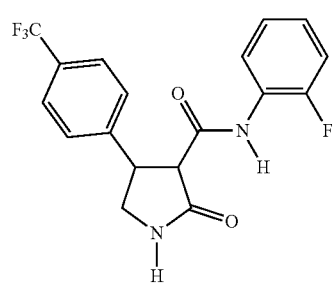

(b15A-5)

-continued
(b15A-6)
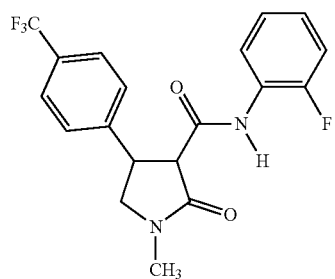
(b15A-7)
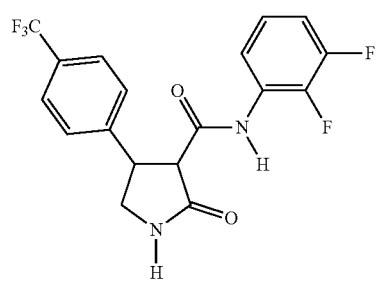
(b15A-8)
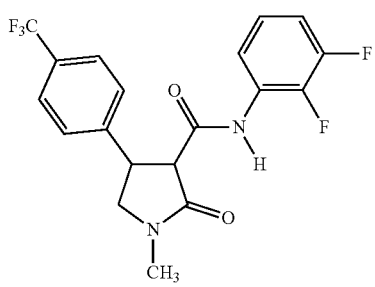
(b15A-9)
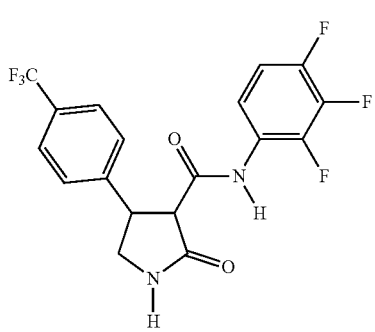
(b15A-10)
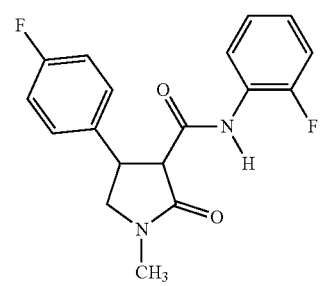
-continued
(b15A-11)
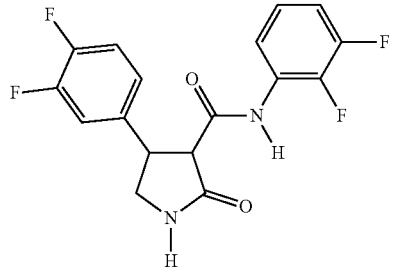
(b15A-12)
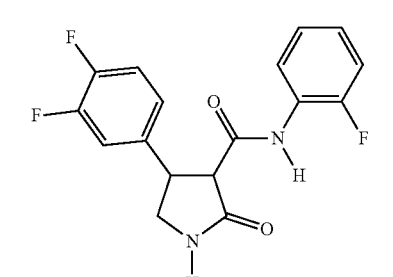
(b15A-13)
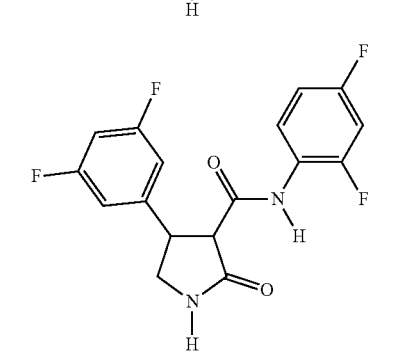
(b15A-14)
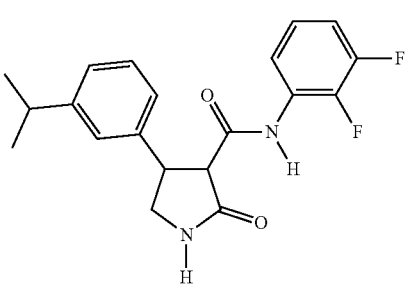
(b15A-15)
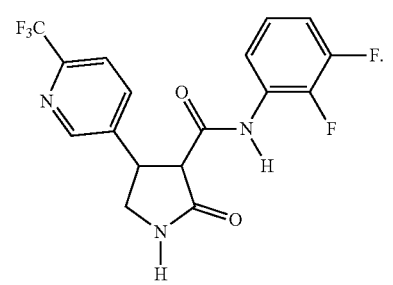

"Other herbicides" (b15) also include a compound of Formula (b15B)

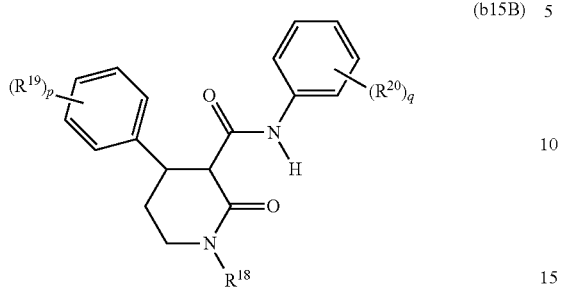
(b15B)

wherein
$R^{18}$ is H, $C_1$-$C_6$ alkyl, $C_1$-$C_6$ haloalkyl or $C_4$-$C_8$ cycloalkyl;
each $R^{19}$ is independently halogen, $C_1$-$C_6$ haloalkyl or $C_1$-$C_6$ haloalkoxy;
p is an integer of 0, 1, 2 or 3;
each $R^{20}$ is independently halogen, $C_1$-$C_6$ haloalkyl or $C_1$-$C_6$ haloalkoxy; and
q is an integer of 0, 1, 2 or 3.

In one Embodiment wherein "other herbicides" (b15) also include a compound of Formula (b15B), it is preferred that $R^{18}$ is H, methyl, ethyl or propyl; more preferably $R^{18}$ is H or methyl; most preferably $R^{18}$ is H. Preferably each $R^{19}$ is independently chloro, fluoro, $C_1$-$C_3$ haloalkyl or $C_1$-$C_3$ haloalkoxy; more preferably each $R^{19}$ is independently chloro, fluoro, $C_1$ fluoroalkyl (i.e. fluoromethyl, difluoromethyl or trifluoromethyl) or $C_1$ fluoroalkoxy (i.e. trifluoromethoxy, difluoromethoxy or fluoromethoxy). Preferably each $R^{20}$ is independently chloro, fluoro, $C_1$ haloalkyl or $C_1$ haloalkoxy; more preferably each $R^{20}$ is independently chloro, fluoro, $C_1$ fluoroalkyl (i.e. fluoromethyl, difluororm-ethyl or trifluromethyl) or $C_1$ fluoroalkoxy (i.e. trifluoromethoxy, difluoromethoxy or fluoromethoxy). Specifically preferred as "other herbicides" (b15) include any one of the following (b15B-1) through (b15B-19):

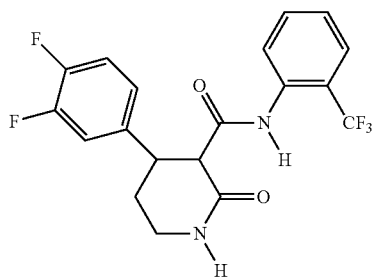
(b15B-1)

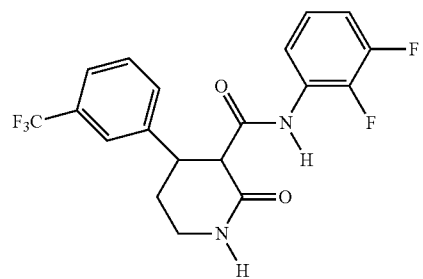
(b15B-2)

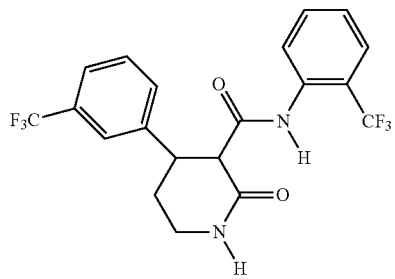
(b15B-3)

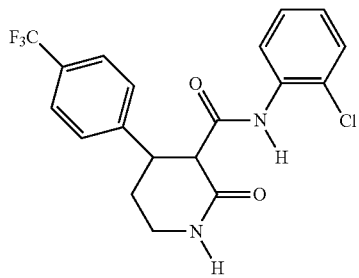
(b15B-4)

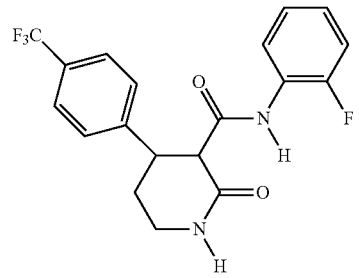
(b15B-5)

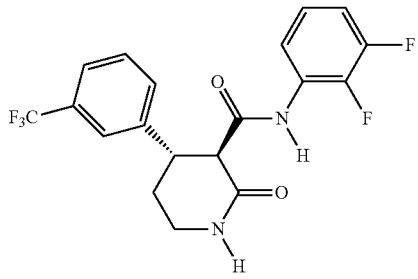
(b15B-6)

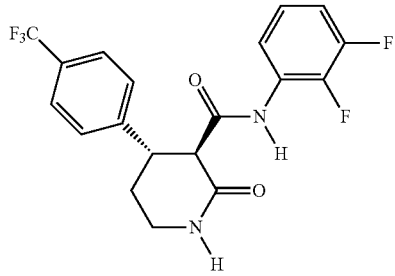
(b15B-7)

(b15B-8)
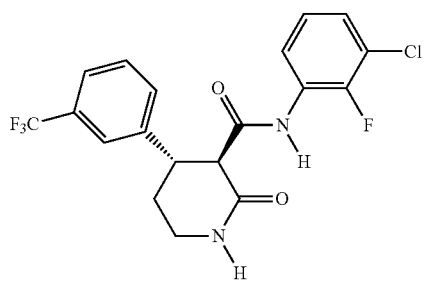
(b15B-13)
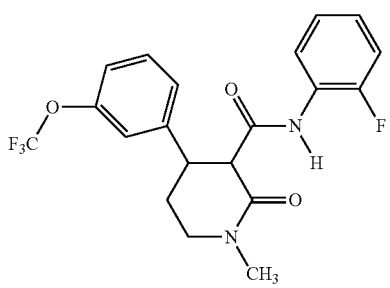
(b15B-9)
(b15B-14)
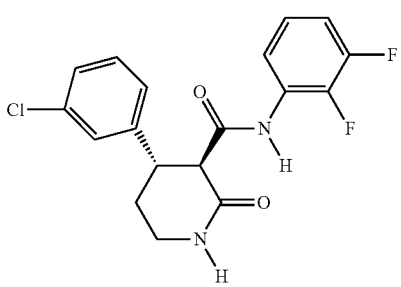
(b15B-10)
(b15B-15)
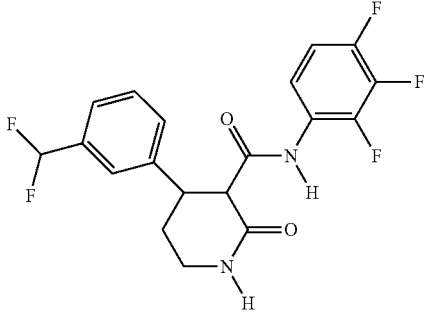
(b15B-11)
(b15B-16)
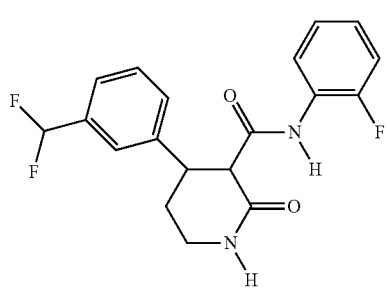
(b15B-12)
(b15B-17)
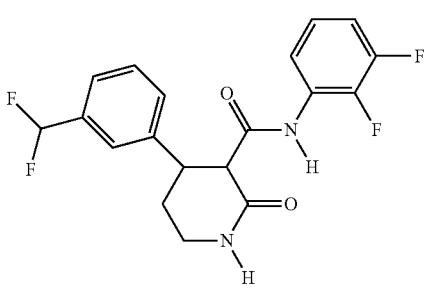

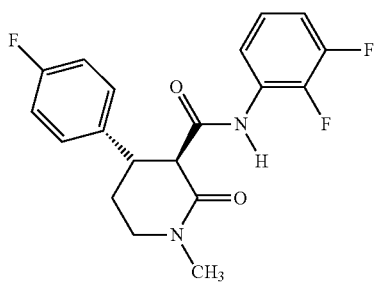

(b15B-18)

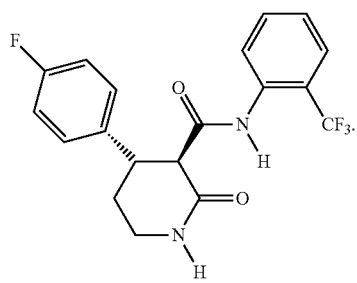

(b15B-19)

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzene sulfonamide and N-(aminocarbonyl)-2-fluorobenzene sulfonamide, 1-bromo-4-[(chloromethyl) sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl] sulfonyl]-benzamide.

One or more of the following methods and variations as described in Schemes 1-25 can be used to prepare compounds of Formula 1. The definitions of groups $R^1$, $R^2$, $R^3$, $R^4$, W, X and G in the compounds of Formulae 1-42 are as defined above in the Summary of the Invention unless otherwise noted. Formulae 1a, 1b and 1c are subsets of compounds of Formula 1, and all substituents for Formulae 1a, 1b and 1c are as defined above for Formula 1 unless otherwise noted. Formulae 6a, 6b and 6c are subsets of compounds of Formula 6, and all substituents for Formulae 6a, 6b and 6c are as defined for Formula 6 unless otherwise noted. Formulae 31a and 31b are subsets of compounds of Formula 31, and all substituents for Formulae 31a and 31b are as defined above for Formula 31 unless otherwise noted.

As shown in Scheme 1, pyridazinones of Formula 1a (a subset of compounds of Formula 1 where W is O, and G is as defined above, but other than hydrogen) can be made by reacting substituted 5-hydroxy-3(2H)-pyridazinones of Formula 1b (i.e. Formula 1 wherein W is O and G is H) with a suitable electrophilic reagent of Formula 2 (i.e. $Z^1$-G where $Z^1$ is a leaving group, alternatively known as a nucleofuge, such as a halogen) in the presence of base in an appropriate solvent. Some examples of reagent classes representing Formula 2 wherein $Z^1$ is Cl include acid chlorides (G is —(C=O)$R^7$), chloroformates (G is —CO$_2R^8$), carbamoyl chlorides (G is —CONR$^9R^{10}$), sulfonyl chlorides (G is —S(O)$_2R^7$) and chlorosulfonamides (G is —S(O)$_2$NR$^9$R$^{10}$) \. Examples of suitable bases for this reaction include, but are not limited to, potassium carbonate, sodium hydroxide, potassium hydroxide, sodium hydride or potassium tert-butoxide and, depending on the specific base used, appropriate solvents can be protic or aprotic and used anhydrous or as aqueous mixtures. Preferred solvents for this reaction include acetonitrile, methanol, ethanol, tetrahydrofuran, diethyl ether, 1,2-dimethoxyethane, dioxane, dichloromethane or N,N-dimethylformamide. The reaction can be run under a range of temperatures, with temperatures typically ranging from 0° C. to the reflux temperature of the solvent.

Scheme 1

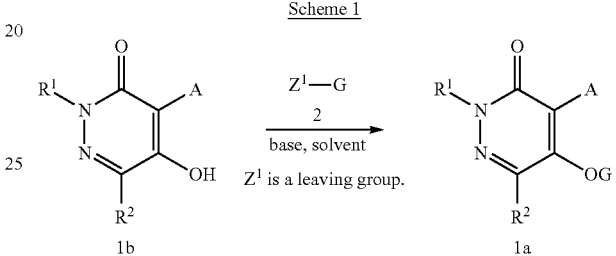

G is as defined for Formula 1, other than H.

Substituted 5-hydroxy-3(2H)-pyridazinones of Formula 1b can be prepared as outlined in Scheme 2 by cyclization of hydrazide esters of Formula 3 (where $R^{30}$ is alkyl, typically methyl or ethyl) in the presence of base and solvent. Suitable bases for this reaction include but are not limited to potassium carbonate, sodium hydroxide, potassium hydroxide, sodium hydride, potassium t-butoxide or 1,8-diazabicyclo[5.4.0]undec-7-ene. Depending on the specific base used, appropriate solvents can be protic or aprotic and used anhydrous or as aqueous mixtures. Solvents for this cyclization include acetonitrile, methanol, ethanol, tetrahydrofuran, diethyl ether, dioxane, 1,2-dimethoxyethane, dichloromethane or N,N-dimethylformamide. Temperatures for this cyclization generally range from 0° C. to the reflux temperature of the solvent. Literature methods for cyclizing hydrazide ester intermediates of formula CH$_3$(CO$_2$C$_2$H$_5$) C=NNCH$_3$C(=O)CH$_2$Ar (where Ar is a substituted phenyl instead of the bicyclic ring system shown in Formula 3) to the corresponding 4-aryl-5-hydroxy-pyridazinones are disclosed in U.S. Pat. Nos. 8,541,414 and 8,470,738. The same conditions reported in these patents are applicable to cyclizing hydrazone esters of Formula 3 to pyridazinones of Formula 1b. The method of Scheme 2 is illustrated by Step G of Synthesis Example 3.

Scheme 2

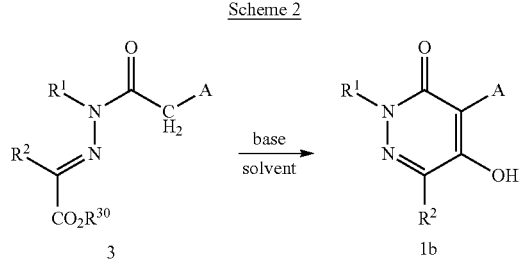

Substituted hydrazide esters of Formula 3 can be prepared as outlined in Scheme 3 by coupling a hydrazone ester of Formula 4 (where $R^{30}$ is alkyl, typically methyl or ethyl) with an acid chloride of Formula 5 in the presence of base and solvent. Preferred bases for this reaction are usually tertiary amines such as triethylamine or Hunig's base, but other bases can also be used, including N,N-dimethylaminopyridine, potassium carbonate, sodium hydroxide, potassium hydroxide, sodium hydride or potassium t-butoxide. Depending on the specific base used, appropriate solvents can be protic or aprotic where the reaction takes place under anhydrous conditions or as aqueous mixtures under Schotten-Baumann conditions. Solvents that are used for this acylation on nitrogen include acetonitrile, tetrahydrofuran, diethyl ether, dioxane, toluene, 1,2-dimethoxyethane, dichloromethane or N,N-dimethylformamide. Temperatures for this reaction can range from 0° C. to the reflux temperature of the solvent. Methods to make related hydrazide ester intermediates of formula $CH_3(CO_2C_2H_5)C=NNCH_3C(=O)Ar$ (where Ar is a substituted phenyl) have been published in the patent literature, see U.S. Pat. Nos. 8,541,414 and 8,470,738, and U.S. Patent Application Publication 2010/0267561. The procedures disclosed in these patent publications are directly applicable to making intermediates useful for preparing the present compounds as depicted in Scheme 3.

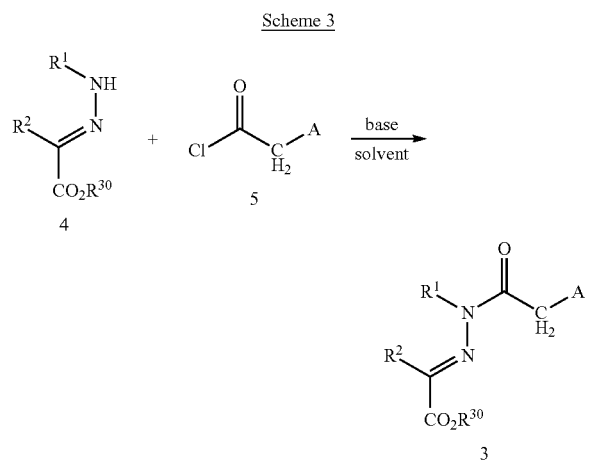

Hydrazone esters of Formula 4 are readily accessible by reaction of an appropriately substituted hydrazine of formula $R^1NHNH_2$ with a ketone or aldehyde ester of formula $R^2(C=O)CO_2R^{30}$ (where $R^{30}$ is typically methyl or ethyl) in a suitable solvent such as ethanol, methanol, acetonitrile or dioxane or dichloromethane at temperatures generally ranging from 0 to 80° C. U.S. Patent Application Publications 2007/0112038 and 2005/0256123 disclose procedures for forming the hydrazone from methylhydrazine and the keto ester $CH_3(C=O)CO_2C_2H_5$.

As shown in Scheme 4, bicyclic acetyl chlorides of Formula 5 can be prepared from the corresponding bicyclic acetic acid esters of Formula 6 wherein $R^{31}$ is typically methyl or ethyl via ester hydrolysis and acid chloride formation. Standard methods for this transformation are known in the literature. For example, ester hydrolysis can be achieved by heating an alcoholic solution of an ester of Formula 6 with an aqueous solution of an alkali metal hydroxide, following by acidification with a mineral acid. The carboxylic acid of Formula 7 formed can then be converted to the corresponding acyl chloride of Formula 5 by treatment with oxalyl chloride and a catalytic amount of N,N-dimethylformamide in an inert solvent such as dichloromethane. *J. Heterocyclic Chem.* 1983, 20(6), 1697-1703; *J. Med. Chem.* 2007, 50(1), 40-64; and PCT Patent Publications WO 2005/012291, WO 98/49141 and WO 98/49158 disclose hydrolysis of benzofuran- and benzothiophene-acetate esters to the corresponding acetic acids. *Monatshefte für Chemie* 1968, 99(2) 715-720 and patent publications WO 2004046122, WO 2009/038974 and JP09077767 disclose conversion of benzofuran- and benzothiophene-acetic acids to the corresponding acid chlorides. The hydrolysis step of Scheme 4 is illustrated by Step D of Synthesis Example 3.

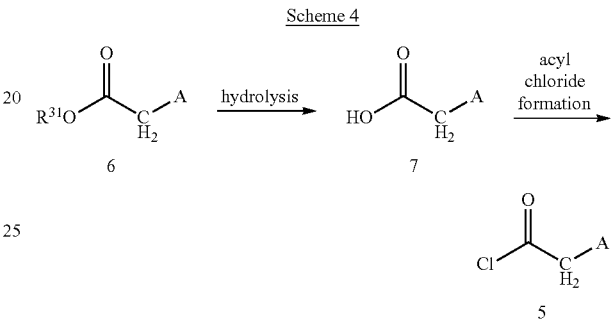

As shown in Scheme 5, bicyclofuran acetates of Formula 6a (i.e. Formula 6 wherein $Y^4$ is O) can be made from bicyclicfuran-3-ones of Formula 8 (wherein A is A-4) via either a Wittig reaction with a (triphenylphosphoranylidine) acetate of Formula 9 wherein $R^{31}$ is typically methyl or ethyl in an inert solvent such as tetrahydrofuran or toluene or by a Wadsworth-Emmons reaction using a phosphonate acetate of Formula 10 wherein $R^{31}$ is typically methyl or ethyl in the presence of a base such as sodium hydride or potassium tert-butoxide in a suitable solvent that is generally anhydrous tetrahydrofuran or dioxane. This reaction involves migration of an initially formed exocyclic double bond (formation of a dihydrobenzofuran substituted unsaturated ester) to inside the bicyclicfuran ring system, thereby giving rise to a bicyclicfuran acetate of Formula 6a. Experimental conditions for a Wittig transformation are provided in PCT Patent Publication WO 2008/074752. Temperatures typically range from 0° C. to the reflux temperature of the solvent. In some cases, longer heating is required to drive migration of the exocyclic double bond in conjugation with the ester to the endocyclic position within the fully bicyclicfuran ring system. The method of Scheme 5 is illustrated by Step B of Synthesis Example 3.

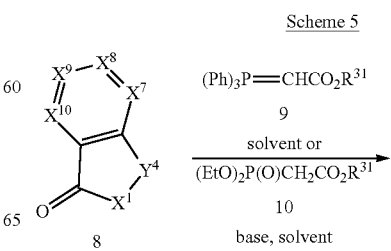

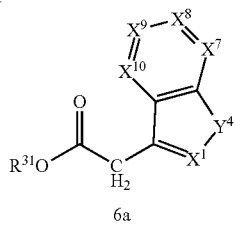

$Y^4$ is O or S

As shown in Scheme 6, substituted bicyclicfuran-3-ones or bicyclicthiophen-3-ones of Formula 8 (wherein A is A-4) where $R^4$ is hydrogen or alkyl can be made by first alkylating a salicylate of Formula 11 with an α-bromo ester of Formula 12 (wherein $R^{32}$ is typically methyl or ethyl) in the presence of a base such as potassium carbonate or sodium hydride in an appropriate solvent, e.g., acetonitrile, methanol, ethanol, tetrahydrofuran, diethyl ether, 1,2-dimethoxyethane, dioxane or N,N-dimethylformamide, at temperatures ranging from 0° C. to the reflux temperature of the solvent. Next, the bis-ester of Formula 13 is treated with a metal halide or alkoxide, e.g., sodium hydride or potassium tert-butoxide, in an inert solvent such as tetrahydrofuran, dioxane, 1,2-dimethoxyethane or N,N-dimethylformamide to form the corresponding bicyclicfuran-3-one of Formula 8. An alternative more stepwise process for converting diesters of Formula 13 to bicyclicfuran-3-ones of Formula 8 has been reported in PCT Patent Publication WO 2008/074752 whereas the method in Scheme 5 allows for cyclization of diesters of Formula 13 followed by ester hydrolysis and decarboxylation to provide bicyclicfuran-3-ones of Formula 8 in one convenient step.

As illustrated in Scheme 7, substituted bicyclicthiophenes of Formula 6b (i.e. Formula 6 wherein X is S) where $R^4$ is hydrogen or alkyl are readily accessible by cyclization of appropriately substituted phenylthio ketoesters of Formula 14, generally under acidic conditions and preferably with polyphosphoric acid (PPA) neat or in an inert generally high boiling solvent, e.g., chlorobenzene, xylene or toluene. Chlorobenzene is the preferred solvent. For a literature example of this cyclization using PPA in chlorobenzene, see *J. Heterocyclic Chem.* 1988, 25, 1271-1272. Also see U.S. Pat. No. 5,376,677 for published experimental detail for making benzothiophene acetates using this PPA-mediated cyclization.

Scheme 7

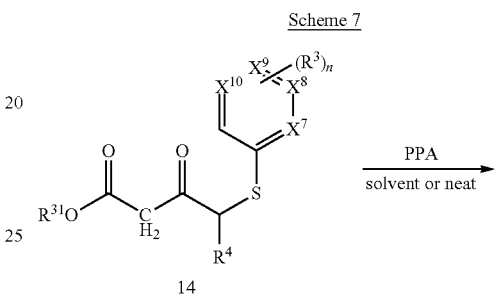

As shown in Scheme 8, by methods also taught in *J. Heterocyclic Chem.* 1988, 25, 1271-1272 and U.S. Pat. No. 5,376,677, substituted 4-phenylthio-1,3-ketoesters of Formula 14, can be readily made by alkylation of thioheterocycles of Formula 15 with 4-bromo-1,3-ketoesters of Formula 16 (i.e. $R^4CHBr(C=O)CH_2CO_2R$ where R is generally methyl or ethyl) in the presence of base in solvent. Alkylation with an alkali or alkaline carbonate such as potassium carbonate in a polar aprotic solvent such as acetonitrile or N,N-dimethylformamide is generally preferred.

Scheme 6

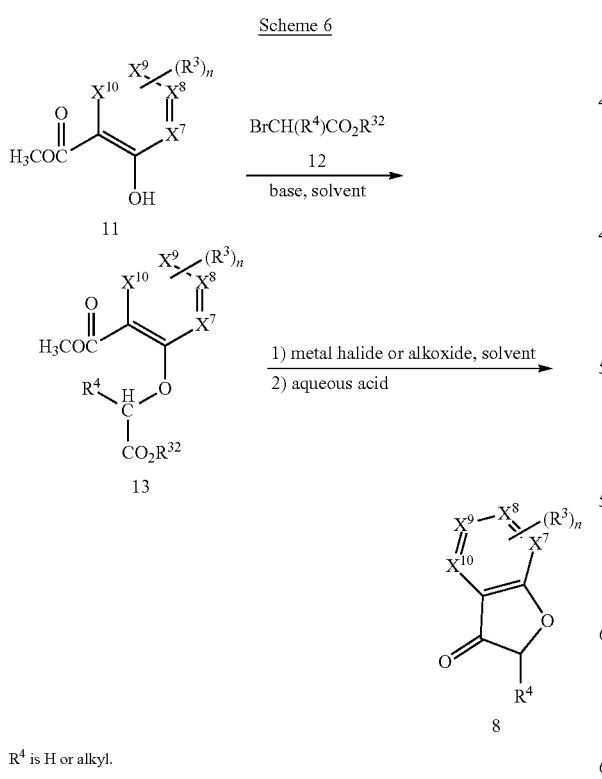

$R^4$ is H or alkyl.

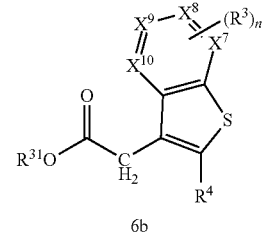

Scheme 8

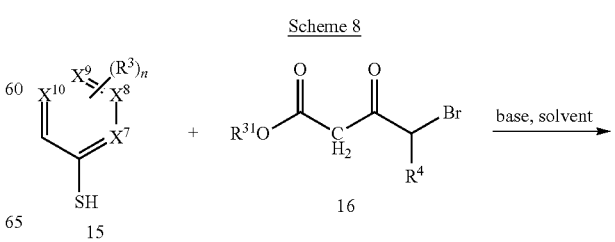

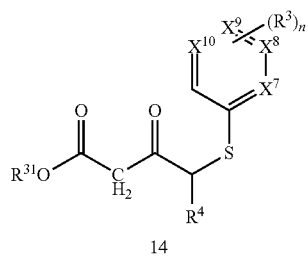

14

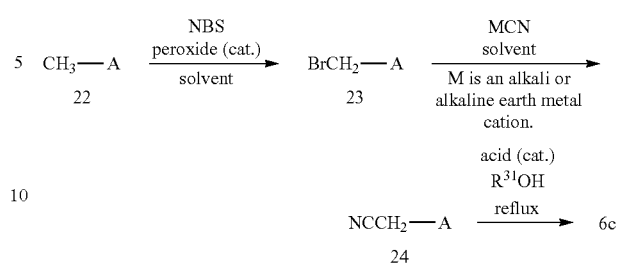

Scheme 10

As shown in Scheme 9, heteroarylacetic acid derivatives of Formula 6c (i.e. Formula 6 wherein X is —C($R^6$)=C ($R^7$)—) can be prepared from appropriately substituted heteroaryl amines of Formula 17. According to this method, amines of Formula 17 are diazotized (preferably with t-butyl nitrite in the presence of cupric chloride in acetonitrile) in the presence of 1,1-dichloroethene (18) to give the corresponding trichloroethylheterocycle of Formula 19. The trichloroethylheterocycle of Formula 19 are then heated with an appropriate alkali or alkaline earth alkoxide such as a sodium alkoxide of Formula 20, in a suitable solvent such as an alcohol of Formula 21, followed by acidification such as with concentrated sulfuric acid to provide the heterocyclic acetic acid esters of Formula 6c. This method is taught in *Pest. Manag. Sci.* 2011, 67, 1499-1521 and U.S. Pat. No. 5,376,677.

Hydrolysis of leaving groups at the 5-position of the pyridazinone ring can be accomplished as shown in Scheme 11. When the LG group is lower alkoxy, lower alkylsulfide (sulfoxide or sulfone), halide or N-linked azole, it can be removed by hydrolysis with basic reagents such as tetrabutylammonium hydroxide in solvents such as tetrahydrofuran, dimethoxyethane or dioxane at temperatures from 0 to 120° C. Other hydroxide reagents useful for this hydrolysis include potassium, lithium and sodium hydroxide (see, for example, WO 2009/086041). When the LG group is lower alkoxy, hydrolysis of the LG group can also be accomplished with dealkylation reagents such as boron tribromide or morpholine (see, for example, WO 2009/086041, WO 2013/160126 and WO 2013/050421).

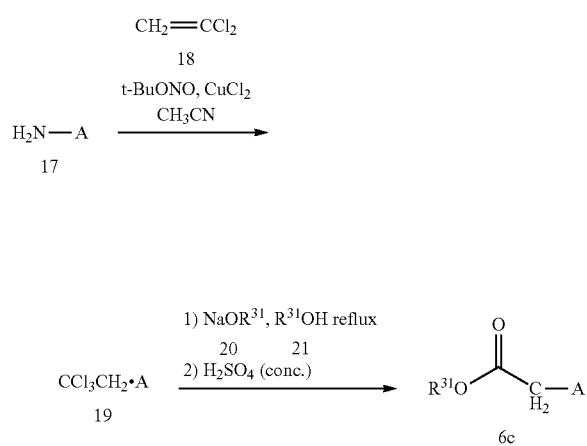

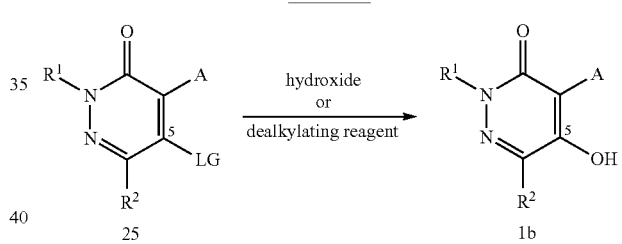

An alternative method for making heteroaryl acetic acid esters of Formula 6c is outlined in Scheme 10. As taught by the method in *Pest. Manag. Sci.* 2011, 67, 1499-1521, methyl heterocycles of Formula 22 can be brominated with N-bromosuccinimide (NBS) under free radical conditions (e.g., benzoyl peroxide as catalyst) in an inert solvent such as dichloromethane, dichloroethane or tetrachloromethane to give heteroaryl methyl bromides of Formula 23. Displacement of the bromine with cyanide by reacting compounds of Formula 23 with an alkali or alkaline cyanide (e.g., potassium cyanide) affords the heteroaryl acetonitriles of Formula 24 that can be hydrolyzed with esterification to the acetates of Formula 6c by heating in acidic alcohol (e.g., HCl in methanol or ethanol), generally at the reflux temperature of the solvent. Alcohol $R^{31}$OH is a lower alkanol.

Introduction of a halogen at the 6-position of the pyridazinone can be accomplished by zincation followed by halogenation. For conditions, reagents and examples of zincation of pyridazinones, see Verhelst, T., Ph.D. thesis, University of Antwerp, 2012. Typically the pyridazinone of Formula 26 is treated in tetrahydrofuran with a solution of Zn(TMP)-LiCl or Zn(TMP)$_2$—MgCl$_2$—LiCl (i.e. 2,2,6,6-Bis(tetramethylpiperidine)zinc, magnesium chloride, lithium chloride complex in toluene/tetrahydrofuran) at −20 to 30° C. to form a zinc reagent. Subsequent addition of bromine, N-bromosuccinimide or iodine provides compounds of Formula 27 (wherein $R^2$ is Br or I, respectively). Reagents such as thichloroisocyanuric acid or 1,3-dichloro-5,5-dimethylhydantoin give a compound of Formula 27 (wherein $R^2$ is Cl). This method is shown in Scheme 12. For preparation of a variety of appropriate zincation reagents, see Wunderlich, S. Ph.D. thesis, University of Munich, 2010 and references cited therein, as well as WO 2008/138946 and WO 2010/092096 Zincation at the 6-position of the pyridazinone ring can be accomplished in the presence of aromatic/heteroaromatic substituents, alkoxy substituents or halogen at the 4-position of the pyridazinone ring, or in the presence of halogen or alkoxy substituents at the 5-position of the pyridazinone ring.

Scheme 12

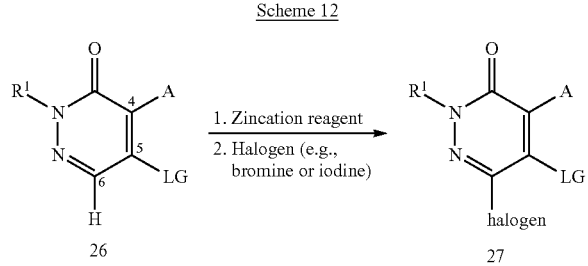

The R² substituent of compounds of Formula 28 (wherein R² is halogen or sulfonate) can be further transformed into other functional groups. Compounds wherein R² is alkyl, cycloalkyl or substituted alkyl can be prepared by transition metal catalyzed reactions of compounds of Formula 28 as shown in Scheme 13. For reviews of these types of reactions, see: E. Negishi, *Handbook of Organopalladium Chemistry for Organic Synthesis*, John Wiley and Sons, Inc., New York, 2002, N. Miyaura, *Cross-Coupling Reactions: A Practical Guide*, Springer, New York, 2002, H. C. Brown et al., *Organic Synthesis via Boranes*, Aldrich Chemical Co., Milwaukee, Vol. 3, 2002, Suzuki et al., *Chemical Reviews* 1995, 95, 2457-2483 and Molander et al., *Accounts of Chemical Research* 2007, 40, 275-286. Also see Tetrahedron Organic Chemistry Series Vol. 26: *Palladium in Heterocyclic Chemistry*, 2nd Ed., Gribble and Li, editors, Elsevier, Amsterdam, 2007. For a review of Buchwald-Hartwig chemistry see Yudin and Hartwig, *Catalyzed Carbon-Heteroatom Bond Formation*, 2010, Wiley, New York.

Scheme 13

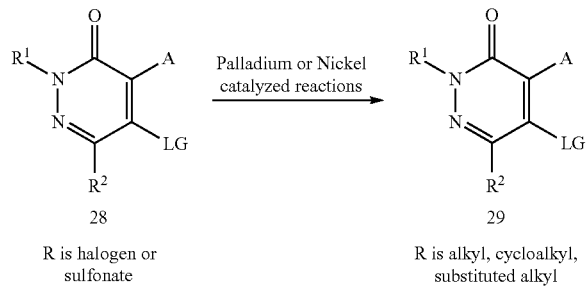

Related synthetic methods for the introduction of other functional groups at the R² position of Formula 30a are known in the art. Copper catalyzed reactions are useful for introducing the CF₃ group. For a comprehensive recent review of reagents for this reaction see Wu, Neumann and Beller in *Chemistry: An Asian Journal*, 2012, ASAP, and references cited therein. For introduction of a sulfur containing substitutent at this position, see methods disclosed in WO 2013/160126. For introduction of a cyano group, see WO 2014/031971. For introduction of a nitro group, see *J. Am. Chem. Soc.*, 2009, 12898. For introduction of a fluoro substituent, see *J. Am. Chem. Soc.*, 2014, 3792.

Compounds of Formula 28 can be prepared by reaction of organometallic reagents of Formula 30 with pyridazinones of Formula 30a with a reactive group at the 4-position, as shown in Scheme 14. Depending upon the leaving group a transition metal catalyst may be desirable. When the leaving group is lower alkoxy, N-linked azole (such as pyrazole or triazole) or sulfonate, no catalyst is required, and reaction directly with a magnesium reagent or lithium reagent can take place at the 4-position. This reaction can be done in a variety of solvents which do not react with organomagnesium reagents. Typical reaction conditions include tetrahydrofuran as the solvent, a reaction temperature of −20 to 65° C., and an excess of the organomagnesium or organolithium reagent. When the reactive group at the 4-position is halogen, a transition metal catalyst and ligand are helpful. A variety of different coupling partners can be used, including boron (Suzuki Reaction), tin (Stille Reaction), and zinc (Negishi reaction); these reactions can be catalyzed by palladium and nickel catalysts with a wide variety of ligands. Conditions for these reactions are known in the art; see, for example, *Palladium-Catalyzed Coupling Reactions: Practical Aspects and Future Development* Edited by Arpad Molnar, Wiley, 2013 and references cited within. The organomagnesium reagents used in the non-catalyzed process can be prepared by direct insertion of magnesium into a carbon-halogen bond (optionally in the presence of a lithium halide), by a Grignard exchange reaction with an i-propylmagnesium halide (optionally in the presence of a lithium halide), or by transformation of an organolithium reagent by reaction with a magnesium salt such as magnesium bromide etherate. A variety of groups which are inert toward the organomagnesium reagents can be present at R² and at the 5-position of the pyridazinone in these reactions. Compounds of Formula 30 can be prepared according to methods found in Knochel et al. *Angew.* 2011, 50, 9794-9824, and *Heterocycles* 2014, 88, 827-844.

Scheme 14

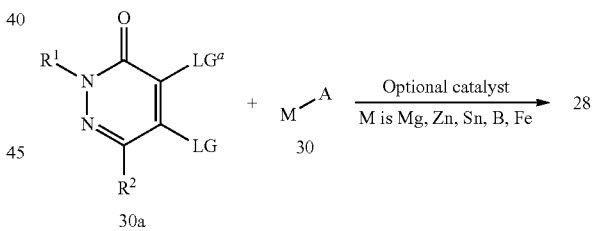

Compounds of Formula 30a are known in the art or can be prepared by methods described by Maes and Lemiere in *Comprehensive Heterocyclic Chemistry III Volume* 8, Katritsky, Ramsden, Scriven and Taylor editors and references cited therein. See also Verhelst, Ph.D. thesis University of Antwerp and references cited therein. Functional group transformations on pyridazinones are also described in Stevenson et. al. *J. Heterocyclic Chem.* 2005, 42, 427; U.S. Pat. No. 6,077,953; WO 2009/086041 and references cited therein; U.S. Pat. No. 2,782,195; WO 2013/160126; and WO 2013/050421.

Compounds of Formula 1b can also be prepared by hydrolysis of sulfones of Formula 31 in aqueous base. Suitable bases include sodium, potassium or tetrabutylammonium hydroxide. Typical reaction temperatures range from 0 to 80° C., and typical reaction times are 1-12 hours. This method is shown in Scheme 15.

Scheme 15

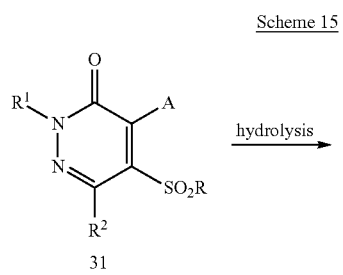

Compounds of Formula 31 can be prepared by the alkylation of compounds of Formula 31a wherein $R^1$ is H with alkyl halides and sulfonates. Typical bases useful in this method include potassium, sodium or cesium carbonate. Typical solvents include acetonitrile, tetrahydrofuran or N,N-dimethylformamide as shown in Scheme 16.

Scheme 16

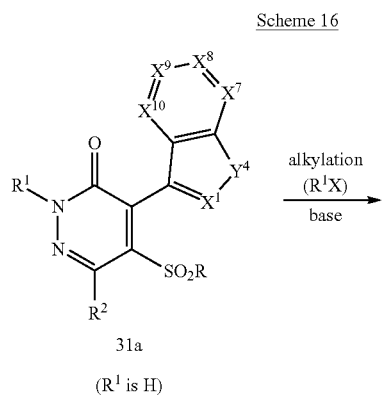

Compounds of Formula 31a can be prepared by the cyclization of compounds of Formula 32 by treatment with base. Typical bases useful in this method include potassium, sodium or cesium carbonate. Typical solvents include acetonitrile, tetrahydrofuran or N,N-dimethylformamide as shown in Scheme 17.

Scheme 17

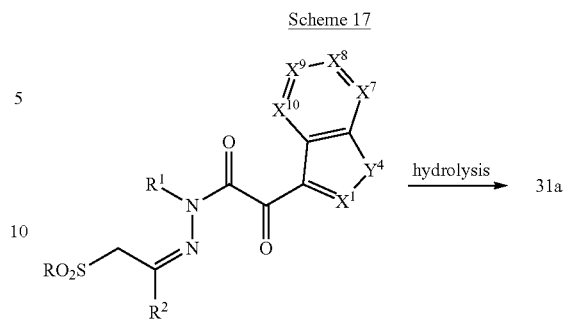

Compounds of Formula 32 can be prepared by the method shown in Scheme 18. In this method, compounds of Formula 33 are coupled with compounds of Formula 34 in the presence of a base. Bases useful in this method include triethylamine, sodium or potassium carbonate, pyridine or diisopropylethylamine

Scheme 18

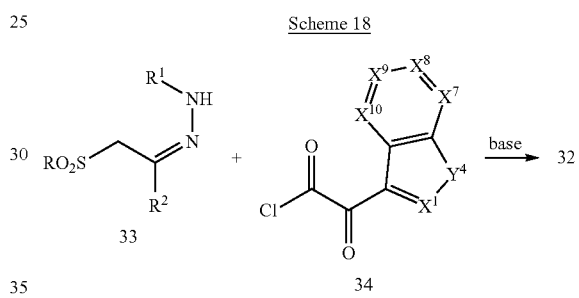

Compounds of Formula 33 can be prepared by methods known in the art.

Compounds of Formula 34 can be prepared by several methods. In one method shown in Scheme 19, compounds of Formula 35 are first treated with $ClC(O)CO_2Me$ in the presence of aluminum trichloride. Subsequent hydrolysis to the carboxylic acid, followed by treatment with oxalyl chloride, provides the acyl chlorides of Formula 34.

Scheme 19

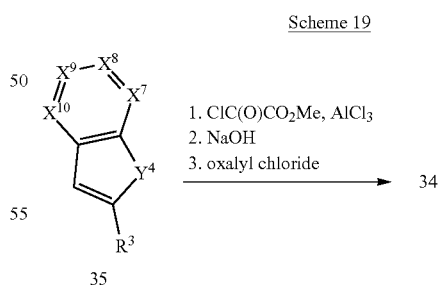

Compounds of Formula 35 are commercially available or can be prepared by methods known in the art.

Compound of Formula 34 can also be made by the reaction of heteroaromatic organometallic reagents with activated oxalate esters of Formula 36. The activating group can be an alkyl ester, a halogen or an imidazole. The metal can be lithium or magnesium. Other metal groups such as zinc and tin may be used if a palladium catalyst is utilized.

Scheme 20

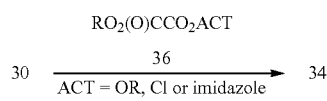

As shown in Scheme 21 compounds of Formula 1c can be made by rearrangement of compounds of Formula 37. This rearrangement may be carried out at temperatures between 110 and 300° C. Suitable solvents include, but are not limited to, aromatic hydrocarbons such as xylenes, diethylbenzene, and mesitylene as well as halogenated aromatics such as dichlorobenzene. Other high boiling solvents such as Dowtherm A and diglyme may be successfully employed. Many other solvents with lower boiling points can be used in conjunction with microwave heating especially when ionic liquids are added to the medium.

Scheme 21

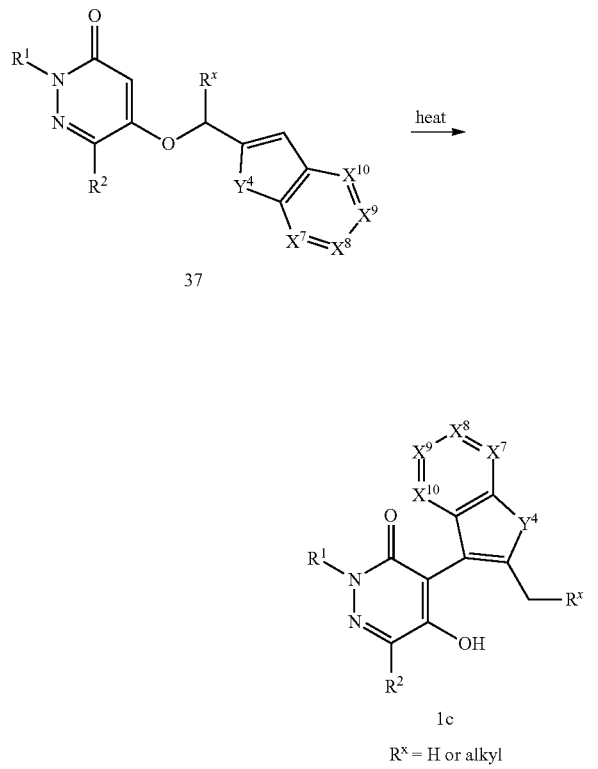

$R^x$ = H or alkyl

Compounds of Formula 37 can be prepared as shown in Scheme 22 by alkylation of pyridazinones of Formula 38 with alkyl halides of Formula 39. The reaction can be carried out in a variety of solvents such as acetone, 2-butanone, acetonitrile, dimethylacetamide, N-methylpyrrolidinone, dimethylsulfoxide and dimethylformamide. The presence of an acid acceptor such as, but not limited to, cesium carbonate, potassium carbonate, sodium carbonate, potassium hydroxide or sodium hydroxide is preferred. The leaving group Y can be halogen or sulfonate.

Scheme 22

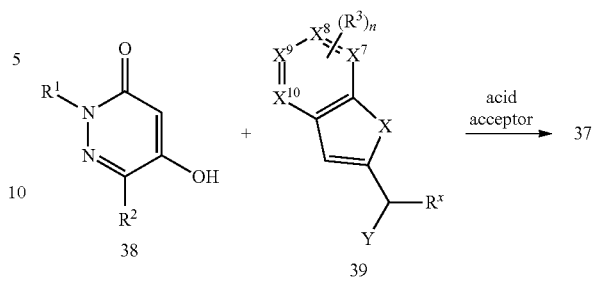

Compounds of Formula 37 may also be prepared as shown in Scheme 23 by the nucleophilic displacement reaction of pyridazinones of Formula 40 with alcohols of Formula 41. Suitable solvents include dioxanes, dimethoxyethane, tetrahydrofuran, dimethylacetamide, N-methylpyrrolidinone, dimethylsulfoxide and dimethylformamide. Suitable acid acceptors include, but are not limited to, sodium hydride, potassium hydride, potassium t-butoxide, sodium hexamethyldisilazide, potassium hexamethyldisilazide, and lithium hexamethyldisilazide.

Scheme 23

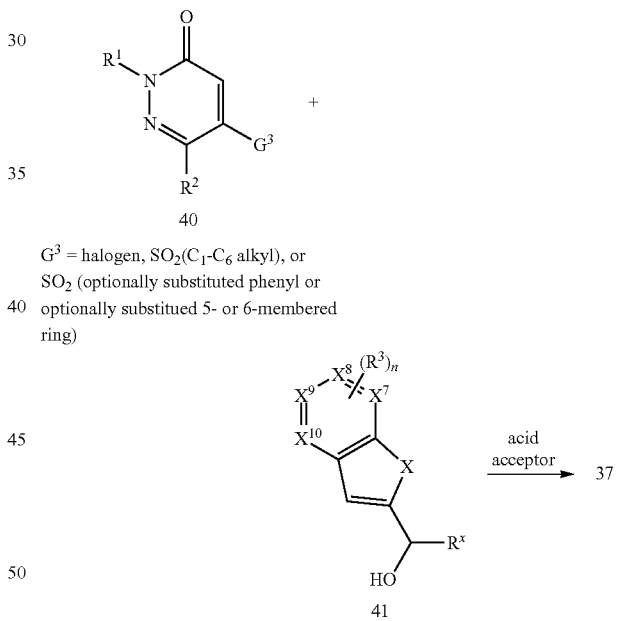

$G^3$ = halogen, $SO_2(C_1$-$C_6$ alkyl), or $SO_2$ (optionally substituted phenyl or optionally substitued 5- or 6-membered ring)

Compounds of Formula 25 can be prepared by coupling reactions of organometallic pyridazinone coupling partners of Formula 42 with heteroaryl halides and sulfonates of Formula 43. The organometallic coupling partner can be, for example, an organozinc, organomagnesium, organotin, or organoboron reagent. Palladium catalysts such as palladium tetrakis (triphenylphosphine) and those generated from other palladium sources, such as $Pd_2dba_3$ and $Pd(OAc)_2$, and a phosphine or N-heterocyclic carbene ligand can be used in the coupling procedures (Maes et al. *J. Org. Chem.*, 2011, 76, 9648-9659). Palladium precatalysts based on dialkyl biarylphosphine ligands, such as X-Phos, S-Phos and Ru-Phos (Buchwald et al. *Angew. Chem. Int. Ed.*, 2013, 52(2), 615-619.), or precatalysts derived from N-heterocyclic carbene ligands such as PEPPSI-i-Pr and PEPPSI-i-Pent (Organ et al. *Eur. J. Org. Chem.* 2010, 4343-4354) can effect this coupling as well. The reaction can be carried out in solvents such as tetrahydrofuran, dimethoxyethane, N-Methyl-2-pyrrolidone and dioxane. Coupling partners may be either heterocyclic halides or sulfonates. A particularly useful class of coupling partners for the reaction are those based on nonaflates ($OSO_2C_4F_9$) of heteroaromatic compounds. Halogenated heterocyclic coupling partners are commercially available or known in the literature. Especially useful halogenated benzofurans can be made from halogenated phenols by methods detailed in WO 2003/043624. Especially useful methods for making halogenated benzothiophenes from halogenated thiophenols are given in WO 2001/002411. Other useful classes of heterocyclic halides and synthetic routes are given in Tetrahedron Organic Chemistry Series Vol. 26: *Palladium in Heterocyclic Chemistry*, 2nd Ed., Gribble and Li, editors, Elsevier, Amsterdam, 2007.

Scheme 24

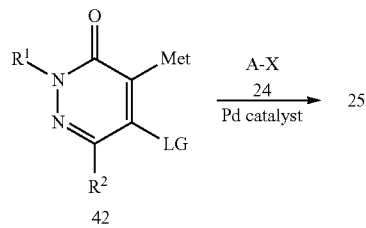

Zincation of the 4-position of a pyridazinone can be accomplished with zincation reagents such as 2,2,6,6-Bis(tetramethylpiperidine)zinc, magnesium chloride, lithium chloride complex in toluene/tetrahydrofuran (i.e. Zn(TMP)-LiCl or Zn(TMP)$_2$—MgCl$_2$—LiCl).

Magnesiation of this position can also be accomplished by treatment with Mg(TMP)-LiCl. See Verhelst, T., Ph.D. thesis, University of Antwerp, 2012 for conditions for pyridazinone metallation and for palladium catalyzed cross-coupling of 4-zincated and 4-magnesiated pyridazinones. The synthesis and cross-coupling conditions for 4-stannylpyridazinones are known from Stevenson et. al. *J. Heterocyclic Chem.* 2005, 42, 427.

As shown in Scheme 25, pyridazinones of Formula 1a (a subset of compounds of Formula 1 where W is O) can be thionated to give the corresponding thiones of Formula 1c (i.e. Formula 1 wherein W is S) with a thionation reagent that is generally phosphorus pentasulfide in pyridine or Lawesson's reagent (2,4-bis-(4-methoxyphenyl)-1,3-dithia-2,4-diphosphetane 2,4-disulfide) in an appropriate solvent (e.g., toluene, tetrahydrofuran or dioxane) at temperatures generally ranging 0° C. to room temperature.

Scheme 25

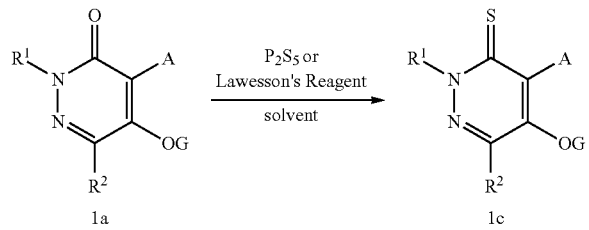

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. Mass spectra (MS) are reported as the molecular weight of the highest isotopic abundance parent ion (M+1) formed by addition of H+(molecular weight of 1) to the molecule, or (M−1) formed by the loss of H+(molecular weight of 1) from the molecule, observed by using liquid chromatography coupled to a mass spectrometer (LCMS) using either atmospheric pressure chemical ionization (AP+) where "amu" stands for unified atomic mass units. All NMR spectra are reported in CDCl$_3$ downfield from tetramethylsilane at 400 MHz unless otherwise indicated where s means singlet, brs meand broad singlet, d means doublet, t means triplet, m means multiplet, and ddd means doublet of double doublets.

Synthesis Example 1

Preparation of 5-hydroxy-2,6-dimethyl-4-(2-methyl-7-benzofuranyl)-3(2H)-pyridazinone (Compound 12)

Step A: Preparation of 1-bromo-2-(2-propyn-1-yloxy)-benzene

To a solution of 2-bromophenol (15 g, 86.7 mmol) in N,N-dimethylformamide (225 mL) was added propargyl bromide (80% in toluene, 19.18 g, 130.05 mmol) and potassium carbonate (24 g, 173.4 mmol) was stirred for 16 h at room temperature. The reaction mixture was quenched with $H_2O$, extracted with ethyl acetate (3×150 mL) followed by brine solution, dried over $Na_2SO_4$ filtered and concentrated. The resulting crude material was purified by silica gel column chromatography eluting with 3% ethyl acetate in petroleum ether to isolate the title compound as a pale yellow liquid (12 g).

$^1$H-NMR δ 2.43 (s, 1H), 4.78 (s, 2H), 6.91 (t, 1H), 7.08 (d, 1H), 7.28 (m, 1H), 7.56 (d, 1H).

Step B: Preparation of 7-bromo-2-methyl-benzofuran

To a solution of 1-bromo-2-(2-propyn-1-yloxy)-benzene (i.e. the product obtained in Example 1, Step A) (12 g, 56.87 mmol) in N,N-diethylaniline (960 mL) was added cesium fluoride (12.9 g, 85.30 mmol). The reaction mixture was stirred for 5 h at 230° C. The reaction mixture was cooled to ambient temperature and filtered through celite bed and washed with ethyl acetate. The mother liquor washed with 2 N aqueous hydrochloric acid solution (2×50 mL) followed by brine solution and dried over $Na_2SO_4$ filtered and concentrated. The crude residue was purified by silica gel column chromatography eluting with 3% ethyl acetate in petroleum ether to yield a pale yellow liquid (9 g). M.S.=210 (M+1).

Step C: Preparation of 4,5-dichloro-6-iodo-2-methyl-3(2H)-pyridazinone

To 4,5-dichloro-2-methyl-3(2H)-pyridazinone (5.0 g, 27.9 mmol) dissolved in 80 mL tetrahydrofuran was added 2,2,6,6-bis(tetramethylpiperidine)zinc, magnesium chloride, lithium chloride complex 0.35M in toluene/tetrahydrofuran (i.e. $Zn(TMP)_2$—LiCl—$MgCl_2$ 54 mL, 0.35 M in tetrahydrofuran/toluene) 18.75 mmol) over 3 to 5 min. The cloudy reaction mixture was stirred for 15 min and then iodine (8.5 g, 33.51 mmol) was added. The resulting mixture was stirred at ambient temperature for 15 min. The reaction mixture was quenched with aqueous sodium bisulfite solution (to remove excess iodine color), then water (200 mL) followed by 1 N aqueous hydrochloric acid (100 mL). The mixture was extracted with ethyl acetate (300 mL, then 200 mL). The resulting crude product which was purified by silica gel column chromatography eluting with 10% ethyl acetate in petroleum ether. A solid was triturated with diethyl ether and pentane, and the resulting pale yellow solid was dried (3 g).

$^1$H NMR δ 3.83 (s, 3H).

Step D: Preparation of 5-chloro-6-iodo-4-methoxy-2-methyl-3(2H)-pyridazinone To 4,5-dichloro-6-iodo-2-methyl-3(2H)-pyridazinone (i.e. the product obtained in Step C) (3 g, 9.86 mmol) in 1,4-dioxane (30 mL) was added sodium methoxide (25% w/w solution in methanol, 2.72 mL, 12.63 mmol) and the resulting mixture was stirred at ambient temperature for 1 h. The reaction mixture was quenched with saturated aqueous $NH_4Cl$ and extracted with ethyl acetate (100 mL, then 50 mL) two times. The resulting crude product was purified by silica gel column chromatography eluting with 5% ethyl acetate in petroleum ether. A solid was triturated with diethyl ether and pentane, and the resulting off-white solid was dried (2 g).

$^1$H NMR δ 3.75 (s, 3H), 4.28 (s, 3H).

Step E: Preparation of 5-chloro-4-methoxy-2,6-dimethyl-3(2H)-pyridazinone

A mixture of 5-chloro-6-iodo-4-methoxy-2-methyl-3(2H)-pyridazinone (i.e. the product obtained in Step D) (2 g, 6.66 mmol), trimethylboroxine (1.21 mL, 8.66 mmol), cesium carbonate (6.50 g, 19.9 mmol), [1,1'-bis(diphenylphosphino)ferrocene]dichloropalladium(II), (0.27 g, 0.33 mmol) in 1,4-dioxane (20 mL) was heated at the reflux temperature of the solvent for 5 h. The reaction mixture was cooled and quenched with a mixture of brine and ethyl acetate. The aqueous layer was extracted with ethyl acetate (40 mL, then 20 mL) two times. The resulting residue was was purified by silica gel column chromatography with 5% ethyl acetate in petroleum ether, and a solid was triturated with diethyl ether and pentane. The off-white solid was collected and dried (1 g).

$^1$H NMR δ 2.37 (s, 3H), 3.72 (s, 3H), 4.26 (s, 3H).

Step F: Preparation of 5-chloro-2,6-dimethyl-4-(2-methyl-7-benzofuranyl)-3 (2H)-pyridazinone To a solution of 7-bromo-2-methyl-benzofuran (i.e. the product obtained in Example 1, Step B) (1.0 g, 4.73 mmol) in dry tetrahydrofuran was added n-butyllithium (2.5 M in hexanes, 3.34 g, 5.68 mmol) drop wise for 5 min at −78° C. and stirred for 1.5 h, followed by addition of 5-chloro-4-methoxy-2,6-dimethyl-3(2H)-pyridazinone (i.e. the product obtained in Example 1, Step E) at −78° C. and stirred for 2.5 h. The reaction mixture was quenched with saturated $NH_4Cl$ solution followed by extraction with ethyl acetate (3×10 mL) followed by brine solution, dried over $Na_2SO_4$ filtered and concentrated. The obtained crude material was purified by silica gel column chromatography eluting with 25% ethyl acetate in petroleum ether. The residue was triturated with diethyl ether and pentane, and the resulting solid dried to provide 250 mg of the title compound as a white solid. M.P. 153-156° C.

Step G Preparation of 5-hydroxy-2,6-dimethyl-4-(2-methyl-7-benzofuranyl)-3(2H)-pyridazinone (Compound 12)

To a solution of 5-chloro-2,6-dimethyl-4-(2-methyl-7-benzofuranyl)-3(2H)-pyridazinone (i.e. the compound obtained in Example 1, Step F) (200 mg, 0.69 mmol) in 1,4-dioxane (2 mL) was added tetrabutylammonium hydroxide (1 mL) and the resulting mixture was stirred for 5 h at 100° C. The reaction mixture was diluted with water (3 mL) and acidified to pH=3 with 1 N hydrochloric acid solution. The aqueous layer was extracted with dichloromethane (3×5 mL), washed with brine solution, then dried over $Na_2SO_4$, filtered and concentrated. The obtained crude material was purified by silica column gel column chromatography, eluting with 60% ethyl acetate in petroleum ether. The Synthesis Example 2

Preparation of 5-(acetyloxy)-2,6-dimethyl-4-(2-methyl-7-benzofuranyl)-3 (2H)-pyridazinone (Compound 13)

Step A: Preparation of 5-(acetyloxy)-2,6-dimethyl-4-(2-methyl-7-benzofuranyl)-3(2H)-pyridazinone (Compound 13)

To a solution of 5-hydroxy-2,6-dimethyl-4-(2-methyl-7-benzofuranyl)-3(2H)-pyridazinone (i.e. the compound obtained in Example 1, Step G) (150 mg, 0.55 mmol) in dichloromethane was added triethylamine (0.2 mL, 1.38 mmol) and acetyl chloride (0.04 mL, 0.61 mmol) at 0° C. The resulting mixture was stirred at 0° C. for 4 h. After warming to ambient temperature, water (5 mL) was added and the resulting mixture was extracted with dichloromethane (2×5 mL), washed with water followed by saturated aqueous $NaHCO_3$, brine solution then dried over $Na_2SO_4$, filtered and concentrated. The obtained crude material was purified by silica gel column chromatography eluting with 20% ethyl acetate in petroleum ether, triturated with diethyl ether and pentane and dried to yield a pale brown solid (100 mg). M.P.=144-147° C.

resulting residue was triturated with diethyl ether and the resulting solid was washed with pentane and dried to yield an off-white solid (90 mg). M.P.=272-275° C.

Synthesis Example 3

Preparation of 5-hydroxy-2,6-dimethyl-4-(5-methyl-benzo[b]thien-4-yl)-3(2H)-pyridazinone (Compound 29)

Step A: Preparation of 6,7-dihydro-5-methyl-benzo[b]thiophen-4(5H)-one

To a solution of 6,7-dihydro-benzo[b]thiophen-4(5H)-one (10 g, 65.8 mmol) in tetrahydrofuran (100 mL) was added lithium diisopropylamide (7.74 g, 72.6 mmol) dropwise at −78° C. for 10 min. The resulting mixture was stirred for 1 h at −78° C., then iodomethane (11.13 g, 78.9 mmol) was added, and the mixture was stirred at −78° C. and allowed to warm to ambient temperature over 5 h. The reaction mixture was quenched with saturated aqueous ammonium chloride solution, and was extracted with ethyl acetate (3×10 mL) followed by brine solution, dried over $Na_2SO_4$ filtered and concentrated. The major component was isolated by silica gel column chromatography eluting with 5% ethyl acetate in petroleum ether to isolate the title compound as a pale yellow liquid (3 g).

Step B: Preparation of ethyl dihydro-5-methylbenzo[b]thien-4(5H-ylidene)acetate, and ethyl 6,7-dihydro-methylbenzo[b]thiophene-4-acetate To 50 mL dry ethanol was added sodium metal (5.3 g, 240.9 mmol) portion wise at ambient temperature and stirred for 2 h. Triethylphosphonoacetate was added at ambient temperature and stirred for 10 min followed by addition of 6,7-dihydro-5-methyl-benzo[b]thiophen-4(5H)-one (i.e. the compound obtained in Example 3, Step A) at ambient temperature and stirred for 16 h at 80° C. The reaction mixture was cooled to ambient temperature then poured over ice-water. The mixture was extracted with ethyl acetate (3×50 mL) and the combined organic layers were washed with brine solution, dried over $Na_2SO_4$ filtered and concentrated. The resulting residue was purified by silica gel column chromatography eluting with 4% ethyl acetate in petroleum ether to isolate a mixture of the title compounds as a mixture of the title components and concentrated to give a pale yellow liquid (2 g). A mixture of the title compounds were carried forward to the next step without further purification. M.S.=237 (M+H).

Step C: Preparation of ethyl 5-methylbenzo[b]thiophene-4-acetate

To a solution of a mixture of ethyl 2-(6,7-dihydro-5-methylbenzo[b]thien-4(5H-ylidene)acetate, and ethyl 6,7-dihydro-methylbenzo[b]thiophene-4-acetate (7 g, 29.66 mmol) (i.e. the compounds obtained in Example 3, Step B) in toluene (150 mL) was added 2,3-dichloro-5,6-dicyano-1,4-bezoquinone (DDQ, 16.8 g, 74.15 mmol) at ambient temperature and the resulting mixture was stirred at 100° C. for 24 h. The reaction mixture was then filtered through Celite® diatomaceous earth filter aid and washed with toluene and the filtrate concentrated. The resulting material was purified by silica gel column chromatography eluting with 8% ethyl acetate in petroleum ether to isolate a pale yellow liquid (2.5 g). M.S.=235 (M+H).

Step D: Preparation of 5-methylbenzo[b]thiophene-4-acetic acid

To a solution of ethyl 5-methylbenzo[b]thiophene-4-acetate (i.e. the compound obtained in Example 3, Step C) in a mixture of tetrahydrofuran and $H_2O$ (8:2, 25 mL) was added lithium hydroxide (1 g, 42.7 mmol) and the resulting mixture was stirred for 5 h at ambient temperature. Water (20 mL) was added and the resulting mixture was extracted with ethyl acetate (2×10 mL). The aqueous layer was acidified with 1 N aqueous hydrochloric acid to adjust the pH=3. The aqueous layer was then extracted with dichloromethane (3×10 mL) and the combined organic layers were washed with brine, dried over $Na_2SO_4$ filtered and concentrated. The resulting residue was triturated with diethyl ether and pentane to give an off-white solid (2.1 g). M.P.=152-155° C.

Step E: Preparation of 5-methylbenzo[b]thiophene-4-acetic acid 1-methylhydrazide To a solution of 5-methylbenzo[b]thiophene-4-acetic acid in dichloromethane (i.e. the compound obtained in Example 3, Step D) (5 mL) was added N-(3-dimethylaminopropyl)-N'-ethylcabodiimide hydrochloride (EDC, 0.58 g, 1.1 mmol) and pentafluoro phenol (0.49 g, 1.1 mmol) at ambient temperature and stirred the resulting mixture for 3 h. In a separate round-bottom flask, methyl hydrazine sulfate (1.0 g, 3 mmol) was dissolved in dichloromethane (5 mL) and di-isopropylethylamine (0.93 g, 3 mmol) was added and the resulting mixture stirred for 15 min at ambient temperature. The previously prepared mixture of 5-methylbenzo[b]thiophene-4-acetic acid and EDC was then added to this solution and the resulting mixture was stirred at ambient temperature for 30 min Water (5 mL) was added to the reaction mixture, which was then extracted with dichloromethane (3×5 mL). The combined organic layers were washed with water followed by brine solution, dried over $Na_2SO_4$ filtered and concentrated. The resulting crude compound was triturated with diethyl ether to obtain the title compound which was used in the subsequent step (0.55 g, crude).

Step F: Preparation of 5-methylbenzo[b]thiophene-4-acetic acid 2-(2-ethoxy-1-methyl-2-oxoethylidine)-1-methylhydrazide To the crude mixture of 5-methylbenzo[b]thiophene-4-acetic acid 1-methylhydrazide isolated in Example 3, Step E above in ethanol (5 mL) was added ethyl pyruvate (0.41 g, 1.5 mmol) at ambient temperature and stirred the resulting mixture for 16 h. The reaction mixture was concentrated under reduced pressure and water (5 mL) was added. The mixture was extracted with dichloromethane (3×5 mL) and the combined organic layers were washed with brine solution, dried over $Na_2SO_4$ filtered and concentrated. The resulting crude mixture was purified by silica gel column chromatography eluting with 15% ethyl acetate in petroleum ether, and a pale-brown solid was triturated with diethyl ether and pentane (0.2 g). M.S.=333 (M+H).

Step H: Preparation of 5-hydroxy-2,6-dimethyl-4-(5-methylbenzo[b]thien-4-yl)-3(2H)-pyridazinone (Compound 29)

To a solution of 5-methylbenzo[b]thiophene-4-acetic acid 2-(2-ethoxy-1-methyl-2-oxoethylidine)-1-methylhydrazide in acetonitrile (2 mL) was added 1,8-diazabicyclo[5.4.0]undec-7-ene (0.45 g, 5.0 mmol) at 0° C. The resulting mixture was stirred at ambient temperature for 2 d. The reaction mixture was concentrated under reduced pressure and water was added, followed by 2 N aqueous hydrochloric acid to adjust to the pH=3. The aqueous layer was extracted with dichloromethane (3×5 mL) and the combined organic layers were washed with brine solution, dried over $Na_2SO_4$ filtered and concentrated. The resulting crude reaction mixture was purified by silica gel chromatography eluting with 50% ethyl acetate in petroleum ether. A solid was triturated with diethyl ether and pentane to provide an off-white solid, a compound of the invention, which was dried (0.1 g). M.P.=204-207° C.

Synthesis Example 4

Preparation of 6-chloro-5-hydroxy-4-(1-isoquinolinyl)-2-methyl-3(2H)-pyridazinone (Compound 67)

Step A: Preparation of 6-chloro-5-methoxy-2-methyl-4-(trimethylstannyl)-3(2H)-pyridazinone To a suspension of 6-chloro-5-methoxy-2-methyl-3(2H)-pyridazinone (prepared as described in U.S. 2013/0331382) (550 mg, 3.15 mmol) in tetrahydrofuran (6 mL) was added a precooled (−20° C.) solution of 2,2,6,6-Bis(tetramethylpiperidine)zinc, magnesium chloride, lithium chloride complex (7.0 mL, 7.0 mmol, 1.0 M in tetrahydrofuran/toluene) at −20° C. within 30 s. The resulting reaction mixture was stirred at −20° C. for 40 s, then a solution of trimethyltin chloride (1.0 M in tetrahydrofuran, 8.0 mL, 8.0 mmol) was added to the reaction mixture in one portion at −20° C. After stirring for 0.5 h at −20° C., the reaction mixture was quenched with saturated aqueous $NH_4Cl$ solution, then extracted with ethyl acetate. The organic layer was washed with brine, dried with anhydrous $NaSO_4$, concentrated and the residue was purified by column chromatography to provide 600 mg of the title compound as colorless oil.

$^1$H NMR δ 3.84 (s, 3H), 3.70 (s, 3H), 0.41 (s, 9H).

Step B: Preparation of 6-chloro-4-(1-isoquinolinyl)-5-methoxy-2-methyl-3(2H)-pyridazinone A mixture of 1-iodoisoquinoline (310 mg, 1.22 mmol), tetrakis(triphenylphospine)palladium(0) (69 mg, 0.06 mmol) and copper(I) iodide (116 mg, 0.61 mmol) in a reaction vial was evacuated under vacuum, then refiled with nitrogen gas. After this procedure was repeated three times, the mixture was added a solution of 6-chloro-5-methoxy-2-methyl-4-(trimethylstannyl)-3(2H)-pyridazinone (i.e. the product from Example 4, Step A) (485 mg, 1.44 mmol) in 1,4-dioxane (3 mL) under nitrogen. The resulting reaction mixture was stirred at 90° C. for 4 h, then cooled to room temperature, filtered through a short pad of Celite® diatomaceous earth filter aid, rinsed with dichloromethane. The filtrate was concentrated and the residue was purified by column chromatography to provide the title compound (200 mg) as a yellow semi-solid.

$^1$H NMR δ 8.61 (d, 1H), 7.88 (d, 1H), 7.76 (d, 1H), 7.73 (d, 1H), 7.70 (ddd, 1H), 7.60 (ddd, 1H), 3.76 (s, 3H), 3.33 (s, 3H).

Step C: Preparation of 6-chloro-5-hydroxy-4-(1-isoquinolinyl)-2-methyl-3 (2H)-pyridazinone A mixture of 6-chloro-4-(1-isoquinolinyl)-5-methoxy-2-methyl-3(2H)-pyridazinone (i.e. the product of Example 4, Step B) (200 mg, 0.66 mmol) in morpholine (1 mL) was stirred at 100° C. for 1 h. The reaction mixture was then concentrated under reduced pressure to remove the excess morpholine. To the residue was added 2.0 N aqueous hydrochloric acid and the pH was carefully adjusted from 2 to 3. The resulting yellow precipitate was collected by filtration, rinsed with water and dried to provide the title compound (130 mg).

$^1$H NMR (dmso $d_6$) δ 9.00 (brs, 1H), 8.51 (d, 1H), 8.29 (d, 1H), 8.25 (d, 1H), 8.17 (d, 1H), 8.10 (ddd, 1H), 7.84 (ddd, 1H), 3.09 (s, 3H).

Synthesis Example 5

Preparation of 4-(4-fluoro-7-benzofuranyl)-5-methoxy-2,6-dimethyl-3(2H)-pyridazinone (Compound 69)

Step A: Preparation of 5-methoxy-2,6-dimethyl-3(2H)-pyridazinone

6-Chloro-5-methoxy-2-methyl-3(2H)-pyridazinone (prepared as described in U.S. 2013/0331382) (3.18 g, 18.21 mmol), chloro(2-dicyclohexylphosphino-2',6'-dimethoxy-1,1'-biphenyl)[2-(2'-amino-1,1'-biphenyl)]palladium(II) (SPhos-Pd-G2) (1.3 g, 1.82 mmol), trimethylboroxine (1.9 mL, 13.6 mmol) and cesium carbonate (8.9 g, 27.3 mmol) were combined in 1,4-dioxane (50 mL) and stirred at 80° C. under an atmosphere of nitrogen overnight. Upon cooling to ambient temperature, the reaction mixture was diluted with dichloromethane (100 mL). The resulting slurry was filtered through a pad of Celite® diatomaceous earth filter aid. The filtrate was transferred to a separatory funnel and washed with saturated aqueous ammonium chloride solution. The organic layer was separated, dried over $MgSO_4$ and absorbed onto silica gel. Purification was performed by silica gel (40 g) liquid chromatography using a gradient 20 to 100% ethyl acetate in hexanes. The isolated fractions were combined and concentrated to provide the title compound (2.52 g) as a white solid.

$^1$H NMR δ 6.11 (s, 1H), 3.80 (s, 3H), 3.68 (s, 3H), 2.22 (s, 3H).

Step B: Preparation of 4-(4-fluoro-7-benzofuranyl)-5-methoxy-2,6-dimethyl-3(2H)-pyridazinone A dry 2-neck round bottom flask was fitted with a rubber septum and 2-way valve adapter, with one valve leading to a high-vaccuum line and one leading to a balloon of nitrogen. The 2-neck round-bottom flask was charged with 5-methoxy-2,6-dimethyl-3(2H)-pyridazinone (0.70 g, 4.5 mmol), 7-bromo-4-fluoro-2,3-dihydrobenzofuran (1.07 g, 5.0 mmol), chloro(2-dicyclohexylphosphino-2',6'-dimethoxy-1,1'-biphenyl) [2-(2'-amino-1,1'-biphenyl)]palladium (II) (SPhos-Pd-G2) (0.162 g, 0.225 mmol) and 2-dicyclohexylphosphino-2',6'-dimethoxybiphenyl (SPhos) (0.092 g, 0.225 mmol,). The flask was sealed under nitrogen, evacuated and back filled with nitrogen. This was repeated 3 times. Anhydrous tetrahydrofuran (20 mL) was then taken up via syringe and added through the rubber septum to the reaction vessel under an atmosphere of nitrogen. 2,2,6,6-Bis(tetramethylpiperidine)zinc, lithium chloride complex (17% in tetrahydrofuran, 7.8 mL, 5.4 mmol) was then added via syringe through the rubber septa to the reaction mixture. The resulting brown solution was stirred under an atmosphere of nitrogen at 47° C. overnight.

Upon cooling to room temperature, the reaction mixture was poured into aqueous hydrochloric acid (1 N, 50 mL) and extracted into ethyl acetate (4×30 mL). The organic extracts were combined, dried over MgSO$_4$ and absorbed onto silica gel. Purification was performed by silica gel (40 g) liquid chromatography using a gradient of 0 to 100% of ethyl acetate in hexanes. The resulting isolated fractions were combined and the solvent was removed under reduced pressure to provide the title compound (1.15 g) as a yellow solid. M.S.=289 (AP$^+$).

Synthesis Example 6

Preparation of 4-(4-fluoro-7-benzofuranyl)-5-hydroxy-2,6-dimethyl-3(2H)-pyridazinone (Compound 68)

Step A: Preparation of 4-(4-fluoro-7-benzofuranyl)-5-hydroxy-2,6-dimethyl-3(2H)-pyridazinone Morpholine (3 mL) was added to 4-(4-fluoro-7-benzofuranyl)-5-methoxy-2,6-dimethyl-3(2H)-pyridazinone (i.e. the product of Example 5, Step B, 1.00 g, 3.5 mmol) in a 10 mL microwave vial with a star-shaped stir bar. The vessel was sealed and allowed to react in the microwave at 140° C. for 10 min. A white solid formed upon cooling to ambient temperature. Dioxane (5 mL) was added, then excess solvent was removed under reduced pressure. Aqueous hydrochloric acid (1 N, 10 mL) was then added and the resulting white solid was filtered with water with 2% hexane and dried on the frit to give 0.89 g of the title compound. M.S.=275 (AP$^+$).

By the procedures described herein together with methods known in the art, the following compounds of Tables 1 to 271 can be prepared. The following abbreviations are used in the Tables which follow: t means tertiary, i means iso, Me means methyl, Et means ethyl, i-Pr means isopropyl, Bu means butyl, c-Pr cyclopropyl, and OMe means methoxy, OEt means ethoxy, —CN means cyano. Unless otherwise indicated in the following Tables each of $X^1$, $X^2$, $X^3$, $X^4$, $X^5$, $X^6$, $X^7$, $X^8$, $X^9$ and $X^{10}$ is CH.

TABLE 1

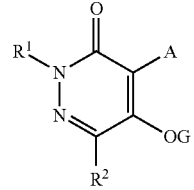

$R^1$ is CH$_3$, $R^2$ is CH$_3$, G is H and A is

A-1 ($Y^1$ is S)
A-1 ($Y^1$ is S, $X^1$ is CCH$_3$)
A-1 ($Y^1$ is S, $X^1$ is CCH$_3$, $X^3$ is CCl)
A-1 ($Y^1$ is S, $X^1$ is CCl)
A-1 ($Y^1$ is S, $X^3$ is CCl)
A-1 ($Y^1$ is S, $X^3$ is CBr)
A-1 ($Y^1$ is S, $X^3$ is CF)
A-1 ($Y^1$ is S, $X^1$ is CCH$_3$, $X^5$ is CCl)
A-1 ($Y^1$ is S, $X^1$ is CCH$_3$ $X^5$ is CCH$_3$)
A-1 ($Y^1$ is S, $X^1$ is CCl, $X^5$ is CCH$_3$)
A-1 ($Y^1$ is S, $X^3$ is CCl, $X^5$ is CCH$_3$)
A-1 ($Y^1$ is S, $X^1$ is CCH$_3$, $X^3$ is CCl, $X^5$ is CCH$_3$)
A-1 ($Y^1$ is O)
A-1 ($Y^1$ is O, $X^1$ is CCH$_3$)
A-1 ($Y^1$ is O, $X^1$ is CCH$_3$, $X^3$ is CCl)
A-1 ($Y^1$ is O, $X^1$ is CCl)
A-1 ($Y^1$ is O, $X^3$ is CCl)
A-1 ($Y^1$ is O, $X^3$ is CBr)
A-1 ($Y^1$ is O, $X^3$ is CF)
A-1 ($Y^1$ is O, $X^1$ is Cl, $X^3$ is CCl)
A-1 ($Y^1$ is O, $X^1$ is CCH$_3$, $X^5$ is CCl)
A-1 ($Y^1$ is O, $X^1$ is CCH$_3$, $X^5$ is CCH$_3$)
A-1 ($Y^1$ is O, $X^1$ is CCH$_3$, $X^3$ is CCl, $X^5$ is CCH$_3$)
A-1 ($Y^1$ is O, $X^3$ is CCl, $X^5$ is CCH$_3$)
A-1 ($Y^1$ is O, $X^3$ is CCl, $X^5$ is CCl)
A-1 ($Y^1$ is S, $X^5$ is N)
A-1 ($Y^1$ is O, $X^5$ is N)
A-1 ($Y^1$ is S, $X^6$ is N)
A-1 ($Y^1$ is O, $X^6$ is N)
A-1 ($Y^1$ is NCH$_3$)
A-1 ($Y^1$ is NCH$_3$, $X^6$ is N)
A-1 ($Y^1$ is S, $X^1$ is N)
A-1 ($Y^1$ is S, $X^2$ is N)
A-1 ($Y^1$ is S, $X^3$ is N)
A-1 ($Y^1$ is O, $X^1$ is N)
A-1 ($Y^1$ is O, $X^2$ is N)
A-1 ($Y^1$ is O, $X^3$ is N)
A-1 ($Y^1$ is NCH$_3$, $X^5$ is N)
A-1 ($Y^1$ is NCH$_3$, $X^5$ is N, $X^6$ is N)
A-2 ($Y^2$ is S)
A-2 ($Y^2$ is S, $X^1$ is CCl)
A-2 ($Y^2$ is S, $X^1$ is CCH$_3$)
A-2 ($Y^2$ is S, $X^3$ is CCl)
A-2 ($Y^2$ is S, $X^3$ is CBr)
A-2 ($Y^2$ is S, $X^3$ is CF)
A-2 ($Y^2$ is S, $X^1$ is CCH$_3$, $X^3$ is CCl)
A-2 ($Y^2$ is O)
A-2 ($Y^2$ is O, $X^1$ is CCH$_3$)
A-2 ($Y^2$ is O, $X^1$ is CCH$_3$, $X^3$ is CCl)
A-2 ($Y^2$ is O, $X^1$ is CCl)
A-2 ($Y^2$ is O, $X^3$ is CCl)
A-2 ($Y^2$ is O, $X^3$ is CBr)
A-2 ($Y^2$ is O, $X^3$ is CF)
A-2 ($Y^2$ is O, $X^1$ is CCl, $X^3$ is CCl)
A-2 ($Y^2$ is O, $X^1$ is CCH$_3$, $X^5$ is CCl)
A-2 ($Y^2$ is O, $X^1$ is CCH$_3$, $X^5$ is CCH$_3$)
A-2 ($Y^2$ is O, $X^1$ is CCH$_3$, $X^3$ is CCl, $X^5$ is CCH$_3$)
A-2 ($Y^2$ is O, $X^3$ is CCl, $X^5$ is CCH$_3$)
A-2 ($Y^2$ is O, $X^3$ is CCl, $X^5$ is CCl)
A-2 ($Y^2$ is S, $X^5$ is N)
A-2 ($Y^2$ is O, $X^5$ is N)
A-2 ($Y^2$ is S, $X^4$ is N)
A-2 ($Y^2$ is O, $X^4$ is N)
A-2 ($Y^2$ is NCH$_3$)

TABLE 1-continued

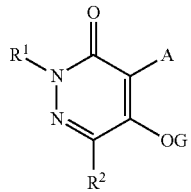

R¹ is CH₃, R² is CH₃, G is H and A is

A-2 (Y² is NCH₃, X⁴ is N)
A-2 (Y² is S, X¹ is N)
A-2 (Y² is S, X² is N)
A-2 (Y² is S, X³ is N)
A-2 (Y² is NCH₃, X⁴ is N)
A-2 (Y² is NCH₃, X⁵ is N, X⁴ is N)
A-3 (X¹ is N)
A-3 (X¹ is N, X³ is CCl)
A-3 (X¹ is N, X³ is COMe)
A-3 (X¹ is N, X³ is CCH₃)
A-3 (X² is N)*
A-3 (X² is N, X³ is CCl)
A-3 (X² is N, X³ is COMe)
A-3 (X² is N, X³ is CCH₃)
A-3 (X³ is N)*
A-3 (X³ is N, X¹ is CCl)
A-3 (X³ is N, X¹ is COMe)
A-3 (X³ is N, X¹ is CCH₃)
A-3 (X³ is N, X⁹ is CCl)
A-3 (X³ is N, X¹ is CCH₃, X⁹ is CCl)
A-3 (X⁷ is N)*
A-3 (X⁷ is N, X³ is CCl)
A-3 (X⁷ is N, X³ is COMe)
A-3 (X⁷ is N, X³ is CCH₃)
A-3 (X⁷ is N, X¹ is CCH₃)
A-3 (X⁸ is N)*
A-3 (X⁸ is N, X³ is CCl)
A-3 (X⁸ is N, X³ is COMe)
A-3 (X⁸ is N, X³ is CCH₃)
A-3 (X⁸ is N, X¹ is CCH₃)
A-3 (X⁹ is N)*
A-3 (X⁹ is N, X³ is CCl)
A-3 (X⁹ is N, X³ is COMe)
A-3 (X⁹ is N, X³ is CCH₃)
A-3 (X⁹ is N, X¹ is CCH₃)
A-3 (X¹⁰ is N)
A-3 (X¹⁰ is N, X³ is CCl)
A-3 (X¹⁰ is N, X³ is COMe)
A-3 (X¹⁰ is N, X³ is CCH₃)
A-3 (X¹⁰ is N, X¹ is CCH₃)
A-3 (X¹ is N, X³ is N)
A-3 (X¹ is N, X² is N)
A-3 (X¹ is N, X² is N, X³ is CCl)
A-3 (X¹ is N, X² is N, X³ is CCH₃)
A-3 (X² is N, X³ is N)
A-3 (X⁸ is N, X¹⁰ is N)
A-3 (X⁹ is N, X¹⁰ is N)
A-3 (X⁷ is N, X¹⁰ is N)
A-3 (X⁷ is N, X¹⁰ is N, X³ is CCl)
A-3 (X⁷ is N, X¹⁰ is N, X³ is CCH₃)
A-3 (X⁷ is N, X⁹ is N)
A-3 (X⁷ is N, X⁸ is N)
A-3 (X⁷ is N, X⁸ is N)
A-3 (X¹ is N, X⁸ is N, X³ is CCl)
A-3 (X¹ is N, X⁸ is N, X³ is CCH₃)
A-3 (X¹ is N, X⁷ is N)
A-3 (X¹ is N, X⁸ is N)
A-3 (X¹ is N, X⁸ is N)
A-3 (X¹ is N, X¹⁰ is N)
A-3 (X² is N, X¹⁰ is N)
A-3 (X² is N, X⁹ is N)
A-3 (X² is N, X⁸ is N)
A-3 (X² is N, X⁸ is N)
A-3 (X² is N, X⁷ is N)
A-3 (X³ is N, X¹⁰ is N)
A-3 (X³ is N, X⁹ is N)
A-3 (X³ is N, X⁸ is N)
A-3 (X³ is N, X⁷ is N)

TABLE 1-continued

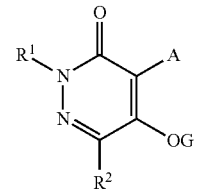

R¹ is CH₃, R² is CH₃, G is H and A is

A-4 (Y⁴ is S, X¹⁰ is N)
A-4 (Y⁴ is S, X⁹ is N)
A-4 (Y⁴ is S, X⁸ is N)
A-4 (Y⁴ is S, X⁷ is N)
A-4 (Y⁴ is O, X¹⁰ is N)
A-4 (Y⁴ is O, X⁹ is N)
A-4 (Y⁴ is O, X⁸ is N)
A-4 (Y⁴ is O, X⁷ is N)
A-4 (Y⁴ is NCH₃, X¹⁰ is N)
A-4 (Y⁴ is NCH₃, X⁹ is N)
A-4 (Y⁴ is NCH₃, X⁸ is N)
A-4 (Y⁴ is NCH₃, X⁷ is N)
A-4 (Y⁴ is NCH₃, X¹ is N, X¹⁰ is N)
A-4 (Y⁴ is NCH₃, X¹ is N, X⁹ is N)
A-4 (Y⁴ is NCH₃, X¹ is N, X⁸ is N)
A-4 (Y⁴ is NCH₃, X¹ is N, X⁷ is N)

*Does not apply to Tables 47, 49, 56 and 58.

Table 2 is constructed in the same manner as Table 1 except that the Row Heading (i.e. "R¹ is CH₃, R² is CH₃, G is H and A is" is replaced with the Row Heading listed for Table 2 below (i.e. "R¹ is Me, R² is Me, and G is C(O)Me."). Therefore the first entry in Table 2 is a compound of Formula 1 wherein W is O, A is A-1 (Y¹ is S, X¹ is CH, X² is CH, X³ is CH, X⁵ is CH, X⁶ is CH), R¹ is Me, R² is Me, and G is C(O)Me. Tables 3 through 288 are constructed similarly.

| Table | Row Heading |
|---|---|
| 2 | R¹ is Me, R² is Me, and G is C(O)Me. |
| 3 | R¹ is Me, R² is Me, and G is C(O)Et. |
| 4 | R¹ is Me, R² is Me, and G is C(O)—i-Pr. |
| 5 | R¹ is Me, R² is Me, and G is C(O)—Ph. |
| 6 | R¹ is Me, R² is Me, and G is CO₂Me. |
| 7 | R¹ is Me, R² is Me, and G is CO₂Et. |
| 8 | R¹ is Me, R² is Me, and G is CO₂—i-Pr. |
| 9 | R¹ is Me, R² is Me, and G is CH₂OMe |
| 10 | R¹ is Me, R² is Me, and G is SO₂Me. |
| 11 | R¹ is Me, R² is H, and G is C(O)Me. |
| 12 | R¹ is Me, R² is H, and G is C(O)Et. |
| 13 | R¹ is Me, R² is H, and G is H. |
| 14 | R¹ is Me, R² is H, and G is C(O)—Ph |
| 15 | R¹ is Me, R² is H, and G is CO₂Me. |
| 16 | R¹ is Me, R² is H, and G is CO₂Et. |
| 17 | R¹ is Me, R² is H, and G is CO₂—i-Pr. |
| 18 | R¹ is Me, R² is H, and G is CH₂OMe |
| 19 | R¹ is Me, R² is H, and G is SO₂Me. |
| 20 | R¹ is Me, R² is Et, and G is C(O)Me. |
| 21 | R¹ is Me, R² is Et, and G is C(O)Et. |
| 22 | R¹ is Me, R² is Et, and G is H. |
| 23 | R¹ is Me, R² is Et, and G is C(O)—Ph |
| 24 | R¹ is Me, R² is Et, and G is CO₂Me. |
| 25 | R¹ is Me, R² is Et, and G is CO₂Et. |
| 26 | R¹ is Me, R² is Et, and G is CO₂—i-Pr. |
| 27 | R¹ is Me, R² is Et, and G is CH₂OMe |
| 28 | R¹ is Me, R² is Et, and G is SO₂Me. |
| 29 | R¹ is Me, R² is Pr, and G is C(O)Me. |
| 30 | R¹ is Me, R² is Pr, and G is C(O)Et. |
| 31 | R¹ is Me, R² is Pr, and G is H |
| 32 | R¹ is Me, R² is Pr, and G is C(O)—Ph |
| 33 | R¹ is Me, R² is Pr, and G is CO₂Me. |
| 34 | R¹ is Me, R² is Pr, and G is CO₂Et. |
| 35 | R¹ is Me, R² is Pr, and G is CO₂—i-Pr. |
| 36 | R¹ is Me, R² is Pr, and G is CO₂—t-Bu. |

-continued

| Table | Row Heading |
|---|---|
| 37 | $R^1$ is Me, $R^2$ is Pr, and G is $SO_2Me$. |
| 38 | $R^1$ is Me, $R^2$ is $CF_3$, and G is $C(O)Me$. |
| 39 | $R^1$ is Me, $R^2$ is $CF_3$, and G is $C(O)Et$. |
| 40 | $R^1$ is Me, $R^2$ is $CF_3$, and G is H. |
| 41 | $R^1$ is Me, $R^2$ is $CF_3$, and G is $C(O)$—Ph. |
| 42 | $R^1$ is Me, $R^2$ is $CF_3$, and G is $CO_2Me$. |
| 43 | $R^1$ is Me, $R^2$ is $CF_3$, and G is $CO_2Et$. |
| 44 | $R^1$ is Me, $R^2$ is $CF_3$, and G is $CO_2$—i-Pr. |
| 45 | $R^1$ is Me, $R^2$ is $CF_3$, and G is $CH_2OMe$. |
| 46 | $R^1$ is Me, $R^2$ is $CF_3$, and G is $SO_2Me$. |
| 47 | $R^1$ is Me, $R^2$ is Cl, and G is $C(O)Me$. |
| 48 | $R^1$ is Me, $R^2$ is Cl, and G is $C(O)Et$. |
| 49 | $R^1$ is Me, $R^2$ is Cl, and G is H. |
| 50 | $R^1$ is Me, $R^2$ is Cl, and G is $C(O)$—Ph. |
| 51 | $R^1$ is Me, $R^2$ is Cl, and G is $CO_2Me$. |
| 52 | $R^1$ is Me, $R^2$ is Cl, and G is $CO_2Et$. |
| 53 | $R^1$ is Me, $R^2$ is Cl, and G is $CO_2$—i-Pr. |
| 54 | $R^1$ is Me, $R^2$ is Cl, and G is $CH_2OMe$. |
| 55 | $R^1$ is Me, $R^2$ is Cl, and G is $SO_2Me$. |
| 56 | $R^1$ is Me, $R^2$ is Br, and G is $C(O)Me$. |
| 57 | $R^1$ is Me, $R^2$ is Br, and G is $C(O)Et$. |
| 58 | $R^1$ is Me, $R^2$ is Br, and G is H. |
| 59 | $R^1$ is Me, $R^2$ is Br, and G is $C(O)$—Ph. |
| 60 | $R^1$ is Me, $R^2$ is Br, and G is $CO_2Me$. |
| 61 | $R^1$ is Me, $R^2$ is Br, and G is $CO_2Et$. |
| 62 | $R^1$ is Me, $R^2$ is Br, and G is $CO_2$—i-Pr. |
| 63 | $R^1$ is Me, $R^2$ is Br, and G is $CH_2OMe$. |
| 64 | $R^1$ is Me, $R^2$ is Br, and G is $SO_2Me$. |
| 65 | $R^1$ is Me, $R^2$ is I, and G is $C(O)Me$. |
| 66 | $R^1$ is Me, $R^2$ is I, and G is $C(O)Et$. |
| 67 | $R^1$ is Me, $R^2$ is I, and G is H. |
| 68 | $R^1$ is Me, $R^2$ is I, and G is C $C(O)$—Ph. |
| 69 | $R^1$ is Me, $R^2$ is I, and G is $CO_2Me$. |
| 70 | $R^1$ is Me, $R^2$ is I, and G is $CO_2Et$. |
| 71 | $R^1$ is Me, $R^2$ is I, and G is $CO_2$—i-Pr. |
| 72 | $R^1$ is Me, $R^2$ is I, and G is $CH_2OMe$. |
| 73 | $R^1$ is Me, $R^2$ is I, and G is $SO_2Me$. |
| 74 | $R^1$ is Me, $R^2$ is OMe, and G is $C(O)Me$. |
| 75 | $R^1$ is Me, $R^2$ is OMe, and G is $C(O)Et$. |
| 76 | $R^1$ is Me, $R^2$ is OMe, and G is H. |
| 77 | $R^1$ is Me, $R^2$ is OMe, and G is $C(O)$—Ph. |
| 78 | $R^1$ is Me, $R^2$ is OMe, and G is $CO_2Me$. |
| 79 | $R^1$ is Me, $R^2$ is OMe, and G is $CO_2Et$. |
| 80 | $R^1$ is Me, $R^2$ is OMe, and G is $CO_2$—i-Pr. |
| 81 | $R^1$ is Me, $R^2$ is OMe, and G is $CH_2OMe$. |
| 82 | $R^1$ is Me, $R^2$ is OMe, and G is $SO_2Me$. |
| 83 | $R^1$ is Me, $R^2$ is OEt, and G is $C(O)Me$. |
| 84 | $R^1$ is Me, $R^2$ is OEt, and G is $C(O)Et$. |
| 85 | $R^1$ is Me, $R^2$ is OEt, and G is H. |
| 86 | $R^1$ is Me, $R^2$ is OEt, and G is $C(O)$—Ph. |
| 87 | $R^1$ is Me, $R^2$ is OEt, and G is $CO_2Me$. |
| 88 | $R^1$ is Me, $R^2$ is OEt, and G is $CO_2Et$. |
| 89 | $R^1$ is Me, $R^2$ is OEt, and G is $CO_2$—i-Pr. |
| 90 | $R^1$ is Me, $R^2$ is OEt, and G is $CH_2OMe$. |
| 91 | $R^1$ is Me, $R^2$ is OEt, and G is $SO_2Me$. |
| 92 | $R^1$ is Et, $R^2$ is Me, and G is $C(O)Me$. |
| 93 | $R^1$ is Et, $R^2$ is Me, and G is $C(O)Et$. |
| 94 | $R^1$ is Et, $R^2$ is Me, and G is H. |
| 95 | $R^1$ is Et, $R^2$ is Me, and G is $C(O)$—Ph. |
| 96 | $R^1$ is Et, $R^2$ is Me, and G is $CO_2Me$. |
| 97 | $R^1$ is Et, $R^2$ is Me, and G is $CO_2Et$. |
| 98 | $R^1$ is Et, $R^2$ is Me, and G is $CO_2$—i-Pr. |
| 99 | $R^1$ is Et, $R^2$ is Me, and G is $CH_2OMe$. |
| 100 | $R^1$ is Et, $R^2$ is Me, and G is $SO_2Me$. |
| 101 | $R^1$ is Et, $R^2$ is H, and G is $C(O)Me$. |
| 102 | $R^1$ is Et, $R^2$ is H, and G is $C(O)Et$. |
| 103 | $R^1$ is Et, $R^2$ is H, and G is H. |
| 104 | $R^1$ is Et, $R^2$ is H, and G is $C(O)$—Ph. |
| 105 | $R^1$ is Et, $R^2$ is H, and G is $CO_2Me$. |
| 106 | $R^1$ is Et, $R^2$ is H, and G is $CO_2Et$. |
| 107 | $R^1$ is Et, $R^2$ is H, and G is $CO_2$—i-Pr. |
| 108 | $R^1$ is Et, $R^2$ is H, and G is $CH_2OMe$. |
| 109 | $R^1$ is Et, $R^2$ is H, and G is $SO_2Me$. |
| 110 | $R^1$ is Et, $R^2$ is Et, and G is $C(O)Me$. |
| 111 | $R^1$ is Et, $R^2$ is Et, and G is $C(O)Et$. |
| 112 | $R^1$ is Et, $R^2$ is Et, and G is H. |
| 113 | $R^1$ is Et, $R^2$ is Et, and G is $C(O)$—Ph. |
| 114 | $R^1$ is Et, $R^2$ is Et, and G is $CO_2Me$. |
| 115 | $R^1$ is Et, $R^2$ is Et, and G is $CO_2Et$. |
| 116 | $R^1$ is Et, $R^2$ is Et, and G is $CH_2OMe$. |
| 117 | $R^1$ is Et, $R^2$ is Et, and G is $CO_2$—t-Bu. |
| 118 | $R^1$ is Et, $R^2$ is Et, and G is $SO_2Me$. |
| 119 | $R^1$ is Et, $R^2$ is Pr, and G is $C(O)Me$. |
| 120 | $R^1$ is Et, $R^2$ is Pr, and G is $C(O)Et$. |
| 121 | $R^1$ is Et, $R^2$ is Pr, and G is H. |
| 122 | $R^1$ is Et, $R^2$ is Pr, and G is $C(O)$—Ph. |
| 123 | $R^1$ is Et, $R^2$ is Pr, and G is $CO_2Me$. |
| 124 | $R^1$ is Et, $R^2$ is Pr, and G is $CO_2Et$. |
| 125 | $R^1$ is Et, $R^2$ is Pr, and G is $CO_2$—i-Pr. |
| 126 | $R^1$ is Et, $R^2$ is Pr, and G is $CH_2OMe$. |
| 127 | $R^1$ is Et, $R^2$ is Pr, and G is $SO_2Me$. |
| 128 | $R^1$ is Et, $R^2$ is $CF_3$, and G is $C(O)Me$. |
| 129 | $R^1$ is Et, $R^2$ is $CF_3$, and G is $C(O)Et$. |
| 130 | $R^1$ is Et, $R^2$ is $CF_3$, and G is H. |
| 131 | $R^1$ is Et, $R^2$ is $CF_3$, and G is $C(O)$—Ph. |
| 132 | $R^1$ is Et, $R^2$ is $CF_3$, and G is $CO_2Me$. |
| 133 | $R^1$ is Et, $R^2$ is $CF_3$, and G is $CO_2Et$. |
| 134 | $R^1$ is Et, $R^2$ is $CF_3$, and G is $CO_2$—i-Pr. |
| 135 | $R^1$ is Et, $R^2$ is $CF_3$, and G is $CH_2OMe$. |
| 136 | $R^1$ is Et, $R^2$ is $CF_3$, and G is $SO_2Me$. |
| 137 | $R^1$ is Et, $R^2$ is Cl, and G is $C(O)Me$. |
| 138 | $R^1$ is Et, $R^2$ is Cl, and G is $C(O)Et$. |
| 139 | $R^1$ is Et, $R^2$ is Cl, and G is H. |
| 140 | $R^1$ is Et, $R^2$ is Cl, and G is $C(O)$—Ph. |
| 141 | $R^1$ is Et, $R^2$ is Cl, and G is $CO_2Me$. |
| 142 | $R^1$ is Et, $R^2$ is Cl, and G is $CO_2Et$. |
| 143 | $R^1$ is Et, $R^2$ is Cl, and G is $CO_2$—i-Pr. |
| 144 | $R^1$ is Et, $R^2$ is Cl, and G is $CH_2OMe$. |
| 145 | $R^1$ is Et, $R^2$ is Cl, and G is $SO_2Me$. |
| 146 | $R^1$ is Et, $R^2$ is Br, and G is $C(O)Me$. |
| 147 | $R^1$ is Et, $R^2$ is Br, and G is $C(O)Et$. |
| 148 | $R^1$ is Et, $R^2$ is Br, and G is H. |
| 149 | $R^1$ is Et, $R^2$ is Br, and G is $C(O)$—Ph. |
| 150 | $R^1$ is Et, $R^2$ is Br, and G is $CO_2Me$. |
| 151 | $R^1$ is Et, $R^2$ is Br, and G is $CO_2Et$. |
| 152 | $R^1$ is Et, $R^2$ is Br, and G is $CO_2$—i-Pr. |
| 153 | $R^1$ is Et, $R^2$ is Br, and G is $CH_2OMe$. |
| 154 | $R^1$ is Et, $R^2$ is Br, and G is $SO_2Me$. |
| 155 | $R^1$ is Et, $R^2$ is I, and G is $C(O)Me$. |
| 156 | $R^1$ is Et, $R^2$ is I, and G is $C(O)Et$. |
| 157 | $R^1$ is Et, $R^2$ is I, and G is H. |
| 158 | $R^1$ is Et, $R^2$ is I, and G is $C(O)$—Ph. |
| 159 | $R^1$ is Et, $R^2$ is I, and G is $CO_2Me$. |
| 160 | $R^1$ is Et, $R^2$ is I, and G is $CO_2Et$. |
| 161 | $R^1$ is Et, $R^2$ is I, and G is $CO_2$—i-Pr. |
| 162 | $R^1$ is Et, $R^2$ is I, and G is $CH_2OMe$. |
| 163 | $R^1$ is Et, $R^2$ is I, and G is $SO_2Me$. |
| 164 | $R^1$ is Et, $R^2$ is OMe, and G is $C(O)Me$. |
| 165 | $R^1$ is Et, $R^2$ is OMe, and G is $C(O)Et$. |
| 166 | $R^1$ is Et, $R^2$ is OMe, and G is H. |
| 167 | $R^1$ is Et, $R^2$ is OMe, and G is $C(O)$—Ph. |
| 168 | $R^1$ is Et, $R^2$ is OMe, and G is $CO_2Me$. |
| 169 | $R^1$ is Et, $R^2$ is OMe, and G is $CO_2Et$. |
| 170 | $R^1$ is Et, $R^2$ is OMe, and G is $CO_2$—i-Pr. |
| 171 | $R^1$ is Et, $R^2$ is OMe, and G is $CH_2OMe$. |
| 172 | $R^1$ is Et, $R^2$ is OMe, and G is $SO_2Me$. |
| 173 | $R^1$ is Et, $R^2$ is OEt, and G is $C(O)Me$. |
| 174 | $R^1$ is Et, $R^2$ is OEt, and G is $C(O)Et$. |
| 175 | $R^1$ is Et, $R^2$ is OEt, and G is H. |
| 176 | $R^1$ is Et, $R^2$ is OEt, and G is $C(O)$—Ph. |
| 177 | $R^1$ is Et, $R^2$ is OEt, and G is $CO_2Me$. |
| 178 | $R^1$ is Et, $R^2$ is OEt, and G is $CO_2Et$. |
| 179 | $R^1$ is Et, $R^2$ is OEt, and G is $CO_2$—i-Pr. |
| 180 | $R^1$ is Et, $R^2$ is OEt, and G is $CH_2OMe$. |
| 181 | $R^1$ is Et, $R^2$ is OEt, and G is $SO_2Me$. |
| 182 | $R^1$ is Pr, $R^2$ is Me, and G is $C(O)Me$. |
| 183 | $R^1$ is Pr, $R^2$ is Me, and G is $C(O)Et$. |
| 184 | $R^1$ is Pr, $R^2$ is Me, and G is H. |
| 185 | $R^1$ is Pr, $R^2$ is Me, and G is $C(O)$—Ph. |
| 186 | $R^1$ is Pr, $R^2$ is Me, and G is $CO_2Me$. |
| 187 | $R^1$ is Pr, $R^2$ is Me, and G is $CO_2Et$. |
| 188 | $R^1$ is Pr, $R^2$ is Me, and G is $CO_2$—i-Pr. |
| 189 | $R^1$ is Pr, $R^2$ is Me, and G is $CH_2OMe$. |
| 190 | $R^1$ is Pr, $R^2$ is Me, and G is $SO_2Me$. |

| Table | Row Heading |
|---|---|
| 191 | $R^1$ is Pr, $R^2$ is H, and G is C(O)Me. |
| 192 | $R^1$ is Pr, $R^2$ is H, and G is C(O)Et. |
| 193 | $R^1$ is Pr, $R^2$ is H, and G is H. |
| 194 | $R^1$ is Pr, $R^2$ is H, and G is C(O)—Ph |
| 195 | $R^1$ is Pr, $R^2$ is H, and G is $CO_2$Me. |
| 196 | $R^1$ is Pr, $R^2$ is H, and G is $CO_2$Et. |
| 197 | $R^1$ is Pr, $R^2$ is H, and G is $CO_2$—i-Pr. |
| 198 | $R^1$ is Pr, $R^2$ is H, and G is $CH_2$OMe |
| 199 | $R^1$ is Pr, $R^2$ is H, and G is $SO_2$Me. |
| 200 | $R^1$ is Pr, $R^2$ is Et, and G is C(O)Me. |
| 201 | $R^1$ is Pr, $R^2$ is Et, and G is C(O)Et. |
| 202 | $R^1$ is Pr, $R^2$ is Et, and G is H. |
| 203 | $R^1$ is Pr, $R^2$ is Et, and G is C(O)—Ph |
| 204 | $R^1$ is Pr, $R^2$ is Et, and G is $CO_2$Me. |
| 205 | $R^1$ is Pr, $R^2$ is Et, and G is $CO_2$Et. |
| 206 | $R^1$ is Pr, $R^2$ is Et, and G is $CO_2$—i-Pr. |
| 207 | $R^1$ is Pr, $R^2$ is Et, and G is $CH_2$OMe |
| 208 | $R^1$ is Pr, $R^2$ is Et, and G is $SO_2$Me. |
| 209 | $R^1$ is Pr, $R^2$ is Pr, and G is C(O)Me. |
| 210 | $R^1$ is Pr, $R^2$ is Pr, and G is C(O)Et. |
| 211 | $R^1$ is Pr, $R^2$ is Pr, and G is H. |
| 212 | $R^1$ is Pr, $R^2$ is Pr, and G is C(O)—Ph. |
| 213 | $R^1$ is Pr, $R^2$ is Pr, and G is $CO_2$Me. |
| 214 | $R^1$ is Pr, $R^2$ is Pr, and G is $CO_2$Et. |
| 215 | $R^1$ is Pr, $R^2$ is Pr, and G is $CO_2$—i-Pr. |
| 216 | $R^1$ is Pr, $R^2$ is Pr, and G is $CH_2$OMe |
| 217 | $R^1$ is Pr, $R^2$ is Pr, and G is $SO_2$Me. |
| 218 | $R^1$ is Pr, $R^2$ is $CF_3$, and G is C(O)Me. |
| 219 | $R^1$ is Pr, $R^2$ is $CF_3$, and G is C(O)Et. |
| 220 | $R^1$ is Pr, $R^2$ is $CF_3$, and G is H. |
| 221 | $R^1$ is Pr, $R^2$ is $CF_3$, and G is C(O)—Ph |
| 222 | $R^1$ is Pr, $R^2$ is $CF_3$, and G is $CO_2$Me. |
| 223 | $R^1$ is Pr, $R^2$ is $CF_3$, and G is $CO_2$Et. |
| 224 | $R^1$ is Pr, $R^2$ is $CF_3$, and G is $CO_2$—i-Pr. |
| 225 | $R^1$ is Pr, $R^2$ is $CF_3$, and G is $CH_2$OMe |
| 226 | $R^1$ is Pr, $R^2$ is $CF_3$, and G is $SO_2$Me. |
| 227 | $R^1$ is Pr, $R^2$ is Cl, and G is C(O)Me. |
| 228 | $R^1$ is Pr, $R^2$ is Cl, and G is C(O)Et. |
| 229 | $R^1$ is Pr, $R^2$ is Cl, and G is H. |
| 230 | $R^1$ is Pr, $R^2$ is Cl, and G is C(O)—Ph |
| 231 | $R^1$ is Pr, $R^2$ is Cl, and G is $CO_2$Me. |
| 232 | $R^1$ is Pr, $R^2$ is Cl, and G is $CO_2$Et. |
| 233 | $R^1$ is Pr, $R^2$ is Cl, and G is $CO_2$—i-Pr. |
| 234 | $R^1$ is Pr, $R^2$ is Cl, and G is $CH_2$OMe |
| 235 | $R^1$ is Pr, $R^2$ is Cl, and G is $SO_2$Me. |
| 236 | $R^1$ is Pr, $R^2$ is Br, and G is C(O)Me. |
| 237 | $R^1$ is Pr, $R^2$ is Br, and G is C(O)Et. |
| 238 | $R^1$ is Pr, $R^2$ is Br, and G is H. |
| 239 | $R^1$ is Pr, $R^2$ is Br, and G is C(O)—Ph |
| 240 | $R^1$ is Pr, $R^2$ is Br, and G is $CO_2$Me. |
| 241 | $R^1$ is Pr, $R^2$ is Br, and G is $CO_2$Et. |
| 242 | $R^1$ is Pr, $R^2$ is Br, and G is $CO_2$—i-Pr. |
| 243 | $R^1$ is Pr, $R^2$ is Br, and G is $CH_2$OMe |
| 244 | $R^1$ is Pr, $R^2$ is Br, and G is $SO_2$Me. |
| 245 | $R^1$ is Pr, $R^2$ is I, and G is C(O)Me. |
| 246 | $R^1$ is Pr, $R^2$ is I, and G is C(O)Et. |
| 247 | $R^1$ is Pr, $R^2$ is I, and G is H. |
| 248 | $R^1$ is Pr, $R^2$ is I, and G is C(O)—Ph |
| 249 | $R^1$ is Pr, $R^2$ is I, and G is $CO_2$Me. |
| 250 | $R^1$ is Pr, $R^2$ is I, and G is $CO_2$Et. |
| 251 | $R^1$ is Pr, $R^2$ is I, and G is $CO_2$—i-Pr. |
| 252 | $R^1$ is Pr, $R^2$ is I, and G is $CH_2$OMe |
| 253 | $R^1$ is Pr, $R^2$ is I, and G is $SO_2$Me. |
| 254 | $R^1$ is Pr, $R^2$ is OMe, and G is C(O)Me. |
| 255 | $R^1$ is Pr, $R^2$ is OMe, and G is C(O)Et. |
| 256 | $R^1$ is Pr, $R^2$ is OMe, and G is H. |
| 257 | $R^1$ is Pr, $R^2$ is OMe, and G is C(O)—Ph |
| 258 | $R^1$ is Pr, $R^2$ is OMe, and G is $CO_2$Me. |
| 259 | $R^1$ is Pr, $R^2$ is OMe, and G is $CO_2$Et. |
| 260 | $R^1$ is Pr, $R^2$ is OMe, and G is $CO_2$—i-Pr. |
| 261 | $R^1$ is Pr, $R^2$ is OMe, and G is $CH_2$OMe. |
| 262 | $R^1$ is Pr, $R^2$ is OMe, and G is $SO_2$Me. |
| 263 | $R^1$ is Pr, $R^2$ is OEt, and G is C(O)Me. |
| 264 | $R^1$ is Pr, $R^2$ is OEt, and G is C(O)Et. |
| 265 | $R^1$ is Pr, $R^2$ is OEt, and G is H. |
| 266 | $R^1$ is Pr, $R^2$ is OEt, and G is C(O)—Ph |
| 267 | $R^1$ is Pr, $R^2$ is OEt, and G is $CO_2$Me. |
| 268 | $R^1$ is Pr, $R^2$ is OEt, and G is $CO_2$Et. |
| 269 | $R^1$ is Pr, $R^2$ is OEt, and G is $CO_2$—i-Pr. |
| 270 | $R^1$ is Pr, $R^2$ is OEt, and G is $CH_2$OMe |
| 271 | $R^1$ is Pr, $R^2$ is OEt, and G is $SO_2$Me. |
| 272 | $R^1$ is propargyl, $R^2$ is Me, and G is C(O)Me. |
| 273 | $R^1$ is propargyl, $R^2$ is Me, and G is C(O)Et. |
| 274 | $R^1$ is propargyl, $R^2$ is Me, and G is C(O)Ph. |
| 275 | $R^1$ is propargyl, $R^2$ is Me, and G is H |
| 276 | $R^1$ is propargyl, $R^2$ is Me, and G is $CO_2$Me. |
| 277 | $R^1$ is propargyl, $R^2$ is Me, and G is $CO_2$Et. |
| 278 | $R^1$ is propargyl, $R^2$ is Me, and G is $CO_2$—i-Pr. |
| 279 | $R^1$ is propargyl, $R^2$ is Me, and G is $CH_2$OMe |
| 280 | $R^1$ is propargyl, $R^2$ is Me, and G is $SO_2$Me. |
| 281 | $R^1$ is allyl, $R^2$ is Me, and G is C(O)Me. |
| 282 | $R^1$ is allyl, $R^2$ is Me, and G is C(O)Et. |
| 283 | $R^1$ is allyl, $R^2$ is Me, and G is $CO_2$Me. |
| 284 | $R^1$ is allyl, $R^2$ is Me, and G is H |
| 285 | $R^1$ is c-Pr, $R^2$ is Me, and G is C(O)Me. |
| 286 | $R^1$ is c-Pr, $R^2$ is Me, and G is C(O)Et. |
| 287 | $R^1$ is c-Pr, $R^2$ is Me, and G is $CO_2$Me. |
| 288 | $R^1$ is c-Pr, $R^2$ is Me, and G is H |
| 285 | $R^1$ is Me, $R^2$ is —CN, and G is C(O)Me. |
| 286 | $R^1$ is Me, $R^2$ is —CN, and G is C(O)Et. |
| 287 | $R^1$ is Me, $R^2$ is —CN, and G is $CO_2$Me. |
| 288 | $R^1$ is Me, $R^2$ is —CN, and G is H |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48; *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
| --- | --- |
| Compound 1 | 98.5% |
| silica aerogel | 0.5% |
| synthetic amorphous fine silica | 1.0% |

Example B

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
| --- | --- |
| Compound 1 | 10.0% |
| attapulgite granules (low volatile matter, 0.71/0.30 mm; U.S.S. No. 25-50 sieves) | 90.0% |

Example D

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
| --- | --- |
| Compound 1 | 10.0% |
| polyoxyethylene sorbitol hexoleate | 20.0% |
| $C_6$-$C_{10}$ fatty acid methyl ester | 70.0% |

Example F

| Microemulsion | |
| --- | --- |
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Suspension Concentrate | |
| --- | --- |
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

| Emulsion in Water | |
| --- | --- |
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

| Oil Dispersion | |
| --- | --- |
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except that "Compound 1" is replaced with "Compound 2", "Compound 3", "Compound 4", "Compound 5", "Compound 6", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24", "Compound 25", "Compound 26", "Compound 27", "Compound 28", "Compound 29", "Compound 30", "Compound 31", "Compound 32", "Compound 33", "Compound 34", "Compound 35", "Compound 36", "Compound 37", "Compound 38", "Compound 39", "Compound 40", "Compound 41", "Compound 42", "Compound 43", "Compound 44", "Compound 45", "Compound 46", "Compound 47", "Compound 48", "Compound 49", "Compound 50", "Compound 51", "Compound 52", "Compound 53", "Compound 54", "Compound 55", "Compound 56", "Compound 57", "Compound 58", "Compound 59", "Compound 60", "Compound 61", "Compound 62", "Compound 63", "Compound 64", "Compound 65", "Compound 66", "Compound 67", "Compound 68", "Compound 69", "Compound 70", "Compound 71" or "Compound 72".

Test results indicate that the compounds of the present invention are highly active preemergent and/or postemergent herbicides and/or plant growth regulators. The compounds of the Mention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. A "-" means the entry is not available; "tol." means "tolerance" and "res." means resistance.

| Trait | Description |
|---|---|
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Modified flower color |
| T11 | ALS Herbicide Tol. |
| T12 | Dicamba tol. |
| T13 | Anti-allergy |
| T14 | Salt tol. |
| T15 | Cold tol. |
| T16 | Imidazolinone herb. tol. |
| T17 | Modified alpha-amylase |
| T18 | Pollination control |
| T19 | 2,4-D tol. |
| T20 | Increased lysine |
| T21 | Drought tol. |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tol. |
| T31 | Modified oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Modified product |

| Exibit C | | | | |
|---|---|---|---|---|
| Crop | Event Name | Event Code | Trait(s) | Gene(s) |
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |

Exibit C

| Crop | Event Name | Event Code | Trait(s) | Gene(s) |
|---|---|---|---|---|
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |

Exhibit C

| Crop | Event Name | Event Code | Trait(s) | Gene(s) |
|---|---|---|---|---|
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR 162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |

Exibit C

| Crop | Event Name | Event Code | Trait(s) | Gene(s) |
|---|---|---|---|---|
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Although most typically, compounds of the invention are used to control undesired vegetation, contact of desired vegetation in the treated locus with compounds of the invention may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenic an, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6 (5H)-one), 4-(2,6-diethyl-4-methylphenyl)-5-hydroxy-2,6-dimethyl-3 (2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5 (2H, 4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl) benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloro acetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention cans also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Table A1 lists specific combinations of a Component (a) with Component (b) illustrative of the mixtures, compositions and methods of the present invention. Compound 1 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
|---|---|---|---|---|
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Cafenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cinosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |

TABLE A1-continued

| Component (a) (Compound #) | Component (b) | Typical Weight Ratio | More Typical Weight Ratio | Most Typical Weight Ratio |
|---|---|---|---|---|
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |
| 1 | Halauxifen-methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Hydantocidin | 1:1100-16:1 | 1:385-8:1 | 1:144-4:1 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |

TABLE A1-continued

| Component (a) (Compound #) | Component (b) | Typical Weight Ratio | More Typical Weight Ratio | Most Typical Weight Ratio |
|---|---|---|---|---|
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Tolpyralate | 1:31-37:1 | 1:10-13:1 | 1:3-3:1 |
| 1 | Topramzone | 1:6-168:1 | 1:2-56:1 | 1:1-11:1 |
| 1 | Tralkoxydim | 1:68-17:1 | 1:22-6:1 | 1:8-2:1 |
| 1 | Triafamone | 1:2-420:1 | 1:1-140:1 | 2:1-27:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifludimoxazin | 1:25-45:1 | 1:8-15:1 | 1:3-3:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 2 in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D. Tables A3 through A7 are constructed similarly.

| Table Number | Component (a) Column Entries |
|---|---|
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |
| A9 | Compound 9 |
| A10 | Compound 10 |
| A11 | Compound 11 |
| A12 | Compound 12 |
| A13 | Compound 13 |
| A14 | Compound 14 |
| A15 | Compound 15 |
| A16 | Compound 16 |
| A17 | Compound 17 |
| A18 | Compound 18 |
| A19 | Compound 19 |
| A20 | Compound 20 |
| A21 | Compound 21 |
| A22 | Compound 22 |
| A23 | Compound 23 |
| A24 | Compound 24 |
| A25 | Compound 25 |
| A26 | Compound 26 |
| A27 | Compound 27 |
| A28 | Compound 28 |
| A29 | Compound 29 |
| A30 | Compound 30 |
| A31 | Compound 31 |
| A32 | Compound 32 |
| A33 | Compound 33 |
| A34 | Compound 34 |
| A35 | Compound 35 |
| A36 | Compound 36 |
| A37 | Compound 37 |
| A38 | Compound 38 |
| A39 | Compound 39 |
| A40 | Compound 40 |
| A41 | Compound 41 |
| A31 | Compound 42 |
| A43 | Compound 43 |
| A44 | Compound 44 |
| A45 | Compound 45 |
| A46 | Compound 46 |
| A47 | Compound 47 |
| A48 | Compound 48 |
| A49 | Compound 49 |
| A50 | Compound 50 |
| A51 | Compound 51 |
| A52 | Compound 52 |
| A53 | Compound 53 |
| A54 | Compound 54 |
| A55 | Compound 55 |
| A56 | Compound 56 |
| A57 | Compound 57 |
| A58 | Compound 58 |
| A59 | Compound 59 |
| A60 | Compound 60 |
| A61 | Compound 61 |
| A62 | Compound 62 |
| A63 | Compound 63 |
| A64 | Compound 64 |
| A65 | Compound 65 |
| A66 | Compound 66 |
| A67 | Compound 67 |
| A68 | Compound 68 |
| A69 | Compound 69 |
| A70 | Compound 70 |
| A71 | Compound 71 |
| A72 | Compound 72 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this invention against specific weeds. The weed control afforded by the compounds is not limited, however, to these species. See Index Tables A for compound descriptions. The following abbreviations are used in the Index Table which follow: c-Pr is cyclopropyl, "Cmpd. No." stands for "Compound Number", "Ex." stands for "Example" and is followed by a number indicating in which example the compound is prepared. Unless otherwise indicated in the following Index Tables each of $X^1$, $X^2$, $X^3$, $X^4$, $X^5$, $X^6$, $X^7$, $X^8$, $X^9$ and $X^{10}$ is CH. $^1$H NMR spectra are reported in ppm downfield from tetramethylsilane in $CDCl_3$ solution unless indicated otherwise; "s" means singlet, "d" means doublet, "d" means doublet of doublets, "t" means triplet, "q" means quartet, "m" means multiplet, and "brs" means broad singlet. Mass spectra are reported with an estimated precision within ±0.5 Da as the molecular weight of the highest isotopic abundance parent ion (M+1) formed by addition of $H^+$ (molecular weight of 1) to the molecule observed by using atmospheric pressure chemical ionization (AP+).

TABLE A

INDEX

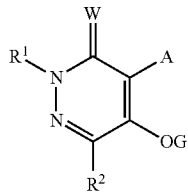

| Cmpd. No. | (R¹) | R² | W | A | G | m.p. (° C.) or AP+ |
|---|---|---|---|---|---|---|
| 1 | $CH_3$ | $CH_3$ | O | A-1 ($Y^1$ is S, $X^6$ is N) | H | 199-203 |
| 2 | $CH_3$ | $CH_3$ | O | A-4 ($Y^4$ is S, $X^1$ is $CCH_3$, $X^7$ is N, $X^9$ is $CCH_3$) | $C(O)OCH_2CH_3$ | 175-178 |
| 3 | $CH_3$ | $CH_3$ | O | A-4 ($Y^4$ is S, $X^1$ is $CCH_3$, $X^7$ is N, $X^9$ is $CCH_3$) | H | 257-259 |
| 4 | $CH_3$ | $CH_3$ | O | A-1 ($Y^1$ is S) | $C(O)CH_2CH_3$ | 130-134 |
| 5 | $CH_3$ | $CH_3$ | O | A-1 ($Y^1$ is S) | $C(O)OCH_2CH_3$ | 165-169 |
| 6 | $CH_3$ | $CH_3$ | O | A-4 ($Y^4$ is S, $X^1$ is $CCH_3$, $X^7$ is N, $X^9$ is $CCH_3$) | C(O)O-i-Pr | 145-148 |
| 7 | $CH_3$ | $CH_3$ | O | A-2 ($Y^2$ is O, $X^1$ is $CCH_3$) | H | 244-247 |
| 8 | $CH_3$ | $CH_3$ | O | A-3 ($X^2$ is N) | $C(O)CH_3$ | 310 (AP+) |
| 9 | $CH_3$ | $CH_3$ | O | A-4 ($Y^4$ is S, $X^1$ is $CCH_3$, $X^7$ is N, $X^9$ is $CCH_3$) | C(O)-c-Pr | 139-142 |
| 10 | $CH_3$ | $CH_3$ | O | A-2 ($Y^2$ is O, $X^1$ is $CCH_3$, $X^5$ is $CCH_3$) | H | 194-199 |
| 11 | CH | $CH_3$ | O | A-2 ($Y^2$ is O, $X^1$ is $CCH_3$, $X^5$ is $CCH_3$) | $C(O)CH_3$ | 93-96 |
| 12 (Ex. 1) | $CH_3$ | $CH_3$ | O | A-2 ($Y^2$ is O, $X^5$ is $CCH_3$) | H | 272-275 |
| 13 (Ex. 2) | $CH_3$ | $CH_3$ | O | A-2 ($Y^2$ is O, $X^5$ is $CCH_3$) | $C(O)CH_3$ | 144-147 |
| 14 | $CH_3$ | $CH_3$ | O | A-4 ($Y^4$ is S, $X^1$ is $CCH_3$, $X^7$ is N) | H | 246-250 |
| 15 | $CH_3$ | $CH_3$ | O | A-4 ($Y^4$ is S, $X^1$ is $CCH_3$, $X^7$ is N) | C(O)O-i-Pr | 93-97 |
| 16 | $CH_3$ | $CH_3$ | O | A-3 ($X^2$ is N, $X^3$ is $COCH_3$) | H | 298 (AP+) |
| 17 | $CH_3$ | $CH_3$ | O | A-2 ($Y^2$ is O, $X^1$ is $CCH_3$, $X^5$ is $CCH_3$) | $C(O)OCH_3$ | 131-134 |
| 18 | $CH_3$ | $CH_3$ | O | A-4 ($Y^4$ is S, $X^1$ is $CCH_2CH_3$, $X^7$ is N) | H | 212-215 |
| 19 | $CH_3$ | $CH_3$ | O | A-4 ($Y^4$ is S, $X^1$ is $CCH_2CH_3$, $X^7$ is N) | $C(O)OCH_2CH_3$ | 143-146 |
| 20 | $CH_3$ | $CH_3$ | O | A-4 ($Y^4$ is S, $X^1$ is $CCH_2CH_3$, $X^7$ is N) | C(O)O-i-Pr | 158-161 |
| 21 | $CH_3$ | $CH_3$ | O | A-4 ($Y^4$ is S, $X^1$ is $CCH_2CH_3$, $X^7$ is N) | C(O)-c-Pr | 138-141 |
| 22 | $CH_3$ | $CH_3$ | O | A-2 ($Y^2$ is O, $X^1$ is $CCH_3$, $X^5$ is $CCH_3$) | $C(O)CH_2CH_3$ | 117-121 |
| 23 | $CH_3$ | $CH_3$ | O | A-4 ($Y^4$ is S, $X^1$ is $CCH_3$, $X^7$ is N) | C(O)-c-Pr | 106-110 |
| 24 | $CH_3$ | $CH_3$ | O | A-4 ($Y^4$ is S, $X^1$ is $CCH_3$, $X^7$ is N) | $C(O)OCH_2CH_3$ | |
| 25 | $CH_3$ | $CH_3$ | O | A-1 ($Y^1$ is S, $X^5$ is N, $X^6$ is $CCH_3$) | H | 115-118 |
| 26 | $CH_3$ | $CH_3$ | O | A-2 ($Y^2$ is O, $X^5$ is $CCH_3$) | $C(O)CH_2CH_3$ | 147-150 |
| 27 | $CH_3$ | $CH_3$ | O | A-1 ($Y^1$ is S, $X^5$ is $CCH_3$, $X^6$ is N) | H | 219-222 |
| 28 | $CH_3$ | $CH_3$ | O | A-2 ($Y^2$ is O, $X^5$ is $CCH_3$) | $C(O)OCH_3$ | |
| 29 (Ex. 3) | $CH_3$ | $CH_3$ | O | A-1 ($Y^1$ is S, $X^1$ is $CCH_3$) | H | 204-207 |
| 30 | $CH_3$ | $CH_3$ | O | A-1 ($Y^1$ is S, $X^1$ is $CCH_3$) | $C(O)OCH_2CH_3$ | 103-107 |
| 31 | $CH_3$ | $CH_3$ | O | A-1 ($Y^1$ is S, $X^1$ is $CCH_3$) | $C(O)CH_2CH_3$ | 122-125 |
| 32 | $CH_3$ | $CH_3$ | O | A-1 ($Y^1$ is S) | H | 267-272 |
| 33 | $CH_3$ | $CH_3$ | O | A-2 ($Y^2$ is O, $X^3$ is CF) | $C(O)CH_3$ | * |
| 34 | $CH_3$ | H | O | A-3 ($X^8$ is N) | H | * |
| 35 | $CH_3$ | $CH_3$ | O | A-2 ($Y^2$ is S, $X^3$ is CCl) | C(O)Ph | 148-152 |
| 36 | $CH_3$ | $CH_3$ | O | A-2 ($Y^2$ is S, $X^3$ is CCl) | $C(O)CH_2CH_3$ | 128-132 |
| 37 | $CH_3$ | $CH_3$ | O | A-1 ($Y^1$ is S, $X^3$ is CCl, $X^5$ is CBr) | H | 240-244 |
| 38 | $CH_3$ | Cl | O | A-1 ($Y^1$ is NH, $X^5$ is N, $X^6$ is N) | H | 278 |
| 39 | $CH_3$ | $CH_3$ | O | A-2 ($Y^2$ is O, $X^3$ is CCl, $X^5$ is $CCH_3$) | C(O)Ph | 122-126 |
| 40 | $CH_3$ | $CH_3$ | O | A-2 ($Y^2$ is O, $X^3$ is CCl, $X^5$ is $CCH_3$) | $C(O)OCH_3$ | 155-159 |
| 41 | $CH_3$ | $CH_3$ | O | A-2 ($Y^2$ is O, $X^3$ is CCl, $X^5$ is $CCH_3$) | $C(O)CH_2CH_3$ | 361 * |
| 42 | $CH_3$ | $CH_3$ | O | A-2 ($Y^2$ is O, $X^3$ is CCl, $X^5$ is $CCH_3$) | $C(O)CH_3$ | 133-137 |
| 43 | $CH_3$ | $CH_3$ | O | A-2 ($Y^2$ is O, $X^3$ is CCl, $X^5$ is $CCH_3$) | H | 302-306 |
| 44 | $CH_3$ | $CH_3$ | O | A-1 ($Y^1$ is O, $X^3$ is CCl, $X^5$ is $CCH_3$) | C(O)Ph | 141-145 |
| 45 | $CH_3$ | $CH_3$ | O | A-1 ($Y^1$ is O, $X^3$ is CCl, $X^5$ is $CCH_3$) | H | 249-253 |
| 46 | $CH_3$ | $CH_3$ | O | A-1 ($Y^1$ is S, $X^1$ is $CCH_3$, $X^5$ is CCl) | H | 240-243 |
| 47 | $CH_3$ | $CH_3$ | O | A-2 ($Y^2$ is O, $X^1$ is $CCF_3$, $X^5$ is $CCH_3$) | $C(O)CH_2CH_3$ | 99-103 |
| 48 | $CH_3$ | $CH_3$ | O | A-2 ($Y^2$ is O, $X^1$ is $CCF_3$, $X^5$ is $CCH_3$) | $C(O)CH_3$ | 142-146 |
| 49 | $CH_3$ | $CH_3$ | O | A-2 ($Y^2$ is O, $X^1$ is $CCF_3$, $X^5$ is $CCH_3$) | H | 244-248 |
| 50 | $CH_3$ | $CH_3$ | O | A-2 ($Y^2$ is S, $X^3$ is CCl) | $C(O)OCH_3$ | 159-163 |
| 51 | $CH_3$ | $CH_3$ | O | A-2 ($Y^2$ is S, $X^3$ is CCl) | $C(O)CH_3$ | 165-169 |
| 52 | $CH_3$ | $CH_3$ | O | A-1 ($Y^1$ is O, $X^3$ is CCl, $X^5$ is $CCH_3$) | $C(O)CH_2CH_3$ | 120-124 |
| 53 | $CH_3$ | $CH_3$ | O | A-1 ($Y^1$ is O, $X^3$ is CCl, $X^5$ is $CCH_3$) | $C(O)OCH_3$ | 123-127 |
| 54 | $CH_3$ | $CH_3$ | O | A-1 ($Y^1$ is O, $X^3$ is CCl, $X^5$ is $CCH_3$) | $C(O)CH_3$ | 163-167 |
| 55 | $CH_3$ | $CH_3$ | O | A-2 ($Y^2$ is O, $X^3$ is CCl) | H | 268-272 |
| 56 | $CH_3$ | $CH_3$ | O | A-2 ($Y^2$ is O, $X^3$ is CCl) | H | * |
| 57 | $CH_3$ | $CH_3$ | O | A-1 ($Y^1$ is S, $X^3$ is CCl) | C(O)Ph | 166-170 |
| 58 | $CH_3$ | $CH_3$ | O | A-1 ($Y^1$ is S, $X^3$ is CCl) | $C(O)CH_2CH_3$ | 143-147 |
| 59 | $CH_3$ | $CH_3$ | O | A-1 ($Y^1$ is S, $X^3$ is CCl) | $C(O)OCH_3$ | 176-180 |
| 60 | $CH_3$ | $CH_3$ | O | A-1 ($Y^1$ is S, $X^3$ is CCl) | $C(O)CH_3$ | 169-173 |

TABLE A-continued

INDEX

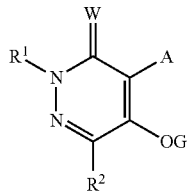

1

| Cmpd. No. | (R¹) | R² | W | A | G | m.p. (° C.) or AP+ |
|---|---|---|---|---|---|---|
| 61 | $CH_3$ | Cl | O | A-1 ($Y^1$ is $NCH_3$, $X^5$ is N, $X^6$ is N) | H | 290 (AP−) |
| 62 | $CH_3$ | Cl | O | A-2 ($Y^2$ is $NCH_3$, $X^4$ is N, $X^5$ is N) | H | 282 |
| 63 | $CH_3$ | $CH_3$ | O | A-1 ($Y^1$ is S, $X^3$ is CCl) | H | 268-272 |
| 64 | $CH_3$ | $CH_3$ | O | A-1 ($Y^1$ is $NCH_3$, $X^1$ is CBr, $X^5$ is N) | $C(O)CH_2CH_3$ | 142-146 |
| 65 | $CH_3$ | $CH_3$ | O | A-1 ($Y^1$ is $NCH_3$, $X^1$ is CBr, $X^5$ is N) | H | 316-320 |
| 66 | $CH_3$ | Cl | O | A-3 ($X^1$ is N) | $C(O)CH_3$ | 330 |
| 67 (Ex. 4) | $CH_3$ | Cl | O | A-3 ($X^1$ is N) | H | 288 |
| 68 (Ex. 6) | $CH_3$ | $CH_3$ | O | A-2 ($Y^2$ is O, $X^3$ is CF) | H | 275 |
| 69 (Ex. 5) | $CH_3$ | $CH_3$ | O | A-2 ($Y^2$ is O, $X^3$ is CF) | $CH_3$ | 289 |
| 70 | $CH_3$ | Cl | O | A-2 ($Y^2$ is O, $X^3$ is CF) | H | * |
| 71 | $CH_3$ | Cl | O | A-3 ($X^{10}$ is N) | $C(O)CH_3$ | * |
| 72 | $CH_3$ | $CH_3$ | O | A-1 ($Y^1$ is S, $X^1$ is $CCH_3$, $X^5$ is $CCH_3$) | H | 227-230 |

\* See Index Table B for ¹H NMR data.
\*\* See Synthesis Example for ¹H NMR data.

INDEX TABLE B

| Cmpd. No. | ¹H NMR Data (CDCl₃ solution at 500 MHz unless indicated otherwise)ᵃ |
|---|---|
| 33 | δ 7.60 (m, 1H), 7.27-7.31 (m, 1H), 6.99-7.02 (m, 1H), 6.90 (m, 1H), 3.83 (s, 3H), 2.28 (s, 3H), 1.94 (s, 3H). |
| 34 | δ (dmso-d₆, 500 MHz) 11.17 (brs, 1H), 9.41 (brs, 1H), 8.50 (brs, 1H), 8.16 (d, 1H), 7.88 (s, 1H), 7.74 (dd, 1H), 7.66 (d, 1H), 7.43 (brs, 1H), 3.66 (s, 3H). |
| 41 | δ 7.23-7.21 (d, 1H, J = 8.4 Hz), 7.14-7.12 (d, 1H, J = 8.4 Hz), 6.49 (s, 1H), 3.82 (s, 1H), 2.43 (s, 3H), 2.26 (s, 3H), 2.23-2.18 (q, 2H), 0.94-0.91 (t, 3H). |
| 56 | δ 7.69 (m, 1H), 7.36-7.44 (m, 3H), 6.96 (m, 1H), 3.78 (s, 3H), 2.36 (s, 3H). |
| 70 | δ (DMSO-d₆) 8.02 (m, 1H), 7.28-7.31 (m, 1H), 7.15-7.19 (m, 1H), 7.11-7.12 (d, J = 2.7 Hz, 1H), 3.62 (s, 3H). |
| 71 | δ (500 MHz) 8.88 (dd, 1H), 8.19 (dd, 1H), 7.92 (m, 1H), 7.59 (m, 2H), 7.43 (dd, 1H), 3.84 (s, 3H), 1.95 (s, 3H). |

Biological Examples of the Invention

Test A

Seeds of plant species selected from barnyardgrass (*Echinochloa crus-galli*), kochia (*Kochia scoparia*), ragweed (common ragweed, *Ambrosia elatior*), ryegrass, It. (Italian ryegrass, *Lolium multiflorum*), foxtail, giant (giant foxtail, *Setaria faberii*), and pigweed (*Amaranthus retroflexus*), were planted into a blend of loam soil and sand and treated preemergence with a directed soil spray using test chemicals formulated in a non-phytotoxic solvent mixture which included a surfactant.

At the same time, plants selected from these weed species and also wheat (*Triticum aestivum*), corn (*Zea mays*), blackgrass (*Alopecurus myosuroides*), and galium (catchweed bedstraw, *Galium aparine*), were planted in pots containing the same blend of loam soil and sand and treated with postemergence applications of test chemicals formulated in the same manner Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 1000 g ai/ha Postemergence | Compound 35 |
|---|---|
| Barnyardgrass | 20 |
| Blackgrass | 30 |
| Corn | 0 |
| Galium | 100 |
| Foxtail, Green | 0 |
| Kochia | 0 |

| 1000 g ai/ha Postemergence | Compound 35 |
|---|---|

TABLE A-continued

|  | | |
|---|---|---|
| Foxtail, Green | | 0 |
| Kochia | | 0 |
| Pigweed | | 0 |
| Ragweed | | 0 |
| Ryegrass, It. | | 70 |
| Wheat | | 0 |

| 500 g ai/ha | Compounds | | | | | | | | | | | | | |
|---|---|---|---|---|---|---|---|---|---|---|---|---|---|---|
| Postemergence | 1 | 2 | 3 | 4 | 5 | 6 | 7 | 8 | 9 | 10 | 11 | 12 | 13 | 14 |
| Barnyardgrass | 0 | 20 | 30 | 20 | 20 | 10 | 80 | 20 | 20 | 90 | 60 | 30 | 50 | 0 |
| Blackgrass | 10 | 40 | 40 | 30 | 60 | 20 | 90 | 0 | 20 | 90 | 90 | 80 | 80 | 0 |
| Corn | 0 | 0 | 0 | 0 | 0 | 0 | 60 | 0 | 0 | 30 | 30 | 10 | 20 | 0 |
| Foxtail, Giant | 0 | 20 | 30 | 20 | 20 | 40 | 90 | 20 | 40 | 90 | 80 | 40 | 50 | 0 |
| Galium | 30 | 80 | 80 | 90 | 80 | 70 | 100 | 80 | 60 | 100 | 90 | 90 | 90 | 40 |
| Kochia | 0 | 90 | 90 | 20 | 20 | 60 | 100 | 80 | 50 | 100 | 100 | 50 | 80 | 0 |
| Pigweed | 10 | 90 | 90 | 30 | 20 | 80 | 90 | 80 | 80 | 100 | 100 | 50 | 70 | 0 |
| Ragweed | 10 | 50 | 50 | 40 | 20 | 30 | 90 | 0 | 30 | 100 | 100 | 80 | 70 | 0 |
| Ryegrass, It. | 40 | 90 | 80 | 100 | 90 | 60 | 100 | 30 | 60 | 100 | 100 | 100 | 100 | 20 |
| Wheat | 0 | 20 | 20 | 0 | 20 | 0 | 70 | 0 | 0 | 60 | 40 | 20 | 20 | 0 |

| 500 g ai/ha | Compounds | | | | | | | | | | | | | |
|---|---|---|---|---|---|---|---|---|---|---|---|---|---|---|
| Postemergence | 15 | 16 | 18 | 19 | 20 | 21 | 23 | 24 | 25 | 27 | 29 | 30 | 31 | 32 | 52 |
| Barnyardgrass | 0 | 10 | 0 | 0 | 0 | 0 | 0 | 0 | 40 | 20 | 70 | 80 | 60 | 50 | 10 |
| Blackgrass | 0 | 20 | 0 | 0 | 0 | 0 | 0 | 0 | 30 | 30 | 80 | 90 | 60 | 30 | 10 |
| Corn | 0 | 0 | 0 | 0 | 0 | 0 | 20 | 10 | 20 | 0 | 50 | 40 | 40 | 0 | 0 |
| Foxtail, Giant | 0 | 0 | 0 | 0 | 0 | 0 | 0 | 0 | 80 | 40 | 80 | 70 | 80 | 40 | 0 |
| Galium | 0 | 100 | 20 | 20 | 40 | 20 | 0 | 0 | 90 | 60 | 100 | 100 | 100 | 80 | 90 |
| Kochia | 0 | 100 | 0 | 0 | 0 | 0 | 0 | 0 | 100 | 0 | 100 | 100 | 100 | 70 | 20 |
| Pigweed | 0 | 70 | 30 | 30 | 50 | 30 | 40 | 10 | 90 | 0 | 100 | 90 | 90 | 30 | 60 |
| Ragweed | 0 | 70 | 0 | 0 | 0 | 0 | 0 | 0 | 90 | 30 | 80 | 90 | 80 | 40 | 60 |
| Ryegrass, It. | 0 | 100 | 0 | 0 | 0 | 0 | 10 | 20 | 70 | 40 | 90 | 100 | 100 | 90 | 60 |
| Wheat | 0 | 0 | 0 | 0 | 0 | 0 | 0 | 0 | 30 | 0 | 30 | 30 | 30 | 20 | 0 |

| 125 g ai/ha | Compounds | | | | | | | | | | | | | |
|---|---|---|---|---|---|---|---|---|---|---|---|---|---|---|
| Postemergence | 1 | 2 | 3 | 4 | 5 | 6 | 7 | 8 | 9 | 10 | 11 | 12 | 13 | 14 |
| Barnyardgrass | 0 | 0 | 0 | 0 | 0 | 0 | 30 | 0 | 0 | 50 | 30 | 10 | 0 | 0 |
| Blackgrass | 0 | 20 | 20 | 20 | 30 | 0 | 80 | 0 | 0 | 60 | 60 | 40 | 60 | 0 |
| Corn | 0 | 0 | 0 | 0 | 0 | 0 | 0 | 0 | 0 | 10 | 0 | 0 | 0 | 0 |
| Foxtail, Giant | 0 | 0 | 0 | 0 | 0 | 20 | 80 | 0 | 0 | 80 | 60 | 20 | 30 | 0 |
| Galium | 0 | 40 | 30 | 70 | 30 | 50 | 100 | 10 | 50 | 100 | 90 | 80 | 80 | 0 |
| Kochia | 0 | 30 | 30 | 0 | 0 | 30 | 100 | 30 | 40 | 100 | 100 | 0 | 50 | 0 |
| Pigweed | 0 | 70 | 80 | 20 | 0 | 20 | 90 | 70 | 50 | 90 | 90 | 30 | 60 | 0 |
| Ragweed | 0 | 20 | 20 | 0 | 0 | 10 | 90 | 0 | 10 | 100 | 100 | 40 | 50 | 0 |
| Ryegrass, It. | 0 | 30 | 20 | 80 | 70 | 20 | 100 | 0 | 30 | 100 | 100 | 90 | 90 | 0 |
| Wheat | 0 | 0 | 0 | 0 | 0 | 0 | 20 | 0 | 0 | 20 | 0 | 0 | 0 | 0 |

| 125 g ai/ha | Compounds | | | | | | | | | | | | | |
|---|---|---|---|---|---|---|---|---|---|---|---|---|---|---|
| Postemergence | 15 | 16 | 17 | 18 | 19 | 20 | 21 | 22 | 23 | 24 | 25 | 26 | 27 | 28 |
| Barnyardgrass | 0 | 0 | 20 | 0 | 0 | 0 | 0 | 10 | 0 | 0 | 20 | 10 | 0 | 10 |
| Blackgrass | 0 | 0 | 40 | 0 | 0 | 0 | 0 | 80 | 0 | 0 | 20 | 20 | 0 | 30 |
| Corn | 0 | 0 | 0 | 0 | 0 | 0 | 0 | 0 | 0 | 0 | 0 | 0 | 0 | 0 |
| Foxtail, Giant | 0 | 0 | 50 | 0 | 0 | 0 | 0 | 70 | 0 | 0 | 30 | 30 | 20 | 20 |
| Galium | 0 | 70 | 100 | 0 | 0 | 10 | 10 | 90 | 0 | 0 | 80 | 90 | 0 | 80 |
| Kochia | 0 | 70 | 90 | 0 | 0 | 0 | 0 | 90 | 0 | 0 | 100 | 20 | 0 | 40 |
| Pigweed | 0 | 40 | 100 | 0 | 10 | 20 | 10 | 90 | 0 | 0 | 90 | 40 | 0 | 40 |
| Ragweed | 0 | 30 | 80 | 0 | 0 | 0 | 0 | 90 | 0 | 0 | 70 | 30 | 0 | 60 |
| Ryegrass, It. | 0 | 90 | 100 | 0 | 0 | 0 | 0 | 80 | 0 | 0 | 20 | 80 | 20 | 60 |
| Wheat | 0 | 0 | 0 | 0 | 0 | 0 | 0 | 0 | 0 | 0 | 20 | 0 | 0 | 0 |

| 125 g ai/ha | Compounds | | | | | | | | | | | | | |
|---|---|---|---|---|---|---|---|---|---|---|---|---|---|---|
| Postemergence | 29 | 30 | 31 | 32 | 33 | 34 | 36 | 37 | 38 | 39 | 40 | 41 | 42 | 43 |
| Barnyardgrass | 20 | 10 | 10 | 0 | 30 | 0 | 10 | 0 | 0 | 10 | 20 | 50 | 40 | 10 |
| Blackgrass | 70 | 40 | 50 | 0 | 20 | 0 | 0 | 0 | 0 | 20 | 20 | 50 | 50 | 50 |
| Corn | 20 | 20 | 20 | 0 | 20 | 0 | 0 | 0 | 0 | 0 | 10 | 20 | 10 | 0 |
| Foxtail, Giant | 20 | 10 | 10 | 0 | 30 | — | 0 | 0 | 0 | 10 | 20 | 60 | 30 | 0 |
| Foxtail, Green | — | — | — | — | — | 0 | — | — | — | — | — | — | — | — |
| Galium | 90 | 90 | 90 | 40 | 90 | 0 | 100 | 40 | 0 | 90 | 100 | 100 | 90 | 80 |
| Kochia | 90 | 90 | 90 | 20 | 100 | 0 | 30 | 10 | 0 | 0 | 0 | 0 | 0 | 0 |
| Pigweed | 90 | 90 | 90 | 30 | 80 | 0 | 30 | 0 | 0 | 0 | 40 | 70 | 50 | 0 |
| Ragweed | 80 | 60 | 70 | 0 | 60 | 0 | 0 | 0 | 0 | 10 | 40 | 80 | 10 | 20 |

TABLE A-continued

| | | | | | | | | | | | | | | |
|---|---|---|---|---|---|---|---|---|---|---|---|---|---|---|
| Ryegrass, It. | 100 | 100 | 100 | 70 | 100 | 0 | 80 | 0 | 0 | 30 | 70 | 100 | 90 | 80 |
| Wheat | 20 | 0 | 20 | 0 | 20 | 0 | 0 | 0 | 0 | 0 | 0 | 0 | 0 | 10 |

| 125 g ai/ha | Compounds | | | | | | | | | | | | | |
|---|---|---|---|---|---|---|---|---|---|---|---|---|---|---|
| Postemergence | 44 | 45 | 46 | 47 | 48 | 49 | 50 | 51 | 52 | 53 | 54 | 55 | 56 | 57 |
| Barnyardgrass | 0 | 0 | 30 | 10 | 10 | 10 | 10 | 10 | 0 | 10 | 0 | 10 | 10 | 0 |
| Blackgrass | 0 | 0 | 70 | 0 | 0 | 0 | 10 | 10 | 0 | 0 | 0 | 10 | 0 | 0 |
| Corn | 0 | 0 | 20 | 0 | 20 | 20 | 0 | 0 | 0 | 0 | 0 | 0 | 0 | 0 |
| Foxtail, Giant | 0 | 0 | 90 | — | — | — | 0 | 0 | 0 | 0 | 0 | 0 | — | 0 |
| Foxtail, Green | — | — | — | 10 | 10 | 30 | — | — | — | — | — | — | 10 | — |
| Galium | 0 | 70 | 90 | 80 | 80 | 90 | 100 | 100 | 90 | 80 | 70 | 100 | 100 | 0 |
| Kochia | 0 | 0 | 90 | 70 | 70 | 80 | 90 | 90 | 0 | 0 | 10 | 100 | 0 | 0 |
| Pigweed | 0 | 10 | 90 | 90 | 100 | 100 | 70 | 60 | 60 | 50 | 40 | 60 | 0 | 0 |
| Ragweed | 0 | 0 | 100 | 80 | 90 | 90 | 70 | 50 | 20 | 30 | 0 | 30 | 0 | 0 |
| Ryegrass, It. | 0 | 60 | 100 | 30 | 30 | 40 | 90 | 100 | 40 | 30 | 60 | 70 | 50 | 0 |
| Wheat | 0 | 0 | 20 | 0 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| Postemergence | 58 | 59 | 60 | 61 | 62 | 63 | 64 | 65 | 66 | 67 | 68 | 69 | 70 | 71 | 72 |
| Barnyardgrass | 0 | 0 | 0 | 0 | 0 | 0 | 0 | 0 | 10 | 0 | 10 | 0 | 90 | 40 | 40 |
| Blackgrass | 0 | 0 | 0 | 0 | 0 | 0 | 0 | 0 | 0 | 60 | 0 | 30 | 70 | 80 |
| Corn | 0 | 20 | 0 | 0 | 0 | 0 | 0 | 0 | 0 | 0 | 0 | 0 | 0 | 0 | 0 |
| Foxtail, Giant | 0 | 0 | 0 | — | — | 0 | — | — | 10 | 0 | 20 | 0 | 40 | 30 | 60 |
| Foxtail, Green | — | — | — | 0 | 0 | — | 0 | 0 | — | — | — | — | — | — | — |
| Galium | 90 | 80 | 100 | 0 | 70 | 90 | 50 | 0 | 50 | 40 | 90 | 0 | 90 | 80 | 100 |
| Kochia | 60 | 60 | 70 | 0 | 0 | 60 | 0 | 0 | 40 | 40 | 90 | 0 | 90 | — | 90 |
| Pigweed | 20 | 30 | 30 | 0 | 0 | 50 | 0 | 0 | 50 | 50 | 20 | 0 | 70 | 50 | 90 |
| Ragweed | 0 | 0 | 0 | 0 | 0 | 0 | 0 | 0 | 30 | 10 | 10 | 0 | 90 | 70 | 90 |
| Ryegrass, It. | 10 | 10 | 10 | 0 | 0 | 10 | 0 | 0 | 40 | 60 | 90 | 0 | 100 | 90 | 100 |
| Wheat | 0 | 0 | 0 | 0 | 0 | 0 | 0 | 0 | 0 | 0 | 0 | 0 | 0 | 30 | 0 |

| 31 g ai/ha | Compounds | | | | | | | | | | | | |
|---|---|---|---|---|---|---|---|---|---|---|---|---|---|
| Postemergence | 17 | 22 | 26 | 28 | 33 | 34 | 36 | 37 | 38 | 39 | 40 | 41 | 42 | 43 |
| Barnyardgrass | 10 | 10 | 0 | 0 | 0 | 0 | 0 | 0 | 0 | 0 | 10 | 20 | 10 | 0 |
| Blackgrass | 10 | 30 | 0 | 0 | 0 | 0 | 0 | 0 | 0 | 0 | 0 | 20 | 20 | 0 |
| Corn | 0 | 0 | 0 | 0 | 0 | 0 | 0 | 0 | 0 | 0 | 0 | 0 | 0 | 0 |
| Foxtail, Giant | 20 | 30 | 0 | 0 | 0 | — | 0 | 0 | 0 | 0 | 10 | 20 | 10 | 0 |
| Foxtail, Green | — | — | — | — | — | 0 | — | — | — | — | — | — | — | — |
| Galium | 80 | 70 | 70 | 40 | 60 | 0 | 90 | 20 | 0 | 30 | 90 | 90 | 90 | 70 |
| Kochia | 70 | 70 | 20 | 0 | 60 | 0 | 20 | 0 | 0 | 0 | 0 | 0 | 0 | 0 |
| Pigweed | 60 | 60 | 30 | 10 | 40 | 0 | 0 | 0 | 0 | 0 | 20 | 40 | 30 | 0 |
| Ragweed | 70 | 70 | 0 | 20 | 0 | 0 | 0 | 0 | 0 | 0 | 20 | 80 | 20 | 0 |
| Ryegrass, It. | 50 | 70 | 50 | 30 | 40 | 0 | 30 | 0 | 0 | 20 | 40 | 90 | 70 | 50 |
| Wheat | 0 | 0 | 0 | 0 | 0 | 0 | 0 | 0 | 0 | 0 | 0 | 0 | 0 | 0 |

| 31 g ai/ha | Compounds | | | | | | | | | | | | |
|---|---|---|---|---|---|---|---|---|---|---|---|---|---|
| Postemergence | 44 | 45 | 46 | 47 | 48 | 49 | 50 | 51 | 53 | 54 | 55 | 56 | 57 | 58 |
| Barnyardgrass | 0 | 0 | 10 | 0 | 0 | 0 | 0 | 0 | 0 | 0 | 0 | 0 | 0 | 0 |
| Blackgrass | 0 | 0 | 40 | — | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Foxtail, Giant | 0 | 0 | 50 | — | — | — | 0 | 0 | 0 | 0 | 0 | — | 0 | 0 |
| Foxtail, Green | — | — | — | 0 | 0 | 20 | — | — | — | — | — | 0 | — | — |
| Galium | 0 | 20 | 90 | 70 | 80 | 80 | 100 | 100 | 60 | 50 | 80 | 60 | 0 | 20 |
| Kochia | 0 | 0 | 60 | 40 | 50 | 60 | 40 | 70 | 0 | 0 | 40 | 0 | 0 | 0 |
| Pigweed | 0 | 0 | 90 | 90 | 70 | 90 | 60 | 50 | 30 | 30 | 30 | 0 | 0 | 0 |
| Ragweed | 0 | 0 | 90 | 40 | 70 | 80 | 10 | 0 | 0 | 0 | 0 | 0 | 0 | 0 |
| Ryegrass, It. | 0 | 20 | 90 | 0 | 0 | 10 | 60 | 70 | 10 | 20 | 40 | 50 | 0 | 0 |
| Wheat | 0 | 0 | 0 | 0 | 0 | 0 | 0 | 0 | 0 | 0 | 0 | 0 | 0 | 0 |

| 31 g ai/ha | Compounds | | | | | | | | | | | | |
|---|---|---|---|---|---|---|---|---|---|---|---|---|---|
| Postemergence | 59 | 60 | 61 | 62 | 63 | 64 | 65 | 66 | 67 | 68 | 69 | 70 | 71 | 72 |
| Barnyardgrass | 0 | 0 | 0 | 0 | 0 | 0 | 0 | 0 | 0 | 0 | 0 | 10 | 10 | 30 |
| Blackgrass | 0 | 0 | 0 | 0 | 0 | 60 | 0 | 0 | 0 | 0 | 0 | 0 | 10 | 40 |
| Corn | 0 | 0 | 0 | 0 | 0 | 0 | 0 | 0 | 0 | 0 | 0 | 0 | 0 | 0 |
| Foxtail, Giant | 0 | 0 | — | — | 0 | — | — | 0 | 0 | 0 | 0 | 10 | 10 | 30 |
| Foxtail, Green | — | — | 0 | 0 | — | 0 | 0 | — | — | — | — | — | — | — |
| Galium | 20 | 20 | 0 | 100 | 30 | 30 | 0 | 0 | 20 | 60 | 0 | 50 | 60 | 90 |
| Kochia | 0 | 20 | 0 | 0 | 0 | 0 | 0 | 0 | 0 | 20 | 0 | 40 | — | 70 |
| Pigweed | 0 | 0 | 0 | 0 | 0 | 0 | 0 | 40 | 40 | 0 | 0 | 10 | 20 | 90 |
| Ragweed | 0 | 0 | 0 | 0 | 0 | 0 | 0 | 10 | 0 | 0 | 0 | 10 | 30 | 70 |

TABLE A-continued

| | | | | | | | | | | | | | | |
|---|---|---|---|---|---|---|---|---|---|---|---|---|---|---|
| Ryegrass, It. | 0 | 0 | 0 | 0 | 0 | 0 | 0 | 20 | 20 | 80 | 0 | 70 | 50 | 90 |
| Wheat | 0 | 0 | 0 | 0 | 0 | 0 | 0 | 0 | 0 | 0 | 0 | 0 | 0 | 0 |

| 1000 g ai/ha Preemergence | Compound 35 |
|---|---|
| Barnyardgrass | 20 |
| Foxtail, Green | 0 |
| Kochia | 0 |
| Pigweed | 0 |
| Ragweed | 10 |
| Ryegrass, It. | 80 |

| 500 g ai/ha Preemergence | Compound 52 |
|---|---|
| Barnyardgrass | 0 |
| Foxtail, Giant | 0 |
| Kochia | 0 |
| Pigweed | 100 |
| Ragweed | 0 |
| Ryegrass, It. | 70 |

| 500 g ai/ha | Compounds | | | | | | | | | | | | | |
|---|---|---|---|---|---|---|---|---|---|---|---|---|---|---|
| Preemergence | 1 | 2 | 3 | 4 | 5 | 6 | 7 | 8 | 9 | 10 | 11 | 12 | 13 | 14 |
| Barnyardgrass | 20 | 20 | 10 | 20 | 40 | 0 | 90 | 0 | 0 | 90 | 100 | 50 | 60 | 0 |
| Foxtail, Giant | 20 | 20 | 10 | 20 | 40 | 0 | 90 | 20 | 40 | 100 | 100 | 60 | 60 | 0 |
| Kochia | 0 | 60 | 20 | 60 | 30 | 50 | 90 | 0 | 30 | 100 | 100 | 100 | 100 | 0 |
| Pigweed | 0 | 80 | 80 | 70 | 100 | 70 | 100 | 70 | 30 | 100 | 100 | 100 | 100 | 0 |
| Ragweed | 20 | 20 | 40 | 20 | 20 | — | 90 | 0 | 30 | 90 | 100 | 80 | 80 | 0 |
| Ryegrass, It. | 70 | 100 | 70 | 100 | 100 | 50 | 100 | 30 | 70 | 100 | 100 | 100 | 100 | 20 |

| 500 g ai/ha | Compounds | | | | | | | | | | | | |
|---|---|---|---|---|---|---|---|---|---|---|---|---|---|
| Preemergence | 15 | 16 | 18 | 19 | 20 | 21 | 23 | 24 | 25 | 27 | 29 | 30 | 31 | 32 |
| Barnyardgrass | 0 | 0 | 0 | 0 | 0 | 0 | 0 | 0 | 40 | 0 | 90 | 90 | 90 | 40 |
| Foxtail, Giant | 0 | 0 | 0 | 0 | 0 | 0 | 0 | 0 | 80 | 50 | 90 | 80 | 90 | 50 |
| Kochia | 0 | 100 | 0 | 0 | 0 | 0 | 0 | 0 | 100 | 0 | 90 | 80 | 90 | 40 |
| Pigweed | 0 | 100 | 10 | 20 | 40 | 0 | 0 | 0 | 100 | 0 | 100 | 100 | 100 | 100 |
| Ragweed | 0 | 70 | 0 | 0 | 0 | 0 | 0 | 0 | 70 | 20 | 90 | 90 | 90 | 80 |
| Ryegrass, It. | 0 | 90 | 0 | 0 | 0 | 0 | 0 | 20 | 30 | 40 | 100 | 100 | 100 | 100 |

| 125 g ai/ha | Compounds | | | | | | | | | | | | | |
|---|---|---|---|---|---|---|---|---|---|---|---|---|---|---|
| Preemergence | 1 | 2 | 3 | 4 | 5 | 6 | 7 | 8 | 9 | 10 | 11 | 12 | 13 | 14 |
| Barnyardgrass | 0 | 0 | 0 | 0 | 0 | 0 | 10 | 0 | 0 | 80 | 50 | 0 | 20 | 0 |
| Foxtail, Giant | 0 | 0 | 0 | 0 | 0 | 20 | 20 | 0 | 0 | 80 | 50 | 10 | 10 | 0 |
| Kochia | 0 | 0 | 0 | 0 | 10 | 0 | 30 | 0 | 0 | 100 | 90 | 60 | 0 | 0 |
| Pigweed | 0 | 0 | 40 | 40 | 20 | 0 | 100 | 20 | 0 | 100 | 100 | 60 | 40 | 0 |
| Ragweed | 0 | 0 | 0 | 0 | 0 | 0 | 40 | 0 | — | 90 | 90 | 60 | 40 | 0 |
| Ryegrass, It. | 0 | 30 | 30 | 40 | 80 | 0 | 100 | 0 | 30 | 100 | 100 | 100 | 100 | 10 |

| 125 g ai/ha | Compounds | | | | | | | | | | | | | |
|---|---|---|---|---|---|---|---|---|---|---|---|---|---|---|
| Preemergence | 15 | 16 | 17 | 18 | 19 | 20 | 21 | 22 | 23 | 24 | 25 | 26 | 27 | 28 |
| Barnyardgrass | 0 | 0 | 0 | 0 | 0 | 0 | 0 | 10 | 0 | 0 | 0 | 0 | 0 | 0 |
| Foxtail, Giant | 0 | 0 | 10 | 0 | 0 | 0 | 0 | 50 | 0 | 0 | 30 | 0 | 0 | 0 |
| Kochia | 0 | 40 | 100 | 0 | 0 | 0 | 0 | 90 | 0 | 0 | 100 | 30 | 0 | 20 |
| Pigweed | 0 | 30 | 100 | 0 | 0 | 0 | 0 | 100 | 0 | 0 | 80 | 10 | 0 | 0 |
| Ragweed | 0 | 30 | 90 | 0 | 0 | 0 | 0 | 80 | 0 | 0 | 40 | 10 | 20 | 30 |
| Ryegrass, It. | 0 | 80 | 90 | 0 | 0 | 0 | 0 | 80 | 0 | 10 | 0 | 80 | 30 | 70 |

| 125 g ai/ha | Compounds | | | | | | | | | | | | | |
|---|---|---|---|---|---|---|---|---|---|---|---|---|---|---|
| Preemergence | 29 | 30 | 31 | 32 | 33 | 34 | 36 | 37 | 38 | 39 | 40 | 41 | 42 | 43 |
| Barnyardgrass | 10 | 0 | 10 | 20 | 30 | 0 | 0 | 0 | 0 | 0 | 20 | 70 | 60 | 30 |
| Foxtail, Giant | 10 | 0 | 10 | 10 | 30 | — | 0 | 0 | 0 | 0 | 20 | 80 | 50 | 40 |
| Foxtail, Green | — | — | — | — | — | 0 | — | — | — | — | — | — | — | — |
| Kochia | 20 | 10 | 20 | 30 | 40 | 0 | 0 | 0 | 0 | 0 | 0 | 0 | 0 | 0 |
| Pigweed | 40 | 90 | 90 | 40 | 70 | 0 | 90 | 0 | 0 | 0 | 60 | 90 | 40 | 0 |
| Ragweed | 30 | 20 | 20 | 0 | 30 | 0 | 0 | 50 | 0 | 0 | 50 | 70 | 40 | 30 |
| Ryegrass, It. | 90 | 90 | 90 | 70 | 100 | 0 | 90 | 0 | 0 | 50 | 90 | 100 | 90 | 80 |

TABLE A-continued

| 125 g ai/ha | Compounds | | | | | | | | | | | | | |
|---|---|---|---|---|---|---|---|---|---|---|---|---|---|---|
| Preemergence | 44 | 45 | 46 | 47 | 48 | 49 | 50 | 51 | 52 | 53 | 54 | 55 | 56 | 57 |
| Barnyardgrass | 0 | 0 | 50 | 30 | 20 | 0 | 10 | 20 | 0 | 30 | 0 | 0 | 0 | 0 |
| Foxtail, Giant | 0 | 0 | 80 | — | — | — | 10 | 0 | 0 | 0 | 0 | 0 | — | 0 |
| Foxtail, Green | — | — | — | 0 | 20 | 0 | — | — | — | — | — | — | 0 | — |
| Kochia | 0 | 0 | 80 | 50 | 20 | 40 | 20 | 20 | 0 | 0 | 0 | 20 | 0 | 0 |
| Pigweed | 0 | 50 | 100 | 100 | 100 | 100 | 100 | 60 | 70 | 40 | 20 | 60 | 40 | 0 |
| Ragweed | 0 | 10 | 80 | 80 | 90 | 90 | 20 | 0 | 0 | 0 | 10 | 0 | 0 | 0 |
| Ryegrass, It. | 20 | 30 | 100 | 80 | 20 | 50 | 80 | 100 | 50 | 60 | 50 | 100 | 70 | 10 |

| 125 g ai/ha | Compounds | | | | | | | | | | | | | |
|---|---|---|---|---|---|---|---|---|---|---|---|---|---|---|
| Preemergence | 58 | 59 | 60 | 61 | 62 | 63 | 64 | 65 | 66 | 67 | 68 | 69 | 70 | 71 | 72 |
| Barnyardgrass | 0 | 0 | 0 | 0 | 0 | 0 | 0 | 0 | 0 | 0 | 20 | 0 | 90 | 20 | 30 |
| Foxtail, Giant | 0 | 0 | 0 | — | — | 0 | — | — | 0 | 0 | 20 | 0 | 50 | 10 | 40 |
| Foxtail, Green | — | — | — | 0 | 0 | — | 0 | 0 | — | — | — | — | — | — | — |
| Kochia | 70 | 20 | 0 | 0 | 0 | 20 | 0 | 0 | 0 | 0 | 60 | 0 | 40 | 30 | 40 |
| Pigweed | 0 | 0 | 100 | 0 | 0 | 0 | 0 | 0 | 20 | 20 | 80 | 0 | 30 | 60 | 70 |
| Ragweed | 80 | 30 | 0 | 0 | 0 | 0 | 0 | 0 | 0 | 0 | 50 | 0 | 0 | 10 | 90 |
| Ryegrass, It. | 50 | 10 | 10 | 0 | 0 | 20 | 0 | 0 | 50 | 50 | 80 | 0 | 100 | 80 | 100 |

| 31 g ai/ha | Compounds | | | | | | | | | | | | | |
|---|---|---|---|---|---|---|---|---|---|---|---|---|---|---|
| Preemergence | 17 | 22 | 26 | 28 | 33 | 34 | 36 | 37 | 38 | 39 | 40 | 41 | 42 | 43 |
| Barnyardgrass | 0 | 0 | 0 | 0 | 0 | 0 | 0 | 0 | 0 | 0 | 0 | 0 | 10 | 10 |
| Foxtail, Giant | 0 | 0 | 0 | 0 | 0 | — | 0 | 0 | 0 | 0 | 0 | 20 | 10 | 10 |
| Foxtail, Green | — | — | — | — | — | 0 | — | — | — | — | — | — | — | — |
| Kochia | 40 | 30 | 0 | 0 | 0 | 0 | 0 | 0 | 0 | 0 | 0 | 0 | 0 | 0 |
| Pigweed | 30 | 100 | 0 | 0 | 0 | 0 | 0 | 0 | 0 | 0 | 0 | 0 | 0 | 0 |
| Ragweed | 30 | 20 | 0 | 0 | 0 | 0 | 0 | 0 | 0 | 0 | 0 | 0 | 30 | 30 |
| Ryegrass, It. | 40 | 30 | 10 | 20 | 50 | 0 | 20 | 0 | 0 | 10 | 80 | 90 | 60 | 60 |

| 31 g ai/ha | Compounds | | | | | | | | | | | | | |
|---|---|---|---|---|---|---|---|---|---|---|---|---|---|---|
| Preemergence | 44 | 45 | 46 | 47 | 48 | 49 | 50 | 51 | 53 | 54 | 55 | 56 | 57 | 58 |
| Barnyardgrass | 0 | 0 | 0 | 0 | 0 | 0 | 0 | 0 | 0 | 0 | 0 | 0 | 0 | 0 |
| Foxtail, Giant | 0 | 0 | 30 | — | — | — | 0 | 0 | 0 | 0 | 0 | — | 0 | 20 |
| Foxtail, Green | — | — | — | 0 | 0 | 0 | — | — | — | — | — | 0 | — | — |
| Kochia | 0 | 0 | 50 | 40 | 10 | 0 | 0 | 0 | 0 | 0 | 0 | 0 | 50 | 0 |
| Pigweed | 0 | 0 | 100 | 60 | 20 | 30 | 0 | 0 | 0 | 0 | 0 | 0 | 0 | 20 |
| Ragweed | 0 | 0 | 80 | 20 | 0 | 0 | 0 | 0 | 20 | 0 | 0 | 0 | 0 | 0 |
| Ryegrass, It. | 0 | 0 | 90 | 0 | 10 | 20 | 60 | 60 | 0 | 30 | 80 | 10 | 0 | 0 |

| 31 g ai/ha | Compounds | | | | | | | | | | | | | |
|---|---|---|---|---|---|---|---|---|---|---|---|---|---|---|
| Preemergence | 59 | 60 | 61 | 62 | 63 | 64 | 65 | 66 | 67 | 68 | 69 | 70 | 71 | 72 |
| Barnyardgrass | 0 | 0 | 0 | 0 | 0 | 0 | 0 | 0 | 0 | 0 | 0 | 40 | 0 | 0 |
| Foxtail, Giant | 0 | 0 | — | — | 0 | — | — | 0 | 0 | 0 | 0 | 10 | 0 | 0 |
| Foxtail, Green | — | — | 0 | 0 | — | 0 | 0 | — | — | — | — | — | — | — |
| Kochia | 10 | 0 | 0 | 0 | 10 | 0 | 0 | 0 | 0 | 30 | 0 | 0 | 0 | 0 |
| Pigweed | 0 | 0 | 0 | 0 | 0 | 0 | 0 | 10 | 10 | 0 | 0 | 10 | 0 | 70 |
| Ragweed | 50 | 0 | 0 | 0 | 0 | 0 | 0 | 0 | 0 | 30 | 0 | 0 | 0 | 70 |
| Ryegrass, It. | 10 | 0 | 0 | 0 | 0 | 0 | 0 | 0 | 10 | 20 | 0 | 70 | 20 | 90 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

TABLE B

| 250 g ai/ha | Compounds | | | | | | | | | | | | | |
|---|---|---|---|---|---|---|---|---|---|---|---|---|---|---|
| Flood | 1 | 7 | 8 | 10 | 11 | 12 | 15 | 16 | 17 | 18 | 19 | 20 | 21 | 22 |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 23 | 24 | 25 | 26 | 27 | 28 | 29 | 30 | 31 | 32 | 33 | 34 | 36 | 37 |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 40 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 50 | 30 | 0 | 80 | 0 |

| 250 g ai/ha | Compounds | | | | | | | | | | | | | |
|---|---|---|---|---|---|---|---|---|---|---|---|---|---|---|
| Flood | 38 | 39 | 40 | 41 | 42 | 43 | 44 | 45 | 46 | 47 | 48 | 49 | 50 | 51 |
| Barnyardgrass | 0 | 0 | 0 | 20 | 0 | 0 | 0 | 0 | 0 | 0 | 0 | 0 | 0 | 0 |
| Ducksalad | 0 | 50 | 0 | 20 | 80 | 40 | 0 | 30 | 0 | 0 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 75 | 60 | 35 | 0 | 50 | 70 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 52 | 53 | 54 | 55 | 56 | 57 | 58 | 59 | 60 | 61 | 62 | 63 | 64 | 65 |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 20 | 0 | 0 | 0 | 0 | 0 | 0 |
| Sedge, Umbrella | 0 | 0 | 70 | 0 | 0 | 0 | — | 0 | 0 | 0 | 0 | 0 | 0 | 0 |

| 250 g ai/ha | Compounds | | | | | | |
|---|---|---|---|---|---|---|---|
| Flood | 66 | 67 | 68 | 69 | 70 | 71 | 72 |
| Barnyardgrass | 0 | 0 | 0 | 0 | 0 | 0 | 0 |
| Ducksalad | 0 | 0 | 0 | 0 | 0 | 0 | 0 |
| Rice | 0 | 0 | 0 | 0 | 0 | 0 | 0 |
| Sedge, Umbrella | 0 | 75 | 0 | 0 | 0 | 0 | 0 |

What is claimed is:

1. A compound of Formula 1, stereoisomers, N-oxides, and salts thereof

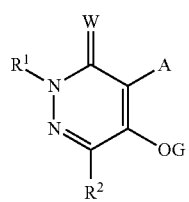

I wherein

R$^1$ is H, C$_1$-C$_7$ alkyl, C$_3$-C$_8$ alkylcarbonylalkyl, C$_3$-C$_8$ alkoxycarbonylalkyl, C$_4$-C$_7$ alkylcycloalkyl, C$_3$-C$_7$ alkenyl, C$_3$-C$_7$ alkynyl, C$_3$-C$_7$ cycloalkyl, C$_4$-C$_7$ cycloalkylalkyl, C$_2$-C$_3$ cyanoalkyl, C$_1$-C$_4$ nitroalkyl, C$_2$-C$_7$ haloalkoxyalkyl, C$_1$-C$_7$ haloalkyl, C$_3$-C$_7$ haloalkenyl, C$_2$-C$_7$ alkoxyalkyl, C$_3$-C$_7$ alkylthioalkyl, C$_1$-C$_7$ alkoxy, benzyl or phenyl; or a 5- or 6-membered saturated or partially saturated heterocyclic ring containing ring members selected from carbon and up to 1O and 1S;

W is O or S;

A is selected from

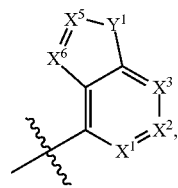

A-1

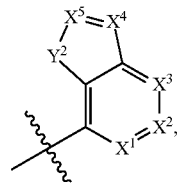

A-2

-continued

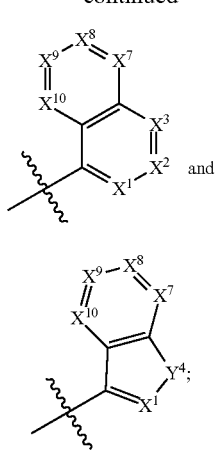

A-3 and

A-4

G is G¹ or W¹G¹;
W¹ is C₁-C₄ alkanediyl or C₂-C₄ alkenediyl;
G¹ is H, —C(=O)R⁷, —C(=S)R⁷, —CO₂R⁸, —C(=O)SR⁸, —S(O)₂R⁷, —CONR⁹R¹⁰, —S(O)₂NR⁹R¹⁰ or P(=O)R¹¹; or C₁-C₄ alkyl, C₂-C₄ alkenyl, C₂-C₄ alkynyl, C₁-C₄ haloalkyl, C₂-C₄ haloalkenyl, C₂-C₄ haloalkynyl, C₁-C₄ alkoxyalkyl, C₃-C₆ cycloalkyl or C₄-C₇ cycloalkylalkyl; or a 5- or 6-membered heterocyclic ring;
R² is H, halogen, —CN, —CHO, C₁-C₇ alkyl, C₃-C₈ alkylcarbonylalkyl, C₃-C₈ alkoxycarbonylalkyl, C₁-C₄ alkylcarbonyl, C₂-C₇ alkylcarbonyloxy, C₄-C₇ alkylcycloalkyl, C₃-C₇ alkenyl, C₃-C₇ alkynyl, C₁-C₄ alkylsulfinyl, C₁-C₄ alkylsulfonyl, C₁-C₄ alkylamino, C₂-C₈ dialkylamino, C₃-C₇ cycloalkyl, C₄-C₇ cycloalkylalkyl, C₂-C₃ cyanoalkyl, C₁-C₄ nitroalkyl, C₂-C₇ haloalkoxyalkyl, C₁-C₇ haloalkyl, C₃-C₇ haloalkenyl, C₂-C₇ alkoxyalkyl, C₁-C₇ alkoxy, C₁-C₅ alkylthio or C₂-C₃ alkoxycarbonyl; or phenyl optionally substituted by halogen, C₁-C₄ alkyl or C₁-C₄ haloalkyl;
each X¹ is independently N or CR³;
each X² is independently N or CR³;
each X³ is independently N or CR³;
each X⁴, X⁵ and X⁶ is independently N or CR⁴;
each X⁷, X⁸, X⁹ and X¹⁰ is independently N or CR⁵;
Y¹ is O, S or NR⁶;
Y² is O, S or NR⁶;
Y⁴ is O, S or NR⁶;
each R³ is independently H, halogen, nitro, —CN, C₁-C₅ alkyl, C₂-C₅ alkenyl, C₂-C₅ alkynyl, C₃-C₅ cycloalkyl, C₄-C₅ cycloalkylalkyl, C₁-C₅ haloalkyl, C₃-C₅ haloalkenyl, C₃-C₅ haloalkynyl, C₂-C₅ alkoxyalkyl, C₁-C₅ alkoxy, C₁-C₅ haloalkoxy, C₁-C₅ alkylthio, C₁-C₄ alkylsulfinyl, C₁-C₄ alkylsulfonyl, C₁-C₅ haloalkylthio or C₂-C₅ alkoxycarbonyl;
each R⁴ is independently H, halogen, nitro, —CN, C₁-C₅ alkyl, C₂-C₅ alkenyl, C₂-C₅ alkynyl, C₃-C₅ cycloalkyl, C₄-C₅ cycloalkylalkyl, C₁-C₅ haloalkyl, C₃-C₅ haloalkenyl, C₃-C₅ haloalkynyl, C₂-C₅ alkoxyalkyl, C₁-C₅ alkoxy, C₁-C₅ haloalkoxy, C₁-C₅ alkylthio, C₁-C₄ alkylsulfinyl, C₁-C₄ alkylsulfonyl, C₁-C₅ haloalkylthio or C₂-C₅ alkoxycarbonyl;
each R⁵ is independently H, halogen, nitro, —CN, C₁-C₅ alkyl, C₂-C₅ alkenyl, C₂-C₅ alkynyl, C₃-C₅ cycloalkyl, C₄-C₅ cycloalkylalkyl, C₁-C₅ haloalkyl, C₃-C₅ haloalkenyl, C₃-C₅ haloalkynyl, C₂-C₅ alkoxyalkyl, C₁-C₅ alkoxy, C₁-C₅ haloalkoxy, C₁-C₅ alkylthio, C₁-C₅ haloalkylthio or C₂-C₅ alkoxycarbonyl;
R⁶ is H, C₁-C₇ alkyl, C₂-C₇ alkenyl, C₂-C₇ alkynyl, C₃-C₇ cycloalkyl, C₄-C₇ cycloalkylalkyl, C₁-C₇ haloalkyl or C₂-C₇ alkoxyalkyl;
R⁷ is C₁-C₇ alkyl, C₃-C₇ alkenyl, C₃-C₇ alkynyl, C₃-C₇ cycloalkyl, C₁-C₇ haloalkyl, C₃-C₇ haloalkenyl, C₂-C₇ alkoxyalkyl or C₄-C₇ cycloalkylalkyl; or phenyl, benzyl, or a 5- to 6-membered heterocyclic ring, each phenyl, benzyl or heterocyclic ring optionally substituted by halogen, C₁-C₄ alkyl or C₁-C₄ haloalkyl;
R⁸ is C₁-C₇ alkyl, C₃-C₇ alkenyl, C₃-C₇ alkynyl, C₃-C₇ cycloalkyl, C₁-C₇ haloalkyl, C₃-C₇ haloalkenyl, C₂-C₇ alkoxyalkyl or C₄-C₇ cycloalkylalkyl; or phenyl, benzyl, or a 5- to 6-membered heterocyclic ring, each phenyl, benzyl or heterocyclic ring optionally substituted by halogen, C₁-C₄ alkyl or C₁-C₄ haloalkyl;
R⁹ is C₁-C₇ alkyl, C₃-C₇ alkenyl, C₃-C₇ alkynyl, C₃-C₇ cycloalkyl, C₂-C₇ haloalkyl, C₃-C₇ haloalkenyl, C₂-C₇ alkoxyalkyl or C₄-C₇ cycloalkylalkyl; or phenyl, benzyl or a 5- to 6-membered heterocyclic ring, each phenyl, benzyl or heterocycling ring optionally substituted by halogen, C₁-C₄ alkyl or C₁-C₄ haloalkyl;
R¹⁰ is H, C₁-C₇ alkyl, C₂-C₇ alkenyl, C₂-C₇ alkynyl, C₃-C₇ cycloalkyl, C₄-C₇ cycloalkylalkyl, C₁-C₇ haloalkyl or C₂-C₇ alkoxyalkyl; and
R¹¹ is C₁-C₇ alkyl or C₁-C₇ alkoxy;
provided
i) when A is A-3 and X² is CR³, then X³ is other than CR³;
ii) when A is A-3 and X³ is CR³, then X² is other than CR³;
iii) when A is A-4 and Y⁴ is O, S or NR⁶, then at least one of X⁷, X⁸, X⁹ and X¹⁰ is other than CR⁵; and
iv) when R¹ is CH₃; G is H or C(=O)CH₃; and R² is Cl or Br; then A-3 is other than 4-quinolinyl(5-Cl) and 4-isoquinolinyl.

2. The compound of claim 1 wherein
R¹ is H, C₁-C₇ alkyl, C₃-C₈ alkylcarbonylalkyl, C₃-C₈ alkoxycarbonylalkyl, C₄-C₇ alkylcycloalkyl, C₃-C₇ alkenyl, C₃-C₇ alkynyl, C₃-C₇ cycloalkyl, C₄-C₇ cycloalkylalkyl, C₂-C₃ cyanoalkyl, C₁-C₄ nitroalkyl, C₂-C₇ haloalkoxyalkyl, C₁-C₇ haloalkyl, C₃-C₇ haloalkenyl, C₂-C₇ alkoxyalkyl, C₃-C₇ alkylthioalkyl, C₁-C₇ alkoxy, benzyl or phenyl;
W is O;
A is A-1, A-2 or A-3;
G¹ is H, —C(=O)R⁷, —C(=S)R⁷, —CO₂R⁸, —C(=O)SR⁸, —CONR⁹R¹⁰ or P(=O)R¹¹; or C₁-C₄ alkyl, C₂-C₄ alkenyl, C₂-C₄ alkynyl, C₁-C₄ haloalkyl, C₂-C₄ haloalkenyl, C₂-C₄ haloalkynyl, C₁-C₄ alkoxyalkyl, C₃-C₆ cycloalkyl or C₄-C₇ cycloalkylalkyl;
W¹ is C₁-C₂ alkanediyl or C₂-C₃ alkenediyl;
R² is H, halogen, —CN, —CHO, C₁-C₇ alkyl, C₃-C₈ alkylcarbonylalkyl, C₃-C₈ alkoxycarbonylalkyl, C₁-C₄ alkylcarbonyl, C₂-C₇ alkylcarbonyloxy, C₄-C₇ alkylcycloalkyl, C₃-C₇ alkenyl, C₃-C₇ alkynyl, C₁-C₄ alkylsulfinyl, C₁-C₄ alkylsulfonyl, C₁-C₄ alkylamino, C₂-C₈ dialkylamino, C₃-C₇ cycloalkyl, C₄-C₇ cycloalkylalkyl, C₂-C₃ cyanoalkyl, C₁-C₄ nitroalkyl, C₂-C₇ haloalkoxyalkyl, C₁-C₇ haloalkyl, C₃-C₇ haloalkenyl, C₂-C₇ alkoxyalkyl, C₁-C₇ alkoxy or C₁-C₅ alkylthio;
each X¹ is independently CR³;
each R³ is independently H, halogen, C₁-C₃ alkyl, C₃-C₄ cycloalkyl, C₁-C₃ haloalkyl or C₁-C₃ alkoxy;
each R⁴ is independently H, halogen, C₁-C₃ alkyl, C₃-C₄ cycloalkyl, C₁-C₃ haloalkyl or C₁-C₃ alkoxy;

each R⁵ is independently H, halogen, $C_1$-$C_3$ alkyl, $C_3$-$C_4$ cycloalkyl, $C_1$-$C_3$ haloalkyl or $C_1$-$C_3$ alkoxy;

R⁶ is H or $C_1$-$C_3$ alkyl;

R⁷ is H, $C_1$-$C_7$ alkyl, $C_3$-$C_7$ cycloalkyl, $C_1$-$C_3$ haloalkyl or $C_2$-$C_7$ alkoxyalkyl;

R⁸ is H, $C_1$-$C_7$ alkyl, $C_3$-$C_7$ cycloalkyl, $C_1$-$C_3$ haloalkyl or $C_2$-$C_7$ alkoxyalkyl;

R⁹ is H, $C_1$-$C_7$ alkyl, $C_3$-$C_7$ cycloalkyl, $C_2$-$C_3$ haloalkyl or $C_2$-$C_7$ alkoxyalkyl;

R¹⁰ is H, $C_1$-$C_7$ alkyl, $C_3$-$C_7$ cycloalkyl, $C_1$-$C_3$ haloalkyl or $C_2$-$C_7$ alkoxyalkyl; and R¹¹ is $C_1$-$C_3$ alkyl or $C_1$-$C_3$ alkoxy.

3. The compound of claim 2 wherein

R¹ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl;

A is A-1 or A-2;

G¹ is H, —C(=O)R⁷, —CO₂R⁸, —CONR⁹R¹⁰ or P(=O)R¹¹; or $C_1$-$C_4$ alkyl, $C_2$-$C_4$ alkenyl, $C_1$-$C_4$ haloalkyl, $C_2$-$C_4$ haloalkenyl, $C_1$-$C_4$ alkoxyalkyl, $C_3$-$C_6$ cycloalkyl or $C_4$-$C_7$ cycloalkylalkyl;

W¹ is —CH₂— or —CH=CH—;

R² is H, halogen, —CN, —CHO, $C_1$-$C_7$ alkyl, $C_1$-$C_4$ alkylcarbonyl, $C_2$-$C_7$ alkylcarbonyloxy, $C_4$-$C_7$ alkylcycloalkyl, $C_1$-$C_4$ alkylsulfinyl, $C_1$-$C_4$ alkylsulfonyl, $C_1$-$C_4$ alkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl or $C_1$-$C_7$ alkoxy;

each X² is independently CR³;

each X⁵ is independently CR⁴;

Y¹ is O or S;

Y² is O or S;

each R³ is independently H, halogen, $C_1$-$C_2$ alkyl, cyclopropyl or $C_1$-$C_2$ haloalkyl;

each R⁴ is independently H, halogen, $C_1$-$C_2$ alkyl, cyclopropyl or $C_1$-$C_2$ haloalkyl;

R⁷ is H, $C_1$-$C_7$ alkyl, $C_3$-$C_7$ cycloalkyl or $C_2$-$C_7$ alkoxyalkyl;

R⁸ is H, $C_1$-$C_7$ alkyl, $C_3$-$C_7$ cycloalkyl or $C_2$-$C_7$ alkoxyalkyl;

R⁹ is H, $C_1$-$C_7$ alkyl, $C_3$-$C_7$ cycloalkyl or $C_2$-$C_7$ alkoxyalkyl;

R¹⁰ is H, $C_1$-$C_7$ alkyl, $C_3$-$C_7$ cycloalkyl or $C_2$-$C_7$ alkoxyalkyl; and R¹¹ is CH₃ or OCH₃.

4. The compound of claim 3 wherein

R¹ is $C_1$-$C_4$ alkyl, $C_3$-$C_4$ cycloalkyl, $C_2$-$C_3$ cyanoalkyl, $C_1$-$C_3$ haloalkyl or $C_2$-$C_4$ alkoxyalkyl;

A is selected from

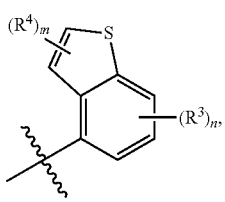

A-1-A

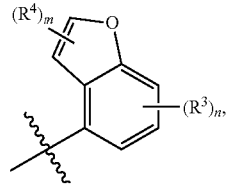

A-1-B

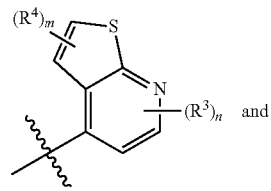

A-1-C

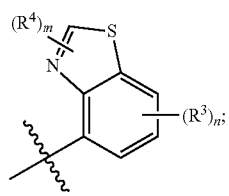

A-1-D

G¹ is H, —C(=O)R⁷, —CO₂R⁸ or P(=O)R¹¹; or $C_1$-$C_4$ alkyl, $C_1$-$C_4$ haloalkyl, $C_1$-$C_4$ alkoxyalkyl or $C_3$-$C_6$ cycloalkyl;

W¹ is —CH₂—;

R² is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy;

each R³ is independently H, halogen, methyl, ethyl or CF₃;

each R⁴ is independently H, halogen, methyl, ethyl or CF₃;

R⁷ is $C_1$-$C_7$ alkyl or $C_2$-$C_7$ alkoxyalkyl;

R⁸ is $C_1$-$C_7$ alkyl or $C_2$-$C_7$ alkoxyalkyl; and

R¹¹ is OCH₃.

5. The compound of claim 4 wherein

R¹ is methyl, ethyl, n-propyl or 2-methoxyethyl;

A is selected from A-1-A and A-1-B;

G is G¹;

G¹ is H, —C(=O)R⁷, —CO₂R⁸; or $C_1$-$C_4$ alkoxyalkyl or $C_3$-$C_6$ cycloalkyl;

R² is H, Cl, Br, I, —CN, methyl or methoxy;

each R³ is independently H, F, Cl, Br or methyl;

each R⁴ is independently H, methyl or ethyl;

R⁷ is $C_1$-$C_3$ alkyl or $C_2$-$C_4$ alkoxyalkyl; and

R⁸ is $C_1$-$C_3$ alkyl or $C_2$-$C_4$ alkoxyalkyl.

6. The compound of claim 3 wherein

R¹ is $C_1$-$C_4$ alkyl, $C_3$-$C_4$ cycloalkyl, $C_2$-$C_3$ cyanoalkyl, $C_1$-$C_3$ haloalkyl or $C_2$-$C_4$ alkoxyalkyl;

A is selected from

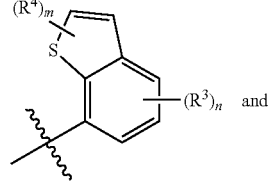

A-2-A

-continued

A-2-B

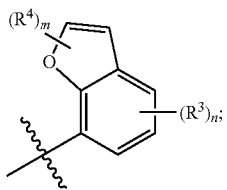

$G^1$ is H, —C(=O)$R^7$, —CO$_2R^8$ or P(=O)$R^{11}$; or $C_1$-$C_4$ alkyl, $C_1$-$C_4$ haloalkyl, $C_1$-$C_4$ alkoxyalkyl or $C_3$-$C_6$ cycloalkyl;
$W^1$ is —CH$_2$—;
$R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy;
each $R^3$ is independently H, halogen, methyl, ethyl or CF$_3$;
each $R^4$ is independently H, halogen, methyl, ethyl or CF$_3$;
$R^7$ is $C_1$-$C_7$ alkyl or $C_2$-$C_7$ alkoxyalkyl;
$R^8$ is $C_1$-$C_7$ alkyl or $C_2$-$C_7$ alkoxyalkyl; and
$R^{11}$ is OCH$_3$.

7. The compound of claim 6 wherein
$R^1$ is methyl, ethyl, n-propyl or 2-methoxyethyl;
A is A-2-A;
G is $G^1$;
$G^1$ is H, —C(=O)$R^7$, —CO$_2R^8$; or $C_1$-$C_4$ alkoxyalkyl or $C_3$-$C_6$ cycloalkyl;
$R^2$ is H, Cl, Br, I, —CN, methyl or methoxy;
each $R^3$ is independently H, F, Cl, Br or methyl;
each $R^4$ is independently H, methyl or ethyl;
$R^7$ is $C_1$-$C_3$ alkyl or $C_2$-$C_4$ alkoxyalkyl; and
$R^8$ is $C_1$-$C_3$ alkyl or $C_2$-$C_4$ alkoxyalkyl.

8. The compound of claim 6 selected from the group consisting of
4-(2,6-dimethyl-7-benzofuranyl)-5-hydroxy-2,6-dimethyl-3(2H)-pyridazinone;
5-(acetyloxy)-4-(2,6-dimethyl-7-benzofuranyl)-2,6-dimethyl-3 (2H)-pyridazinone;
5-hydroxy-2,6-dimethyl-4-(3-methyl-1,2-benzisothiazol-4-yl)-3 (2H)-pyridazinone;
5-hydroxy-2,6-dimethyl-4-(5-methylbenzo[b]thien-4-yl)-3 (2H)-pyridazinone; and
1,6-dihydro-1,3-dimethyl-5-(5-methylbenzo[b]thien-4-yl)-6-oxo-4-pyridazinyl ethyl carbonate.

9. A herbicidal composition comprising a compound of claim 1 and at least one component selected from the group consisting of surfactants, solid diluents and liquid diluents.

10. A herbicidal composition comprising a compound of claim 1, at least one additional active ingredient selected from the group consisting of other herbicides and herbicide safeners, and at least one component selected from the group consisting of surfactants, solid diluents and liquid diluents.

11. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

12. A method for controlling the growth of undesired vegetation comprising contacting the vegetation or its environment with a herbicidally effective amount of a compound of claim 1.

* * * * *